US007164049B2

(12) United States Patent
Ebner et al.

(10) Patent No.: US 7,164,049 B2
(45) Date of Patent: Jan. 16, 2007

(54) PROCESS FOR THE PREPARATION OF 3,3-DIMETHYLBUTANAL

(75) Inventors: Jerry R. Ebner, St. Charles, MO (US); Zhi Guo, Chicago, IL (US); Arnold Hershman, St. Louis, MO (US); Loraine M. Klein, Streamwood, IL (US); William D. McGhee, Fenton, MO (US); Mark Paster, Chesterfield, MO (US); Indra Prakash, Hoffman Estates, IL (US)

(73) Assignee: The Nutrasweet Company, Norwalk, CT (US)

( * ) Notice: Subject to any disclaimer, the term of this patent is extended or adjusted under 35 U.S.C. 154(b) by 0 days.

(21) Appl. No.: 10/400,558

(22) Filed: Mar. 27, 2003

(65) Prior Publication Data

US 2004/0006247 A1    Jan. 8, 2004

Related U.S. Application Data

(62) Division of application No. 09/575,107, filed on May 19, 2000, now Pat. No. 6,573,409.

(60) Provisional application No. 60/142,122, filed on Jul. 2, 1999.

(51) Int. Cl.
*C07C 27/00* (2006.01)

(52) U.S. Cl. ...................... 568/876; 568/877

(58) Field of Classification Search ................ 568/876, 568/877
See application file for complete search history.

(56) References Cited

U.S. PATENT DOCUMENTS

| | | | |
|---|---|---|---|
| 2,660,602 | A | 11/1953 | Wiese |
| 3,754,052 | A | 8/1973 | Hoffman |
| 3,836,553 | A | 9/1974 | Fenton et al. |
| 3,940,446 | A | 2/1976 | Kahn |
| 4,110,403 | A | 8/1978 | Ichikawa et al. |
| 4,175,204 | A | 11/1979 | Babler |
| 4,359,587 | A | 11/1982 | Abdurakhmanov et al. |
| 4,421,938 | A | 12/1983 | Windawi |
| 4,433,175 | A | 2/1984 | Kaufhold |
| 4,590,313 | A | 5/1986 | Grey et al. |
| 4,891,446 | A | 1/1990 | Slaugh |
| 5,103,066 | A | 4/1992 | Dessau |
| 5,227,530 | A | 7/1993 | Satek et al. |
| 5,480,668 | A | 1/1996 | Nofre et al. |
| 5,510,508 | A | 4/1996 | Claude et al. |
| 5,728,862 | A | 3/1998 | Prakash |
| 5,770,775 | A | 6/1998 | Katritzky et al. |
| 5,808,062 | A | 9/1998 | Domagala et al. |
| 5,856,584 | A | 1/1999 | Prakash et al. |

FOREIGN PATENT DOCUMENTS

| | | |
|---|---|---|
| EP | 0 529 804 B1 | 4/1996 |
| EP | 0 747 123 B1 | 12/1996 |
| EP | 0 866 073 B1 | 9/1998 |
| EP | 0 884 299 B1 | 12/1998 |
| GB | 693390 | 7/1953 |
| GB | 1 500 447 | 1/1975 |
| GB | 1 500 884 | 8/1976 |
| WO | WO 97/18035 | 5/1997 |
| WO | WO 97/49490 | 12/1997 |
| WO | WO 98/00233 | 1/1998 |
| WO | WO 99/21817 | 5/1999 |

OTHER PUBLICATIONS

Banthorpe, D., et al., "Mechanism of Elimination Reactions. Part XX. The Inessentiality of Steric Strain in Biomolecular Olefin Elimination," J. Chem. Soc., 1960, pp. 4054-4087 (incomplete copy).
Brandstrom, A., et al., "A Method for the Preparation of *tert*-Alkylacetic Acids," Acta. Chem. Scand., vol. 13., No. 3, 1959, pp. 608-610.
Kosolapoff, G., "Preparation of Alcohols by the Grignard Method from Olefin Oxides. II. Synthesis of 3,3-dimethyl-1-butanol and 4,4-dimethyl-1-pentanol from Ethylene Oxide and 2-heptanol, and of 5-methyl-5-hexanol from Propylene Oxide," Chem. Abstracts, vol. 43, No. 16, 1949, Abstract No. 6155b.
Nystrom, et al., "Reduction of Organic Compounds by Lithium Aluminum Hydride. II. Carboxylic Acids," JACS, vol. 69, No. 1197, 1947, pp. 2548-2549.
Ipatieff, et al., "Study in the Terpene Series. X. Isomerization Accompanying Hydrogenolysis of Alcohols," The Journal of the American Chemical Society, vol. 73, Feb. 1951, pp. 553-555.
Randriamahefa, et al., "Improved Synthesis of Tertiary Alkylacetic Acids and Esters," Journal of Synthetic Organic Chemistry, No. 5, 1985, pp. 493-495.
Karleskind, et al., "Catalytic High Presusre Hydrogenation," Oils and Fats Manual, vol. 2, pp. 1083-1084.
Pct International Search Report, PCT/US00/17946, Nov. 30, 2000, 5 pages.
Reid, M., et al., "Molecular Characterization of Microbial Alcohol Dehydrogenases," Critical Reviews in Microbiology, 1994, 20(1), pp. 13-56.
Augustine, R., et al., "Hydrogenation V: Carbonyl Compounds," Heterogeneous Catalysis for the Synthetic Chemist, Chapter 18, Jun. 1996, pp. 439-472.
Christiansen, J., et al., "A Method for the Preparation of Trialkylacetaldehydes," Acta Chem. Scand. 13, No. 3, 1959, pp. 611-613.

(Continued)

*Primary Examiner*—Sikarl A. Witherspoon
(74) *Attorney, Agent, or Firm*—Senniger Powers

(57) ABSTRACT

3,3-Dimethylbutanal is prepared from 3,3-dimethylbutanol. Intermediate 3,3-dimethylbutanol is obtained by reacting ethylene, isopropylene and a mineral acid to produce a 3,3-dimethylbutyl ester which is hydrolyzed to the alcohol. The hydrolysis step is effectively carried out by reactive distillation. Alternatively, 3,3-dimethylbutanal is prepared from 3,3-dimethylbutanol obtained by reduction of the corresponding carboxylic acid or 1,2-epoxy-3,3-dimethylbutane, or by hydrolysis of 1-halo-3,3-dimethylbutane. Fixed bed gas phase and stirred tank liquid phase processes are provided for converting 3,3-dimethylbutanol to 3,3-dimethylbutanal by catalytic dehydrogenation.

23 Claims, 10 Drawing Sheets

OTHER PUBLICATIONS

Dave, P., et al., "An Improved Direct Oxidation of Alkyl Halides to Aldehydes," Synthetic Communications, 16(11), 1986, pp. 1343-1346.

Kryukov, S., et al., "Synthesis of Oxygen-Containing Organic Compounds Based on $C_5$-$C_6$ Olefins," Neftekhimiya, undated, vol. 19, No. 5, pp. 762-766.

Cherkaev, V., et al., "Preparation of Aldehydes by Catalytic Dehydrogenation of Alcohols," Maslo-Zhir. Prom. 34(11), 1968, pp. 22-25 (translated from Russian, Jan. 1999).

Gulkova, D., et al., "Dehydrogenation of Substituted Alcohols to Aldehydes on Zinc Oxide-Chromium Oxide Catalysts," Czech. Collect. Chem. Commun., 1992, 57(11), pp. 2215-2226.

Jung, C., et al., "Dehydrogenation of Alcohols and Hydrogenation of Aldehydes Using Homogeneous Ruthenium Catalysts," Organometallics, 1992, vol. 1, No. 4, pp. 658-666.

Krohn, K., et al., "Titanium- or Zirconium-Catalyzed Selective Dehydrogenation of Benzyl Alcohols to Aldehydes and Ketones with *tert*-Butyl Hydroperoxide," Chem. Ber., 1990, 123(6), pp. 1357-1364.

Podrebarac, G., et al., "More Uses for Catalytic Distillation," Chemtech, 1997, 27(5), pp. 37-45.

Aramendia, M., et al., "The Selectivity of $NaZnPO_4$ in the Dehydrogenation of Alcohols," Chemistry Letters, 1994, Issue 8, pp. 1361-1364.

Liu, X. et al., "The Bis(bipyridine)copper(II)-Induced Activation of Dioxygen for the Catalytic Dehydrogenation of Alcohols," J. Am. Chem. Soc, Nov. 10, 1992, 115(8), pp. 3239-3243.

Dobson, A., et al., "Complexes of the Platinum Metals. 7.[1] Homogenous Ruthenium and Osmium Catalysts for the Dehydrogenation of Primary and Secondary Alcohols," Inorganic Chemistry, 1977, vol. 16, No. 1, pp. 137-142.

Rybak, W., et al., "Dehydrogenation of Alcohols Catalyzed by Polystyrene-Supported Ruthenium Complexes," J. Mol. Catal., 1981, 11(2-3), pp. 365-370.

Neumann, R., "Mixed Addenda Phosphomolybdovanadates as Catalysts for Oxidations with Dioxygen and Hydrogen Peroxide," Polyoxometalates, pp. 307-313.

Simpson, M., et al., "Catalytic Applications of Rhodium Complexes Containing Trialkylphosphines," Coordination Chemistry Reviewed, 1996, 155, pp. 163-207.

Zhang, B., et al., "Metal Fibre—A Novel Catalyst Material for Selective Dehydrogenation of Alcohols," Proceedings of the 10th International Congress on Catalysis, Jul. 19-24, 1992, pp. 2177-2280.

Yanagisawa, A., et al., "Selective Isomerization of 1,2-Epoxyalkanes to Aldehydes with Lithum Dialkylamides," J. Chem. Sco., Chem. Commun., 1994, pp. 2103-2104.

Mischitz, M., et al., "Asymmetric Microbial Hydrolysis of Epoxides," Tetrahedron: Asymmetry, 1995, vol. 6, No. 6, pp. 1261-1272.

Ipatieff, V., et al., "Study in the Terpene Series. X. Isomerization of Accompanying Hydrogenolysis of Alcohols," Ipatieff High Pressure and Catalytic Laboratory, Department of Chemistry, Northwestern University, Feb. 1951, pp. 553-555.

Wann, S., et al., "Reduction of Carboxylic Acid Derivatives by $BH_4$ in Acidic Dimethyl Sulfoxide," J. Org. Chem., 1981, 46, pp. 2579-2581.

Adkins, H., et al., "The Preparation of Aldehydes and Ketones by Dehydrogenation of Alcohols Over Copper-Chromium Oxide," The Journal of The American Chemical Society, Jul. 1933, pp. 2992-2994, vol. 55, Easton, PA, US.

3,3-DIMETHYLBUTANAL PROCESS SCHEME
CATALYTIC DEHYDROGENATION OF
3,3-DIMETHYLBUTANOL

PROCESS FOR THE PREPARATION OF 3,3-DIMETHYLBUTANAL

REFERENCE TO RELATED APPLICATIONS

This application is a divisional of U.S. Nonprovisional Application Ser. No. 09/575,107, filed May 19, 2000, which issued as U.S. Pat. No. 6,573,409 on Jun. 3, 2003. U.S. Ser. No. 09/575,107 claims the benefit of U.S. Provisional Application Ser. No. 60/142,122, filed Jul. 2, 1999.

BACKGROUND OF THE INVENTION

This invention relates to the preparation of 3,3-dimethyl butanal, and more particularly to improved processes for preparing 3,3-dimethylbutanal and precursors therefor.

Nofre et al. U.S. Pat. No. 5,480,668 describes artificial sweetening agents comprising N-substituted derivatives of aspartame. A preferred example as described by Nofre is N-[N-(3,3-dimethybutyl)-L-α-aspartyl]-L-phenylalanine 1-methyl ester. As the reference further describes, this product may be produced by reaction of 3,3-dimethylbutyraldehyde (3,3-dimethylbutanal) with aspartame and a reducing agent such as sodium cyanoborohydride in a solvent medium such as methanol.

Nofre U.S. Pat. No. 5,510,508 and Prakash U.S. Pat. No. 5,728,862 describe preparation of N-[N-(3,3-dimethylbutyl)-L-α-aspartyl]-L-phenylalanine, 1-methyl ester by a reductive alkylation reaction comprising catalytic hydrogenation of the Schiff's based produced by condensation of 3,3-dimethylbutanal and aspartame.

To facilitate the manufacture of N-[N-(3,3-dimethybutyl)-L-α-aspartyl]-L-phenylalanine 1-methyl ester, there has been a need in the art for an improved and economical method for preparation of the 3,3-dimethylbutanal intermediate. Currently, 3,3-dimethylbutanal is available on the market only in limited quantities at prices that are very expensive. Previously available manufacturing processes have generally failed to provide satisfactory yields, or to produce an aldehyde intermediate of adequate purity, substantially free of by-products, such as t-butylacetic acid. Recently, improved methods have been developed, but a need has remained for a more satisfactory process for the commercial manufacture of 3,3-dimethylbutanal.

Prakash et al. U.S. Pat. No. 5,856,584 describes a process for the preparation of 3,3-dimethylbutanal by oxidation of 3,3-dimethylbutanol. Oxidizing components used in the process include an oxidizing metal oxide or 2,2,6,6-tetramethyl-1-piperidinyloxy, free radical, and an oxidizing agent such as sodium hypochlorite. Oxidation by a metal oxide may effected by contacting 3,3-dimethylbutanol in a vapor phase comprising an inert carrier gas with an oxidizing metal oxide. Oxidation by 2,2,6,6-tetramethyl-1-piperidinyloxy, free radical, and sodium hypochlorite may be conducted in a solvent system.

Slaugh U.S. Pat. No. 4,891,446 describes a process for catalytic dehydrogenation of saturated primary alcohols having a carbon number ranging from 5 to 20, preferably 7 to 18. The alcohol is passed over a fixed bed of brass particles in a vertical column or horizontal tubular reactor. Although hydrogen is a product of the reaction, additional hydrogen is introduced into the reactor in order to obtain good catalyst life or stability. Specific working examples are given for dehydrogenation of $C_9$, $C_{13}$, and $C_{15}$ alcohols.

Gulkova et al. "Dehydrogenation of Substituted Alcohols to Aldehydes on Zinc Oxide-Chromium Oxide Catalysts," *Collect. Czech. Chem. Commun.*, Vol. 57, pp. 2215–2226 (1992) reports the exploration of sixteen primary alcohols for the possibility of obtaining the corresponding aldehydes by dehydrogenation on solid catalysts. Among the substrates tested was 3,3-dimethyl-butanol. The reference reports certain rate constant information for the dehydrogenation of a 3,3-dimethylbutanol substrate, but does not include description of the particular conditions under which this substrate was converted to 3,3-dimethylbutanal.

Banthorpe et al., "Mechanism of Elimination Reactions. Part XX. The Inessentiality of Steric Strain in Bimolecular Olefin Elimination," *J. C. S.*, 1960, pp. 4084–4087 describes the dehydrogenation of 3,3-dimethylbutanol to 3,3-dimethylbutanal in which 3,3-dimethylbutanol was boiled into a vertical tube containing pumice supported copper chromite catalyst and surmounted by a reflux condenser. The catalyst became reduced after 40 minutes reaction and was regenerated by exposure to an air stream at 320° C. for 2 hours.

Where 3,3-dimethylbutanal is derived from 3,3-dimethylbutanol, the provision of a satisfactory commercial method for the preparation of the aldehyde also requires the selection and/or development of an economically effective method for the preparation of the alcohol.

Hoffman et al. U.S. Pat. No. 3,754,052 describes reaction of isobutylene, ethylene and sulfuric acid in the presence of isobutane to produce the sulfate ester of 3,3-dimethylbutanol in isobutane. Unreacted ethylene is removed and the sulfate ester is alkylated with isobutane at $\geq 25°$ C. to produce 2,3-dimethylbutane.

Wiese U.S. Pat. No. 2,660,602 describes a process for the preparation of branched primary sulfate esters by reaction of ethylene, an olefin co-reactant and sulfuric acid, particularly including the preparation of 3,3-dimethylbutyl hydrogen sulfate where the olefin co-reactant is isobutylene. The reaction is carried out by simultaneously contacting strong sulfuric acid with ethylene and the co-reactant, preferably in the cold. A high ethylene to co-reactant ratio is maintained. A hydrocarbon diluent is preferably present in the reaction zone, particularly when employing low molecular weight co-reactants, i.e., less than $C_{12}$. The reference disclosed hydrolysis of 3,3-dimethylbutyl monohydrogen sulfate ester to 3,3-dimethylbutanol, and further suggests the preparation of the acetate of the alcohol, which is said to be useful as a lacquer solvent. Wiese et al. also suggest preparation of di-octyl phthalate ester plasticizers by esterification of phthalic anhydride with branched chain alcohol.

Reactions have been described in which carboxylic acids and esters are reduced to alcohol by reaction with strong reducing agents commonly lithium aluminum hydride. Such reactions must be handled with caution due to the high reactivity of the reducing agents. *Journal of Organic Chemistry*, Vol. 46 (1981), pp. 2579–2581 discloses that carboxylic acid amides can be reduced to the corresponding amines by a combination of sodium borohydride and methane sulfonic acid and dimethylsulfoxide (DMSO). The same paper discloses that acetic acid and phenyl acetic acid can be reduced to corresponding alcohols under similar conditions. However, the paper contains no suggestion of the reduction of other acids to the corresponding alcohols. Sodium borohydride is a widely used reducing agent and relatively safe to work with but has not been considered generally suitable for reducing the carboxylate group due to its mild reducing capacity.

*Journal of the American Chemical Society*, Vol. 73 (1951), p. 555 discloses hydrolysis of 1-chloro-3,3-dimethylbutane with potassium carbonate in a closed system to produce 3,3-dimethylbutanol in 65% yield. Since carbon dioxide is generated in the reaction, the procedure requires operation at high pressure to avoid stripping out the aqueous phase.

SUMMARY OF THE INVENTION

Among the several objects of the present invention, therefore, may be noted the provision of a process for the manufacture of 3,3-dimethylbutanal; the provision of such a process which uses readily available and inexpensive raw materials; the provision of a process which produces intermediates for 3,3-dimethylbutanal; the provision of processes which provide high yields in the preparation of 3,3-dimethylbutanal and/or intermediates therefor; the provision of a process for the preparation of 3,3-dimethylbutanol; the provision of a process for preparation of 3,3-dimethylbutanol and use thereof as a substrate for conversion to 3,3-dimethylbutanal; the provision of a process for producing 3,3-dimethylbutanol and converting it to 3,3-dimethylbutanol without substantial refining of the 3,3-dimethylbutanol; the provision of a process for the preparation of 3,3-dimethylbutanal which does not require generation of halide byproducts or impurities; the provision of processes for the manufacture of 3,3-dimethylbutanol and 3,3-dimethylbutanal which can be implemented with acceptable capital investment and operating cost; and the provision of a process for preparation of 3,3-dimethylbutanal and use thereof for the preparation of N-[N-(3,3-dimethylbutyl)-L-α-aspartyl]-L-phenylalanine 1-methyl ester (sometimes hereinafter referred to as "neotame").

Briefly, therefore, the present invention is directed to a process for the preparation of 3,3-dimethylbutanal. An ester of 3,3-dimethylbutanol is prepared by reacting isobutylene, ethylene, and the mineral acid. The ester is hydrolyzed to produce 3,3-dimethylbutanol; and the alcohol is converted to 3,3-dimethylbutanal.

The invention is further directed to a process for the preparation of 3,3-dimethylbutanal comprising contacting 3,3-dimethylbutanol with a catalyst for the dehydrogenation of an alcohol to a corresponding aldehyde at a turnover ratio of at least 5 moles dimethylbutanal per mole catalyst active phase prior to any interruption of the reaction for regeneration of catalyst.

The invention further comprises a process for preparation of 3,3-dimethylbutanol in which a hydrolysis feed mixture comprising a 3,3-dimethylbutyl ester and a mineral acid is heated in the presence of water, thereby hydrolyzing the ester and producing a hydrolysis reaction mixture comprising 3,3-dimethylbutanol. The 3,3-dimethylbutanol formed in the hydrolysis is distilled from the hydrolysis reaction mixture.

The invention is further directed to a process for the preparation of 3,3-dimethylbutanal in which a gas phase comprising 3,3-dimethylbutanol and an inert gas is contacted with a dehydrogenation catalyst to produce a dehydrogenation reaction product gas containing 3,3-dimethylbutanal at a turnover ratio of at least 5 moles dimethylbutanal per mole catalyst active phase prior to any interruption of the reaction for regeneration of catalyst. 3,3-Dimethylbutanal is recovered from the dehydrogenation reaction mixture.

The invention is further directed to a process for the preparation of 3,3-dimethylbutanal in which a slurry comprising a particulate dehydrogenation catalyst and 3,3-dimethylbutanol is prepared, and 3,3-dimethylbutanol is converted to 3,3-dimethylbutanal by catalytic dehydrogenation in the slurry. A dehydrogenation reaction product slurry comprising the catalyst and 3,3-dimethyl butanal is produced. 3,3-Dimethylbutanal is recovered from the dehydrogenation reaction product slurry.

The invention further comprises a process for the preparation of 3,3-dimethylbutanal in which 3,3-dimethyl butanoic acid or an ester thereof is contacted with the reducing agent thereby producing 3,3-dimethylbutanol. 3,3-Dimethylbutanol is converted to 3,3-dimethyl butanal.

The invention is also directed to a process for the preparation of 3,3-dimethylbutanal in which a substrate selected from the group consisting of 1-chloro-3,3-dimethylbutane and 1-bromo-3,3-dimethylbutane is hydrolyzed to produce 3,3-dimethyl butanol. 3,3-Dimethylbutanol is converted to 3,3-dimethylbutanal.

The invention is further directed to a process for preparing 3,3-dimethylbutanal in which 3,3-dimethylbutanal is prepared by hydrolysis of 1-halo-3,3-dimethylbutane or 1-acyloxy-3,3-dimethylbutane in the presence of a base; and the 3,3-dimethylbutanol is converted to 3,3-dimethylbutanal.

The invention is also directed to a process for preparing 3,3-dimethylbutanol in which 1,2-epoxy-3,3-dimethylbutane oxide is reduced to 3,3-dimethylbutanol and 3,3-dimethylbutanol is converted to 3,3-dimethylbutanal.

The invention is also directed to a process for preparation of 3,3-dimethylbutanal in which a t-butyl organometallic compound is reacted with ethylene oxide to form 3,3-dimethylbutanol and 3,3-dimethylbutanol is converted to 3,3-dimethylbutanal.

The invention is further directed to a process for the preparation of 3,3-dimethylbutanal in which 3,3-dimethylbutanol is contacted with a catalyst for the dehydrogenation of an alcohol to a corresponding aldehyde. the catalyst is substantially non-toxic to humans.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
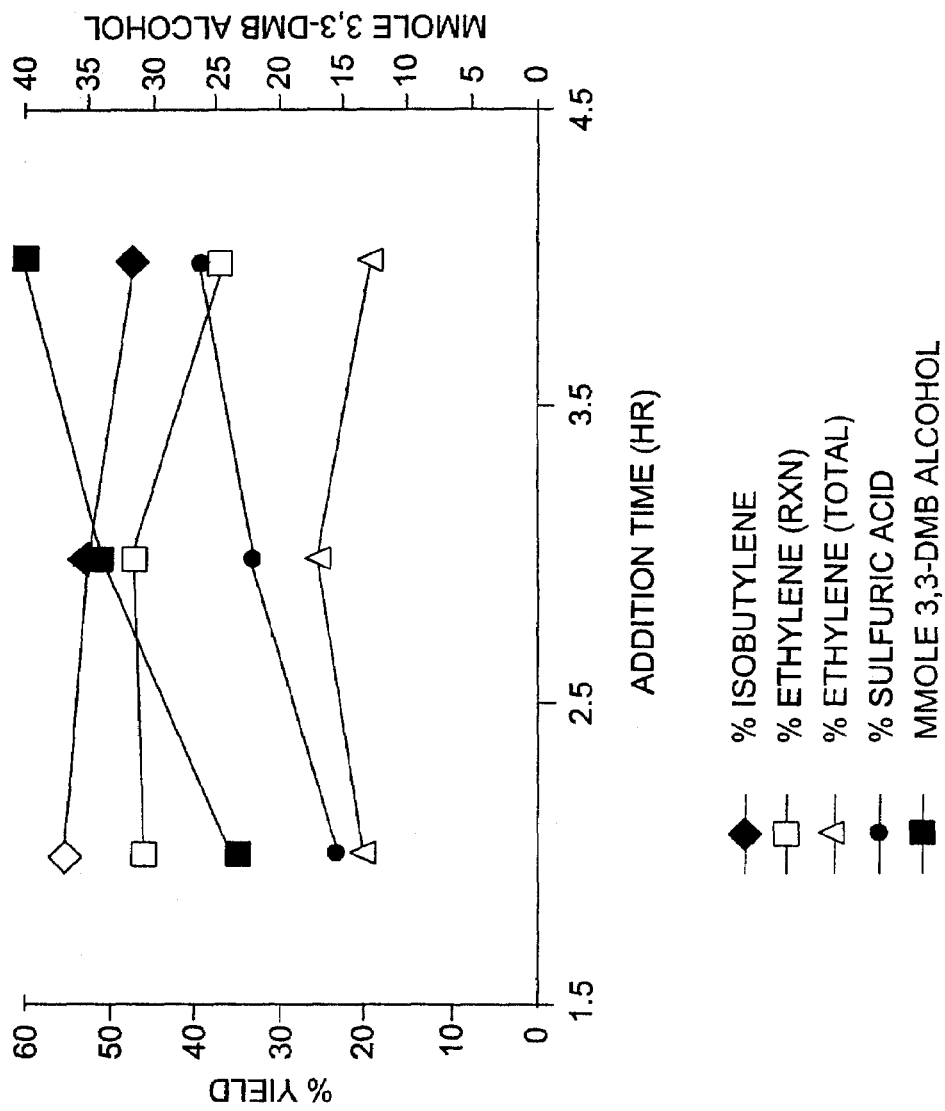
FIG. 1 plots total 3,3-dimethylbutanol yield and yield on sulfuric acid, ethylene and isobutylene as a function of reactant addition time during the alkylation/esterification reaction for the combined alkylation/esterification and hydrolysis reactions described in Example 2 as conducted under the conditions designated in the graph.

In accordance with the present invention, novel and advantageous processes have been developed for the preparation of 3,3-dimethylbutanol, 3,3-dimethylbutanal and N-[N-(3,3-dimethylbutyl)-1-α-aspartyl]-L-phenylalanine 1-methyl ester (neotame).

In an alkylation and esterification reaction comprising the initial step in the preparation of 3,3-dimethylbutanol, isobutylene, ethylene and a mineral acid are reacted to produce a mixture comprising an ester of 3,3-dimethylbutanol and the mineral acid. For example, using sulfuric acid as the mineral acid, monoesters and diesters are typically produced according the following reaction:

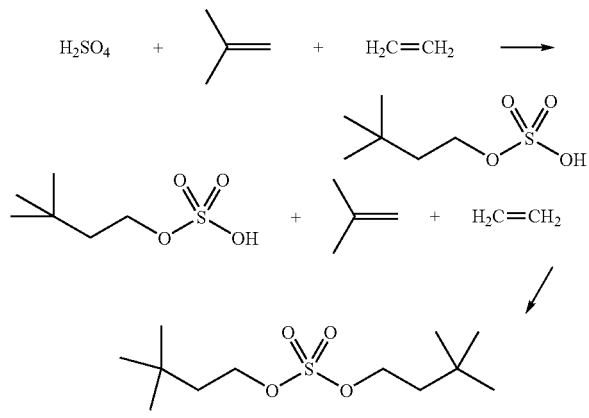

The 3,3-dimethylbutyl monoesters and diesters are hydrolyzed to produce 3,3-dimethylbutanol, which is preferably recovered from the hydrolysis reaction mixture by distillation:

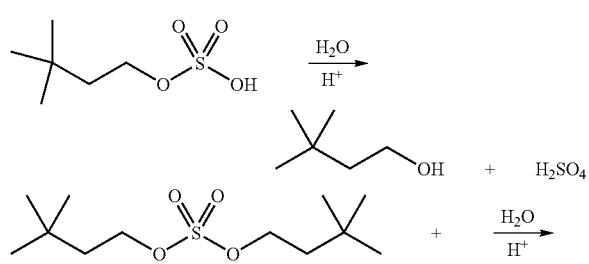

3,3-Dimethylbutanol is converted to 3,3-dimethylbutanal by catalytic dehydrogenation:

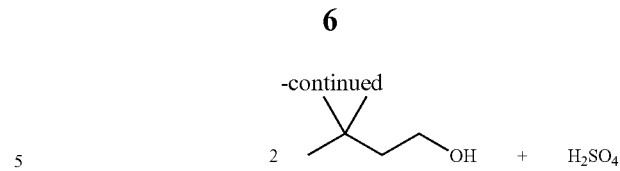

Optionally, in certain embodiments of the invention, 3,3-dimethylbutanol can be converted to 3,3-dimethylbutanal in the presence of molecular oxygen and a catalyst for oxidative dehydrogenation of an aldehyde:

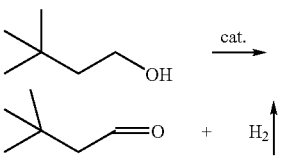

3,3-Dimethylbutanal is useful as a raw material for the preparation of N-(3,3-dimethylbutyl)aspartame, a novel sweetener as described in U.S. Pat. No. 5,480,668. Preparation of neotame may proceed by reductive alkylation of aspartame comprising formation of the Schiff's base:

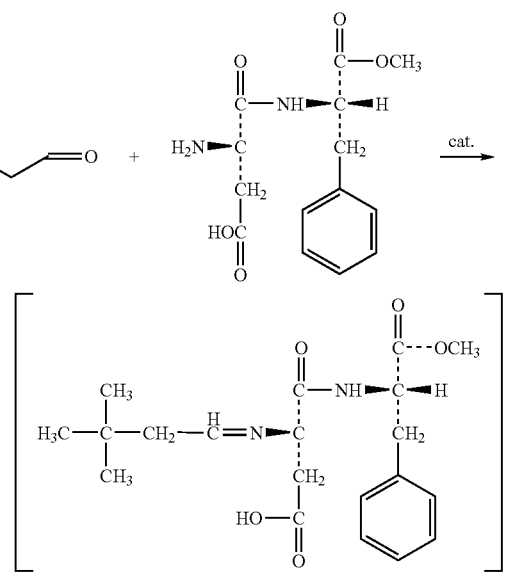

and catalytic addition of hydrogen across the —C=N— double bond to yield:

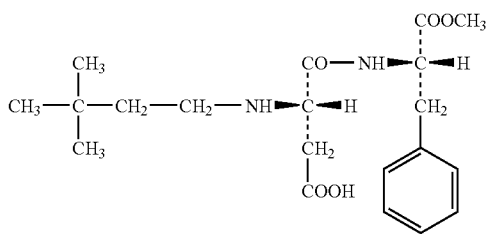

In the preparation of 3,3-dimethylbutanol esters, isobutylene is introduced into a mineral acid medium under an ethylene atmosphere. A variety of mineral acids can be used to catalyze the reaction and supply the anion from which the esters are formed. A relatively strong acid is required, e.g., an acid exhibiting $pK_a$ no greater than about 0. Among the acids which can be used in the reaction are sulfuric, oleum, sulfurous, and trifluoromethane sulfonic, and nitric. Alternatively, a cation-exchange resin, e.g., a sulfonated resin such as that sold under the trade designation "Nafion" by E.I. duPont de Nemours & Co can be used to catalyze the reaction. Sulfuric acid is preferred.

In conducting the alkylation and esterification reaction, isobutylene and ethylene are brought simultaneously into contact with the mineral acid within an alkylation/esterification reaction zone. In the reaction zone, the olefin reactants are introduced into a condensed phase reaction medium which comprises the mineral acid, and normally further comprises a nonpolar organic solvent. Thus, the reaction system is typically three phase, including the acid phase, the solvent phase and a gas phase comprising primarily ethylene. Preferably, the reactants are contacted under relatively vigorous agitation to promote transfer of ethylene from the gas phase to the solvent phase, establish substantial interfacial contact between the solvent and acid phases, promote transfer of the olefinic reactants to the interface between the liquid phases, and promote transfer of product esters from the interface into the acid phase. While the process of the invention does not depend on any particular theory, it is believed that, in the presence of acid, a t-butyl cation is formed from the isobutylene and reacts with the ethylene and mineral acid to produce the monoester, e.g., in the case of sulfuric acid:

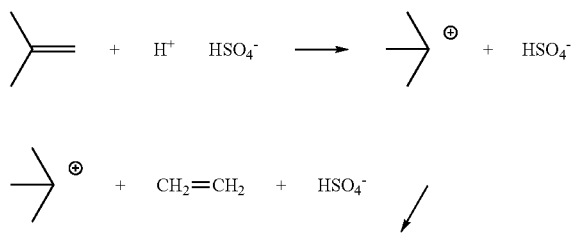

Typically, some fraction of the monoester further reacts with isobutylene and ethylene to produce the diester:

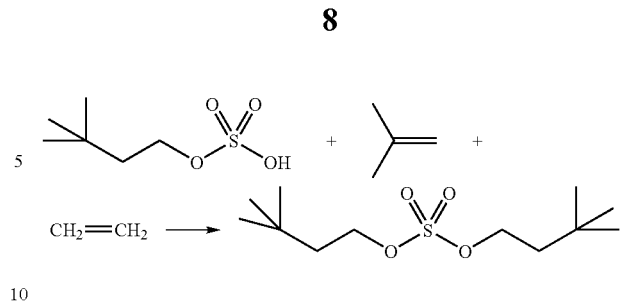

Formation of the ethyl monoester, diethyl ester and mixed 3,3-dimethylbutyl/ethyl ester may compete with the formation of the desired ester intermediates:

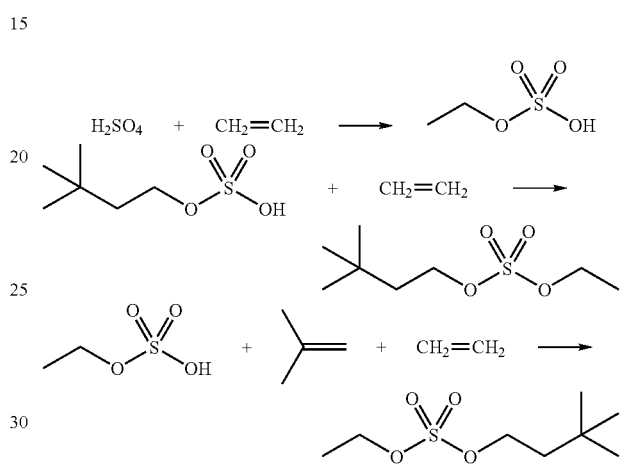

Alkylation reactions can also occur to produce various branched chain hydrocarbon by-products of molecular weight characteristic of internal combustion engine fuels.

The extent of formation of such by-products can be minimized by appropriate control of the reaction conditions, including substantially simultaneous contact of the mineral acid medium with both isobutylene and ethylene. If ethylene is brought into contact with sulfuric acid in the absence of isobutylene, substantial formation of ethyl esters is likely to result. If contact between isobutylene and sulfuric acid is maintained over any substantial time period in the absence of ethylene, formation of isobutylene dimers, polymers, and other alkylation products can proceed.

The reactions may proceed at essentially any temperature, but are preferably conducted in the cold to maximize yield of the desired ester products and minimize formation of "gasoline" by-products. Preferred reaction temperature are below 10° C., more preferably below about 0° C. For commercial manufacturing operations, the reaction temperature is most preferably in the range of about −20° to about 0° C. It has been observed that the formation of the desired ester products

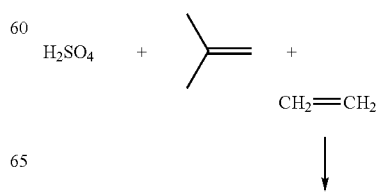

-continued

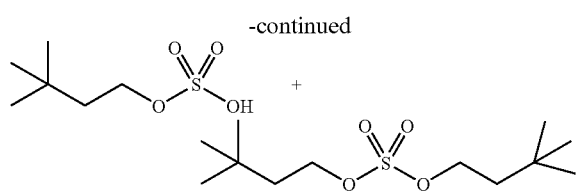

is nearly instantaneous. Accordingly, yields of desired product might be further enhanced without material loss in productivity by operation at even lower temperatures, e.g., −20° to −40° C., but at temperatures in the latter range the economic benefit in yield may be more than offset by the economic penalty in refrigeration costs.

To maximize the yield of the desired ester products, the water content of the reaction medium is preferably maintained at a relatively low level. Reaction rates also tend to decline with water content, though the reactions are in any case so rapid that the effect on rate is not a significant economic factor. To achieve desired yields using sulfuric acid, the strength of the acid as charged to the reaction zone is preferably 90–100%, more preferably 95–100% by weight on an organic-free basis. Even higher acid strengths may be desirable, extending into the oleum range. Higher sulfuric acid concentrations may be useful not only in providing enhanced yields, but also in allowing use of relatively inexpensive Fe/Cr alloys, or even carbon steel, as materials of construction for alkylation/esterification reaction process equipment. Alternatively, higher alloys, for example Ni/Mo alloys such as Hastelloy B or Hastelloy C-276, may be used. In any event, to assure a given minimum acid strength at terminal conditions, it is desirable to introduce acid of somewhat higher strength into the reaction, since consumption of conjugate base in the esterification effectively results in dilution of the acid. Comparable limits on water content are preferably imposed where acids other than sulfuric are used for the reaction.

Isobutylene may be introduced in liquid or gaseous form into the alkylation/esterification reaction zone, but is preferably introduced as a liquid to minimize heat load on the reactor refrigeration system. Ethylene is typically introduced as a gas; and an ethylene pressure of between about 20 psig (275 kPa ga.) and about 200 psig (1400 kPa ga.), preferably between about 40 psig (550 kPa ga.) and about 140 psig (965 kPa ga.) is maintained in the reaction zone. If the ethylene pressure is significantly lower than about 40 psig, excessive formation of hydrocarbon by-products may result, while at pressures above 140 psig, or especially above 200 psig, the extent of ethyl ester formation is increased. Each of isobutylene and ethylene may be introduced either into the head space of the reactor or below the surface of the condensed phase mixture. Optionally, either or both of isobutylene and ethylene may be introduced as a solution in an organic solvent. Alternatively, ethylene may be introduced into the reaction zone in the liquid state and the reaction conducted entirely in a system comprising two condensed phases.

The esterification/alkylation reaction may be conducted in either a batch or continuous mode. To minimize oligomerization and formation of by-product hydrocarbons, the concentration of isobutylene is preferably kept as low as feasible. In a batch reaction system, the reactor may initially be charged with mineral acid and solvent, after which the introduction of isobutylene is commenced and the reaction zone essentially simultaneously pressurized with ethylene. Isobutylene is preferably introduced at a controlled rate of between about 0.01 and about 0.5 liters per hour per liter of the combined condensed phase mixture. Whatever the mode by which isobutylene is introduced, or the rate of its introduction, a molar excess of sulfuric acid vs. isobutylene is preferably maintained throughout the reaction in order to minimize isobutylene oligomerization. Preferably, the molar ratio of sulfuric acid to isobutylene is maintained at at least about 1 at all times during the reaction, and the cumulative ratio of sulfuric acid to isobutylene introduced into the reaction zone is between about 2 and about 1. An undue excess of sulfuric acid may result in excessive formation of ethyl sulfate by-product. Introduction of ethylene is regulated to maintain an ethylene pressure in the range indicated above.

The reaction system is preferably agitated vigorously to establish intimate interfacial contact for mass transfer to and/or across the interface. Especially vigorous agitation may be indicated because of the substantial difference between the density of the acid phase and the liquid organic phase. To provide the requisite interfacial contact and mass transfer, conventional mixing principles may be applied by those skilled in the art to provide appropriate geometry, shear, and pumping effects by selection of impeller type, rotational and tip speed, baffling, internal coils, dip tubes, etc. Further to facilitate mass transfer between the phases, phase transfer catalysts, such as tetra alkyl ammonium halides or hydroxides, alkyl phosphonium halides, benzyl trialkylammonium halides, or benzyl trialkylammonium hydroxides, may be incorporated into the reaction mixture.

In an alternative, semi-batch co-addition system, isobutylene and mineral acid are simultaneously introduced into the batch reactor, preferably at controlled rates while a pressurized ethylene atmosphere is maintained therein. Co-addition of isobutylene and acid tends to minimize competitive reaction of ethylene and acid. The solvent and minor fraction of the mineral acid are preferably charged to the reactor before co-addition begins. Optionally, solvent can be added together with acid and isobutylene, in which instance the isobutylene and/or ethylene may be introduced as a solution in the organic solvent. In a further alternative, isobutylene and acid can be metered into an initial charge consisting solely of solvent under ethylene pressure. Since the reaction proceeds essentially instantaneously, the batch is essentially finished when addition of the condensed phase components is complete. Controlled co-addition of isobutylene and acid minimizes exposure of unreacted isobutylene and ethylene to the acid phase, and may therefore tend to reduce the extent of by-product formation. After co-addition is complete, the reaction mass is removed from the alkylation/esterification reactor, but a reaction product heel may be maintained in the reactor to provide a medium for reaction heat removal during the co-addition phase of the succeeding batch, as described immediately below.

According to a modification of the co-addition process, the rate of sulfuric acid addition is controlled so that the entire charge of acid is completed before the addition of isobutylene is complete. In practice of this embodiment of the invention, solvent and optionally a small fraction of the acid, e.g., 1–25% of the overall acid requirement, are initially charged to the reactor, after which ethylene pressure is applied the remainder of the acid and the isobutylene are metered into the reactor at a relative ratio effective to complete the acid addition well before addition of the isobutylene is finished. Thus, for example, the acid may be metered into the reactor in molar ratio to isobutylene of between 1.1 and 2.5, preferably between about 1.2 and about 1.7, so that addition of acid is completed one to five hours before completion of isobutylene addition. The reaction mixture is maintained under intense agitation during addition of acid and isobutylene. This alternative has been observed to be capable of providing a substantial reactor payload and a relatively high yield on mineral acid and isobutylene.

Whatever the schedule of isobutylene and acid addition, the cumulative charge of isobutylene and acid to a batch reactor, and the instantaneous concentrations of isobutylene and acid, are preferably controlled to provide the greatest reactor payload consistent with satisfactory yield of desired sulfate ester intermediate. If the isobutylene concentration is too high, excessive oligomerization of isobutylene may occur and yields will suffer; if the isobutylene concentration is too low, productivity may suffer. In a batch or semi-continuous system, cumulative acid to isobutylene ratio is preferably between about 0.5 and about 4, preferably between about 1 and about 2.

The alkylation and esterification reaction is substantially exothermic. For removal of exothermic heat, the autoclave may be jacketed and/or provided with internal cooling coils. Alternatively, or in addition, the condensed phase reaction mixture may be circulated between the autoclave and an external heat exchanger. A refrigerated cooling medium, e.g., brine solution or Syltherm, is passed through the jacket, coils and/or coolant fluid side of the external heat exchanger. Optionally, a liquefied refrigerant can be supplied to the jacket, coils or external heat exchanger for removal of reaction heat by evaporative cooling. The reactor may be operated with full cooling throughout the reaction, and the temperature is controlled by regulating the rate of introduction of isobutylene into the reaction zone. In co-addition, the rate of addition of isobutylene may be controlled in response to temperature, and the rate of addition of acid ratioed to the measured rate of addition of isobutylene. Preferably, the capacity of the cooling system is designed to permit a relatively high rate of isobutylene introduction, e.g., in the range specified hereinabove. The reaction may be conducted with a relatively low volumetric ratio of solvent phase to acid phase in the reactor, thereby maximizing the payload of desired ester product(s), which accumulate within the acid phase forming a pregnant liquor comprising mineral acid and 3,3-dimethylbutyl esters. Generally, the batch is terminated when the sum of the monoester and diester content of the pregnant liquor is between about 10 and about 90 mole %, preferably between about 30 and about 60 mole %.

Because the alkylation and esterification reaction is so rapid, the reaction may optionally be carried out in a continuous stirred tank reactor ("CSTR"). The configuration of a CSTR is essentially the same as that of a batch autoclave, and isobutylene and ethylene feeds may be controlled on the same basis. Sulfuric acid is introduced at a rate sufficient to maintain a desired organic-free acid strength. Reaction mixture may be removed, e.g., from the reaction product stream that is circulated through an external heat exchanger, at a rate controlled to maintain a constant condensed phase level in the reactor. Since conversion is essentially instantaneous, productivity is governed essentially by heat transfer capacity. Residence time is not critical, but reactor volume should be sufficient to afford an inventory of reaction mixture adequate for desired heat transfer capacity and stable temperature control.

In accordance with a further option, the alkylation and esterification reaction may be carried out in a plug flow reactor. Various conventional forms of plug flow reactors can be used to conduct the reaction, with conventional heat transfer means being provided to remove the exothermic heat of reaction and maintain the temperature in the desired range as described hereinabove.

The organic solvent used in the reaction is preferably a liquid aliphatic or aromatic hydrocarbon of moderate volatility, e.g., $C_5$ to $C_{18}$, that is compatible with the reaction, i.e., does not condense, polymerize or otherwise react with ethylene, isobutylene or the mineral acid. The solvent serves as a medium of absorption of ethylene, and as a solvent for isobutylene, through which the two olefins are brought into contact with the acid phase in substantially uniform ratios to one another. The solvent also serves to remove alkylation by-products from the acid interface where the desired reaction is believed to substantially occur. It is preferred that the hydrocarbon solvent be straight chain rather than branched, in order to minimize the formation of alkylation by-products. As noted, the reaction may be carried out in a batch or semi-batch system using a relatively low volumetric ratio of solvent to acid phase, e.g., less than 4 to 1, preferably less than about 3 to 1, more preferably between about 0.1 and about 2.5 to 1. Since dialkyl esters formed in the reaction have a substantial solubility in aliphatic solvents, the solvent to acid ratio is preferably maintained as low as possible to maximize reactor payload and yield.

It has further been discovered that the yields on ethylene can be improved by terminating introduction of ethylene after the reaction has proceeded for a period sufficient to achieve substantial conversion of isobutylene. For example, in the embodiment of the process comprising co-addition of sulfuric acid and isobutylene to the reaction zone during the reaction, the introduction of ethylene may be substantially reduced or terminated after about 50%, preferably between about 70% and about 80% of isobutylene has been charged to the reactor, typically within about 30 minutes before or after the time by which 95% of the sulfuric acid charge has been added, i.e., between 2 and 4 hours after the addition of acid and isobutylene has been commenced. After ethylene addition is substantially terminated, ethylene pressure is allowed to decay as ethylene is consumed during the remainder of the reaction cycle, thereby minimizing the amount of ethylene lost when the reactor is vented after completion of the reaction. Especially favorable yields can realized by: controlling the relative rates of isobutylene and sulfuric acid addition at an integration average isobutylene/acid molar ratio of between about 0.6 and about 0.75; controlling the overall weight ratio of organic solvent to sulfuric acid at less than about 0.5; adding sulfuric acid to the reactor over a 2 to 4 hour period in the ratio to isobutylene discussed elsewhere herein; and terminating or substantially reducing ethylene addition not later than 30 minutes after 95% of the sulfuric acid has been added.

In an alternative embodiment of the invention, it is possibly to omit introduction of solvent into the reactor, more particularly, without introducing solvent into the reaction zone from any extraneous source. In effect, neat isobutylene may provide a medium for absorption of ethylene, and vigorous agitation may be sufficient to maintain balanced ratios of isobutylene to ethylene at the acid interface. Since a degree of alkylation is essentially inevitable under most reaction conditions, a solvent phase may accumulate during the reaction regardless of whether solvent is initially introduced.

As indicated above, the pregnant liquor comprising the acid phase of the alkylation/esterification reaction mixture typically contains between about 20 and about 50 mole % of the sum of 3,3-dimethylbutyl hydrogen sulfate and di(3,3-dimethylbutyl) sulfate. As further indicated, minor amounts of various by-products may also be present. Of the mineral acid esters formed in the reaction, up to 50 mole %, typically 10 to 30 mole %, are diesters, the balance monoesters; and the overall ratio of 3,3-dimethylbutyl to ethyl residues among the esters may typically vary from about 50 to 1 to about 1 to 1. Additionally, on an organic basis, the pregnant liquor may typically contain between about 0 and about 10 mole % bis(3,3-dimethylbutyl)ether, and between about 0 and about 10 mole % diethyl ether. The $H_2SO_4$ acid content of the pregnant liquor is typically between about 25% and about 75% by weight, and the water content up to about 4% by weight, translating to an effective acid strength in the range of about 65% to about 33% by weight. The organic phase of the alkylation/esterification reaction mixture may contain various hydrocarbon by-products, including isobutylene dimer, olefinic oligomers and polymers, and "gasoline" range hydrocarbon alkylation products. At the end of the reaction, the reaction product mixture is removed from the reaction zone, and the acid and organic phases of the mixture are separated, conveniently by gravity.

Solvent is preferably be recycled if provision is made for purge of impurities and by-products. For example, all or a portion of the solvent phase may be consistently or periodically distilled or a solvent phase purge fraction removed from the process in a fractional amount effective to control recycled impurities and by-products at an acceptable level. If desired, prior to distillation the solvent phase may be contacted with an alkaline solution for removal and recovery of any residual 3,3-dimethylbutyl hydrogen sulfate, and di(3,3-dimethylbutyl) sulfate, and 3,3-dimethylbutyl ethyl sulfate from the organic phase.

Hydrolysis of the 3,3-dimethylbutyl esters is preferably carried out as soon as practical after conclusion of the alkylation/esterification reaction. The acid phase pregnant liquor is transferred to a hydrolysis reaction zone where it is contacted with water for hydrolysis of the 3,3-dimethylbutyl hydrogen sulfate, di(3,3-dimethylbutyl) sulfate, and 3,3-dimethylbutyl ethyl sulfate esters to 3,3-dimethylbutanol. Hydrolysis may be effected with or without addition of base by merely diluting the pregnant liquor with water and heating the diluted mixture. Generally, water may be added in a volume roughly equal to the volume of the liquor, or more generally in a volumetric ratio to the liquor of between about 0.5 and about 4, thereby providing a hydrolysis feed mixture containing between about 5% and about 70% by weight 3,3-dimethylbutyl sulfate, between about 0 and about 40% by weight di(3,3-dimethylbutyl) sulfate, between about 0% and 20% by weight 3,3-dimethylbutyl ethyl sulfate, between about 10% and about 60% by weight $H_2SO_4$, and between about 20% and about 65% by weight water, equating to a diluted sulfuric acid strength of between about 13% and about 75% by weight on an organic free basis, and a water to total mono and di 3,3-dimethylbutyl sulfate esters weight ratio of between about 15 and about 0.25. During water addition, the pregnant liquor is preferably maintained at a temperature not greater than 100° C., more preferably less than about 50° C., most preferably less than about 25° C., by removing heat of dilution to a refrigerant or refrigerated cooling fluid.

The diluted mixture is heated to a temperature of at least about 75° C., preferably between about 90° and about 120° C. for a period of between about 0.5 and about 12 hours, more preferably from about 1 to about 4 hours. A phase separation occurs as the hydrolysis proceeds, yielding a lower spent acid phase and an upper organic hydrolyzate phase containing the desired 3,3-dimethylbutanol product. The product may be recovered from the organic hydrolyzate phase by distillation or liquid/liquid extraction. It has been discovered that residual acid in the organic phase is detrimental in the distillation. In a batch process, it is preferred that this residual acid be neutralized by addition of a base, e.g., by washing the organic layer with a 0.05 to 2 N solution of alkali metal hydroxide or carbonate. Alternatively, an alkline earth oxide or hydroxide may be added to affect removal of excess acidity in the form of a solid precipitate such as gypsum or $MgSO_4$. Distillation of the organic phase is preferably conducted at reduced pressure, e.g., 50 to 200 torr and a pot temperature of between about 80° and about 150° C. Two major fractions are obtained, the first of which is predominantly organic solvent with only trace proportions of 3,3-dimethylbutanol. The second fraction is substantially 3,3-dimethylbutanol with no more than negligible concentration, of >$C_6$ alcohol by-products. Only a minor residue is retained in the distillation pot.

The spent acid phase of the hydrolysis reaction mixture may be purged from the process. Alternatively, it may be subjected to spent acid recovery processing as described below. Any residual 3,3-dimethylbutanol can be recovered from the acid phase by solvent extraction, and 3,3-dimethylbutanol thereafter recovered from the extract by distillation.

Although the hydrolysis step as described above is effective for the preparation of 3,3-dimethylbutanol, various undesired by-products may be formed during the hydrolysis, including, e.g., ethanol, bis(3,3-dimethylbutyl) ether, diethyl ether, and the mixed ether. Also, the hydrolysis is an equilibrium reaction which cannot proceed in the presence of a high concentration of alcohol. To minimize formation of undesirable by-products and obtain maximum yields of 3,3-dimethylbutanol, the hydrolysis is preferably effected by reactive distillation, in which the desired alcohol product is distilled from the reaction mixture as it is produced. A hydrolysis feed mixture for the reactive distillation is provided by water dilution of the acid phase pregnant liquor obtained in the alkylation/esterification reaction mixture, at dilution ratios generally in the same range as discussed above, but in any event sufficient for formation of an azeotrope of 3,3-dimethylbutanol and water. The head pressure is not critical but the distillation is preferably conducted either at atmospheric or reduced pressure in a range wherein an azeotrope of substantial 3,3-dimethylbutanol content is produced. Heating the hydrolysis feed mixture in the distillation pot or reboiler effects both hydrolysis of the 3,3-dimethylbutyl hydrogen sulfate, di(3,3-dimethylbutyl) sulfate, and 3-3-dimethylbutyl ethyl sulfate esters to 3,3-dimethylbutanol, and removal of the water/3,3-dimethylbutanol azeotrope as overhead vapor. In atmospheric distillation, light ends may be removed at temperatures below about 90° C., after which the 3,3-dimethylbutanol-rich azeotrope is distilled over at a temperature in the range of about 90° to 99° C. Although some rectification is desirable, only modest reflux and a few trays are indicated; and, if necessary, the azeotrope can be recovered by a straight takeover distillation.

When the distillation temperature approaches 100° C., the overhead vapor becomes essentially water only, and the distillation is terminated. The bottom product comprises the spent acid phase and a residual oil. Both may be discarded; or directed to a spent acid recovery operation. Recovered acid may be recycled to the alkylation/esterification reaction step. The oil phase may usefully serve as a source of fuel for spent acid combustion.

Upon condensation, the 3,3-dimethylbutanol-rich azeotrope fraction from the reactive distillation forms a two phase mixture, the upper layer of which comprises at least about 75%, ordinarily about 80 to about 90%, by weight 3,3-dimethylbutanol, and typically contains about 4 to 8% water, together with some ethanol, diethyl ether, and bis(3,3-dimethylbutyl) ether. The lower aqueous phase contains less than 2%, generally less than about 1%, by weight of the desired 3,3-dimethylbutanol product, together with some ethanol, and may be purged from the process. On an organics basis, the upper phase may comprise ≧90% by weight 3,3-dimethylbutanol with ≦10% by weight high boilers, i.e., >$C_6$ alcohols or residual esters. Consequently, without further refining, the upper phase may be used directly in the preparation of 3,3-dimethylbutanal. Alternatively, the upper phase may be subjected to further distillation, typically under vacuum, to improve the assay of the 3,3-dimethylbutanol intermediate product to greater than 98%, with a high boiler content ≦2%, by weight.

Reactive distillation produces 3,3-dimethylbutanol in molar yields greater than 50%, typically 70% to 90% based on the sum of esters and diesters of 3,3-dimethylbutanol in the pregnant liquor. Since hydrolysis of 3,3-dimethylbutanol esters releases mineral acid into the reaction mixture, thereby progressively increasing the mineral acid concentration, it may be desirable to add a base to the reaction mixture during the hydrolysis to neutralize excess acidity. This may be done by addition of a caustic or alkali metal carbonate solution to the reaction mass in response to measured increase in acidity. Optionally CaO, MgO, Ca(OH)$_2$ or Mg(OH)$_2$ may be added, thereby removing excess acidity by precipitation of the solid $CaSO_4$ or $MgSO_4$ salt.

Where the pregnant liquor obtained from the alkylation/esterification reaction is substantially neutralized with base before the reactive distillation, it is feasible to conduct the reactive distillation with a small proportion of water, sufficient only to effect the hydrolysis and generate the azeotrope. By condensation of the azeotrope, separation of the aqueous phase from the condensate, and reflux of the aqueous phase to the column, an inventory of water sufficient for both hydrolysis and azeotropic distillation is maintained. For example, instead of a dilution ratio of 0.5 to 2.0 as discussed hereinabove, the pregnant liquor may be diluted with water within a range of only about 0.1 about 0.5. Favorable results have been observed in conducting reactive distillation with water added in an intermediate ratio of about 0.3 to about 0.7 water/pregnant liquor. Substantial neutralization of the free acid prevents degradation of the product that might otherwise result from inadequate dilution.

Reactive distillation may be conducted in either a batch, semi-batch or continuous mode. In a continuous process, the pregnant liquor is continuously introduced into a distillation column comprising a hydrolysis reaction zone. Heat for the reaction and distillation of 3,3-dimethylbutanol is continuously supplied via a reboiler for the column. Bottoms are circulated through a reboiler to supply heat for the reaction and distillation. Spent acid is continuously withdrawn from the reaction zone and discharged from the bottom of the column, e.g., in response to a sump level controller, at a rate equivalent to the net production thereof. Overhead vapor is continuously removed and condensed for recovery of 3,3-dimethylbutanol. Light ends may be vented from the condenser scrubbed and/or flared. Condensate is separated into a 3,3-dimethylbutanol phase and aqueous phase in a continuous separator from which the 3,3-dimethylbutanol phase is continuously decanted and aqueous phase continuously drained. The aqueous phase drains to a reflux splitter where it is divided into a reflux stream and an forward flow stream.

In batch reactive distillation, the pregnant liquor is introduced into the distillation pot. Water may be charged at the start of the batch or introduced continuously or intermittently as the batch proceeds. The overhead condensate is allowed to separate and the aqueous phase is preferably refluxed to aid in the separation and promote the hydrolysis. If desired, fresh water can be introduced into top tray or other tray of the column. Alternatively, sulfate ester may be added to a vessel containing hot water and the 3,3-dimethylbutanol formed on hydrolysis distilled off as an azeotrope.

In an alternative embodiment of the invention, acid esters of 3,3-dimethylbutanol, e.g., bis(3,3-dimethylbutyl)sulfate or 3,3-dimethylbutyl hydrogen sulfate are hydrolyzed by contact with an aqueous solution or dispersion of a base such as NaOH, KOH, $Na_2CO_3$, $K_2CO_3$, CaO, MgO, Ca(OH)$_2$, or Mg(OH)$_2$. The base is supplied in excess of the amount required for to neutralize the free acid in the alkylation/esterification reaction mixture and the acid released in the hydrolysis so as to establish a pH sufficient to promote the hydrolysis.

Further in accordance with the invention, 3,3-dimethylbutanol may be converted to 3,3-dimethylbutanal by catalytic dehydrogenation. For example, a suitable catalyst for the dehydrogenation may be prepared, optionally in situ, by contacting 3,3-dimethylbutanol with a stoichiometric oxidation reagent comprising a metal oxide such as cupric oxide, cuprous oxide or a mixture of Cu(I) and Cu(II) oxides. Contacting the 3,3-dimethylbutanol with the metal oxide catalyst results in the desired conversion of 3,3-dimethylbutanol to 3,3-dimethylbutanal by oxidative dehydrogenation in a stoichiometric redox reaction which concomitantly reduces the metal oxide oxidizing agent to a reduced form comprising an active phase effective for the further anaerobic dehydrogenation of an alcohol to an aldehyde. Thereafter, with minimal if any interruption, contact of 3,3-dimethylbutanol with the catalyst can be continued for continuing production of 3,3-dimethylbutanal.

Other catalysts useful in the catalytic dehydrogenation include silver, gold, platinum, palladium, and a Pt/Sn alloy Cu/Zn. To extend the active surface area of the catalyst active phase, the catalyst may be supported on conventional catalyst carrier such as carbon, alumina, silica, mixtures of silica and alumina, titania, zirconia, zeolite, kieselguhr, baryte, controlled pore glass ("CPG"), etc. Co-ordination compounds of Ru, Cu, Pt or Pd may also be effective.

Essentially any catalyst effective for the dehydrogenation of alcohols to corresponding aldehydes may be used in the process. Such may include, for example, Cu—ZnO, Ag—Cu, ZnO, Co(II) molybdate, vanadium pentoxide, Ni, Ir, Ru, Re, Co, Zr, etc. Also see Augustine, "Heterogeneous Catalysts for the Synthetic Chemist," Marcel Dekker, Inc., 1996, pp. 430 to 472. Among the additional catalysts therein disclosed which may be useful in the dehydrogenation reaction are Raney Ni, Ni boride, $PtO_2$, Cu—CrO, Pd/C, Pd black, Pd/baryte, Ir/C, $FeCl_3$-doped Ru/C, Ru—Sn, Co boride, Co/alumina, Co—Zr/alumina, Raney Co, Ag—Fe, Ag—Zn, pre-reduced $Re_2O_7$, Pt/C, Pt/nylon, Re/CPG, Cu chromite, etc.

Where 3,3-dimethylbutanol is to be used as an intermediate for a pharmaceutical, or for a food product such as neotame, a catalyst is preferably selected which is substantially non-toxic. Catalysts which are effective for the reaction and substantially non-toxic include metallic copper, copper oxide and reduced copper oxide, as well as Ca—ZnO, Co, V, Ni, Ir, Ru, Re, etc. Chromium containing catalysts are preferably avoided.

The transitory stoichiometric oxidation reaction is exothermic, so appropriate provision must be made for removal of reaction heat. Preferably, the stoichiometric oxidation is conducted at a temperature in the range of between about 150° and about 350° C. Stoichiometric oxidation reaction may be conducted in a slurry reaction system in which the metal oxide catalyst is initially suspended in an agitated 3,3-dimethylbutanol reactant medium, optionally including a high boiling inert solvent such as bis(3,3-dimethylbutyl) ether, or vapor phase 3,3-dimethylbutanol may be passed over a fixed or fluid bed of metal oxide and therein converted to 3,3-dimethylbutanal. Since the function of this phase of the process is merely to prepare the catalyst, there is little if any criticality or importance to catalyst slurry concentration or alcohol in solvent concentration in a liquid phase system, or to the space velocity or other parameters of a fixed bed or fluid bed vapor phase system.

In a slurry reaction system for the dehydrogenation reaction of the invention, a particulate catalyst, such as metallic copper is slurried in a liquid dehydrogenation reaction medium comprising either neat 3,3-dimethylbutanol or a solution of 3,3-dimethylbutanol in an appropriate solvent, e.g., an ether such as diphenyl oxide. Particulate catalyst is slurried in the liquid reaction medium in a proportion of at least about 1% by weight, preferably between about 5% and about 20% by weight based on the 3,3-dimethylbutanol charge. The dehydrogenation reaction is conducted at a temperature of at least about 100° C., typically 100° C. to 400° C., preferably at least about 200° C., more preferably between about 275° and about 350° C., for a period sufficient for the reaction, typically in the range of 100 or more hours. Since the dehydrogenation reaction is endothermic, the temperature is preferably controlled at the desired level by introduction of heat by passage of steam or other heating medium through a jacket on the reactor or coils contained therein. The total pressure is preferably as low as feasible, more preferably not greater than about 100 psi (690 kPa) higher than the vapor pressure of the liquid reaction medium at the reaction temperature, more preferably not higher than 100 psig. An inert gas is preferably sparged into the reacting liquid to aid in displacing hydrogen therefrom. Hydrogen partial pressure is preferably below 100 psig. The presence of a minor proportion of water may be desirable to promote activity of the catalyst by facilitating the removal of reaction product from the active sites of the catalyst. The presence of water may also marginally improve the selectivity of the reaction for 3,3-dimethylbutanal. After the reaction is completed, the catalyst is separated from the reaction mixture by filtration, and the 3,3-dimethylbutanal product stripped from the solvent. Catalyst recovered by filtration may be recycled for use in subsequent dehydrogenation batches.

A liquid phase dehydrogenation reaction may be operated in a reactive distillation mode for removal of product 3,3-dimethylbutanal. By removal of hydrogen and product aldehyde from the reaction mixture, reactive distillation is effective to drive the equilibrium reaction forward. Although reactive distillation can provide for effective removal of the product 3,3-dimethylbutanal, a relatively high total pressure should be maintained to minimize stripping of 3,3-dimethylbutanol. Lower pressures can be tolerated but require condensation of 3,3-dimethylbutanol from the exit hydrogen stream and reflux to the reactor, thereby increasing the heat demands of the endothermic reaction system.

Although a liquid phase, slurried catalyst dehydrogenation reaction is effective for preparation of 3,3-dimethylbutanal, it is preferred that the reaction be conducted in vapor phase over a fixed or fluid catalyst bed comprising a tabular or particulate dehydrogenation catalyst. In the preferred dehydrogenation process, a feed stream is provided comprising at least about 0.5% by volume 3,3-dimethylbutanol, preferably between about 1% and about 25% by volume, more preferably about 2.5% to about 10% by volume in a carrier gas such as helium, nitrogen, carbon dioxide, steam, or mixtures thereof. Optionally, the feed gas diluent may consist solely or predominantly of steam. It is feasible for the concentrations of 3,3-dimethylbutanol to be higher than specified above, but relatively high temperatures are required to establish a favorable reaction equilibrium, as a result of which conversions at high concentration are limited by endothermic cooling. To an extent, it is possible to compensate for endothermic cooling by introducing the feed stream into the reactor at even higher temperatures than required for favorable equilibria, e.g., 500° C., in which instance it may be feasible to operate the reactor adiabatically. However, high feed gas temperature may cause sintering or other adverse effects on the catalyst. However, introduction of the feed gas at a temperature near the upper end of the preferred 250° to 375° C. operating range is desirable in any case to maintain the temperature in that range through a maximum portion of the reaction zone. The inert gas serves as a heat ballast helping to maintain the desired temperature. The dehydrogenation feed stream is passed through a dehydrogenation reaction zone comprising a fixed or fluid bed containing catalyst bodies having an active phase comprising a dehydrogenation catalyst. The vapor phase is preferably substantially free of molecular oxygen. The reaction is preferably conducted at a temperature of at least about 200° C., more preferably in the range of between about 250° and about 375°, most preferably between about 275° to 345° C. Temperatures in the upper portion of the latter range, e.g., 305° to 330° C. provide more favorable equilbria, but temperatures in the lower end of the range, e.g., 275° to 295° preserve catalyst activity over a longer catalyst life. To depress formation of ether and olefin by-products, it may be desirable to include steam in the feed gas to the dehydrogenation reactor. Relatively high temperatures within these ranges provide a higher equilibrium constant for the reversible dehydrogenation, and thus favor high conversions to 3,3-dimethylbutanal. The total pressure is maintained at no greater than about 100 psig (690 kPa), preferably between about 0 psig (0 kPa) and about 25 psig (170 kPa), and the hydrogen partial pressure is maintained at less than about 100 psig (690 kPa), preferably between about 5 psig (35 kPa) and about 20 psig (140 kPa). Both reaction equilibrium and selectivity become more favorable as the pressure decreases, but it is generally preferred to operate at least at atmospheric pressure to minimize velocity and pressure drop in the catalyst bed, and to prevent air from leaking into the hydrogen-containing reaction product stream.

Preferably, the catalyst bodies comprise a metal oxide active phase on an inert support.

The reactor is operated at a space velocity of at least about 0.25 sec$^{-}$, preferably between about 0.5 and about 2 sec$^{-1}$ and a linear velocity of about 0.2 to about 5 ft./sec., preferably about 0.8 to about 2.5 ft./sec. The activity and selectivity of preferred catalysts are sufficient so that the volume of the catalyst bed can be sized for a single pass conversion to 3,3-dimethylbutanal of at least about 50%, preferably between about 80% and about 100%. Residence time required for such conversion within the above noted range of space velocities is only about 0.1 to about 10 seconds. Typically the reaction gas exiting the dehydrogenation reaction zone contains between about 50 and about 98% by volume 3,3-dimethylbutanal and between about 50 and about 2% by volume 3,3-dimethylbutanol, in a ratio of at least about 1, more typically between about 4 and about 49 moles 3,3-dimethylbutanal to moles 3,3-dimethylbutanol. Where a metallic copper or other preferred catalyst is used, conversions greater than 50% may be maintained in sustained operations of over 30 days without regeneration of the catalyst.

Although the activity of preferred catalysts is sufficient to achieve substantially quantitative conversion in a very short residence time, a non-linear relationship has been discovered between the catalyst charge and the rate of catalyst deactivation. A catalyst charge just sufficient to provide equilibrium conversion in the first few hours of operation has been observed to deactivate rather rapidly beginning almost immediately after startup. However, a catalyst charge that is significantly larger than the minimum required to achieve equilibrium deactivates much more slowly, so as to extend catalyst life disproportionately to the additional charge of catalyst. As described in further detail in the working examples set out below, this observation translates into a most preferred space velocity toward the low end of the preferred range described above, i.e., below 2.0 sec$^{-1}$, e.g., from about 1.0 to about 1.5 sec$^{-1}$. Since catalyst performance relates primarily to the flow of 3,3-dimethylbutanol rather than total flow, the total flow rate through the reactor is determined primarily by competing considerations of temperature control and pressure drop; but in any case the product of space velocity and the volume fraction of 3,3-dimethylbutanol in the feed gas is most preferably controlled in the range of about 0.05 to about 0.08 (cc alcohol)(cc feed gas-sec)$^{-1}$.

While high catalyst loading provides exceptional benefits in catalyst life, it can also result in relatively poor selectivity during the reactor startup phase. It has been discovered that early selectivity can be improved by initial operating at relatively low temperature, e.g. 240° to 270° C. during a catalyst phase in period, and thereafter operating at a desired value for optimal conversion, preferably between 275° C. and about 345° C. The phase in period is long enough so that a yield of 3,3-dimethylbutanol of at least 85%, preferably at least about 88%, more preferably at least about 90%, is achievable from about 90 minutes after the beginning of the phase in period until a turnover ratio of at least 5 moles 3,3-dimethylbutanal per mole catalyst active phase has been realized. Typically, the requisite phase in period is one to four hours. Once any transient effect of startup has been traversed, the selectivity can be slightly better at higher vs. lower catalyst loading.

As noted, the anaerobic dehydrogenation reaction is endothermic. Thus, it is necessary or desirable to dilute the alcohol reactant substantially with an inert gas, as described hereinabove. The inert gas serves both: as a heat source, which minimizes temperature drop across the reactor, so that the equilibrium coefficient deteriorates as little as possible from reactor inlet to reactor exit; and as a diluent, which enhances equilibrium conversion at a given reaction temperature. It may further be desirable to introduce supplementary heat into the reaction system, either by surface heat transfer or by reheating the gas through introduction of hot diluent gases at discrete points along the route of passage of reacting gases through the catalytic dehydrogenation zone. For example, the reaction can be conducted over a fixed bed that is arranged in a plurality of stages in series and contained in a reaction vessel having a chamber substantially free of catalyst between a successive pair of said stages with respect to the passage of reaction gas through the reactor. A supply of heated gas is provided to the interstage chamber for reheating reaction gas entering said chamber from the stage immediately upstream of the chamber. Typically, the reactor may contains two or more catalyst stages and a plurality of such interstage chambers that are substantially free of catalyst, each of said chambers being located between a successive pair of catalyst stages. A supply of heated inert gas may be provided to each of the plurality of interstage chambers for reheating reaction gas entering such chamber from the stage immediately upstream thereof. Alternatively, the feed gas is heated to a temperature sufficient so that the reaction can proceed to the above indicated conversions under adiabatic conditions.

Alternatively, the dehydrogenation catalyst may be packed in the tubes of a shell and tube heat exchanger. A feed gas having the composition described hereinabove may be preheated in any convenient manner to a temperature effective for the dehydrogenation. A heat transfer fluid, e.g., molten salt bath is passed through the shell side of the exchanger to supply heat for the reaction and maintain the gas temperature in a range within which the reaction equilibrium is reasonably favorable, e.g., 200° C. to 400° C. Per a further alternative, the reaction tube(s) can be immersed in a sand bath that is in turn directly heated by contact with a flue gas that is produced by burning a hydrocarbon fuel or by electrical heating. In a still further alternative, flue gas may be injected into the process gas stream at points spaced along the reaction flow path to maintain the reaction gases at the desired temperature. As noted, adiabatic operation is another option, but conversions are limited by the effect of endothermic cooling on the terminal reaction temperature, even at feed gas temperatures so high that they may cause damage to the catalyst in the upstream portion of the bed.

The dehydrogenation reaction product gas is cooled to condense 3,3-dimethylbutanal product and any unreacted 3,3-dimethylbutanol therefrom. Refrigeration to a temperature of about −25° C. to about 0° C., preferably about −18° C. to about −8° C., is desirable to obtain recovery of 3,3-dimethylbutanal in good yield. Optionally, the product gas may be compressed, e.g., to between about 10 and about 1000 psig, to allow condensation at higher temperature. The condensate may then be or distilled for separation of the product 3,3-dimethylbutanal from the intermediate 3,3-dimethylbutanol. According to a further option, the reaction product gas may be passed through a partial condenser for removal of 3,3-dimethylbutanol, followed by a total condenser. Condensate from either or both condensers is then distilled to refine the 3,3-dimethylbutanal product. Distillation for refining of 3,3-dimethylbutanal can be conducted in either a batch or continuous mode. A 98% assay 3,3-dimethylbutanal fraction may be obtained.

Although purification of the reaction product condensate may be desirable in some instances, it is not generally necessary. Unlike the product of various prior art processes for the preparation of 3,3-dimethylbutanal, aldehyde produced in accordance with the process of this invention, as described hereinabove, is substantially free of impurities that create significant adverse effects in the reductive alkylation reaction for the synthesis of Neotame. More particularly, on an organics basis, the condensate contains less than 1% by weight of the corresponding acid (t-butylacetic acid). Where 3,3-dimethylbutanal is produced by stoichiometric oxidation in the presence of a free radical oxidizing agent, purification of the reaction product by distillation encounters formation of both an alcohol water azeotrope and an aldehyde/water azeotrope, each of which is also difficult to remove. By obviating the need for purification, the process of the present invention avoids the need for resolving these azeotropes.

According to a still further alternative, the reaction gas exiting the dehydrogenation reactor may be contacted with an absorbent for 3,3-dimethylbutanal. For example, the gas may be passed countercurrently to a liquid absorbent stream in an absorber e.g. a tower containing means such as rings, saddles or other packing material for promoting mass transfer of 3,3-dimethylbutanal from the gas to the liquid phase. A solution of 3,3-dimethylbutanal in the absorbent exits the bottom of the tower. Absorbents useful in this embodiment of the invention include organic solvents such as methanol, ethyl acetate, tetrahydrofuran, or methyl isobutyl ketone. 3,3-Dimethylbutanal may stripped from the rich absorbent stream, e.g., under vacuum or by introduction of live steam. Alternatively, the organic solution of the aldehyde may be introduced as such into a process for the manufacture of neotame or other product for which 3,3-dimethylbutanal may serve as an intermediate.

In a still further alternative embodiment, 3,3-dimethylbutanal and any unreacted 3,3-dimethylbutanol may be condensed from the dehydrogenation reaction gas stream by quenching in water, for example, by causing the gas stream to flow countercurrently to an aqueous quenching stream in a packed or tray tower, or by introducing the gas below the surface of an aqueous quenching bath. Thereafter 3,3-dimethylbutanal is allowed to separate from the aqueous quenching medium; and organic product phase may then be purified by crystallization or distillation, or used directly in the manufacture of Neotame.

In the process of the invention it has been found that catalysts for the dehydrogenation of 3,3-dimethylbutanol remain highly active over runs which extend well beyond those reported in the prior art. Productivity and yields remain substantially stable over such extended periods of operation. Turnover ratios of 5, 10, 15 or more moles 3,3-dimethylbutanal per mole catalyst active phase are readily achieved without interruption of the reaction for regeneration of the catalyst. Moreover, each such turnover ratio may be realized at a yield of 3,3-dimethylbutanal which is at least 80%, more typically 90%, 95% or 98% of the initial or maximum yield achieved during the course of a catalyst run. "Turnover" as referred to herein means moles product produced per total moles of the active phase of the catalyst, without reference to the actual number or density of active sites in the active phase. In the case of a catalyst structure having more than one phase, e.g., a metal or metal oxide catalyst on an inert support, "catalyst active phase" means only the phase containing the active sites at which the reaction is conducted or initiated.

Where an anaerobic dehydrogenation is conducted at a site where hydrogen may be used in the reduction of a hydrogen acceptor, it may be feasible to conduct the dehydrogenation in the presence of the hydrogen acceptor, thereby making effective use of the hydrogen, possibly in situ, and potentially driving the equilibrium reaction in the desired direction under conditions that might not otherwise be conducive to the purpose, e.g., at relatively low temperature, high 3,3-dimethylbutanol concentration, or high pressure. For example, it may be feasible to drive the reaction quantitatively at a temperature in the range of 200° to 250° C. and/or at 3,3-dimethylbutanol concentrations in excess of 50 mole %. If the 3,3-dimethylbutanol to 3,3-dimethylbutanal conversion takes place entirely in the liquid phase, the reaction may be promoted by the presence of a gas phase which functions as a hydrogen acceptor, or vice versa. Typical hydrogen acceptors include ketones, aldehydes (other than the desired product), or olefins.

Although 3,3-dimethylbutanol is preferably converted to 3,3-dimethylbutanal by anaerobic dehydrogenation as described above, other methods may be employed for this conversion. For example, the reaction can be carried out by aerobic dehydrogenation according to process schemes comparable to those discussed above for anaerobic dehydrogenation. Oxidative dehydrogenation is an exothermic reaction which proceeds irreversibly. In accordance with this alternative process, a vapor phase mixture of 3,3-dimethylbutanol and an oxygen-containing gas can be passed over a fixed or fluid catalyst bed, or an oxygen-containing gas can be introduced into a slurry of catalyst in a liquid phase comprising 3,3-dimethylbutanol. In a vapor phase reaction system, the feed gas preferably contains oxygen in a proportion between about 1% and about 20%, preferably between about 5% and about 10%, by volume, and 3,3-dimethylbutanol in a proportion of between about 5% and about 10% by volume. In the aerobic process, dehydrogenation is effected oxidatively, forming water rather than hydrogen as a by-product of the reaction. Catalysts useful in oxidative dehydrogenation include metal oxides such as copper oxide, zinc oxide or a copper oxide/zinc oxide mixture. In oxidative dehydrogenation, the metal oxide is believed to participate in a redox reaction with the 3,3-dimethylbutanol substrate, forming 3,3-dimethylbutanal and water with concomitant reduction of the metal oxide to a metallic or other reduced state, as in the stoichiometric reaction as described above. Reoxidation with oxygen from the gas stream restores the activity of the catalyst for the oxidative dehydrogenation. In this manner, the aerobic catalytic process differs from the stoichiometric process in which the oxidizing agent is consumed in the reaction and, if regenerated at all, is regenerated off-line. Oxidative dehydrogenation is a highly exothermic reaction that is preferably conducted at a temperature of between about 150° about 250° C., i.e., somewhat lower than the optimal temperature for anaerobic dehydrogenation. Because of a tendency for over-oxidation to 3,3-dimethylbutanoic acid, oxidative dehydrogenation may not provide the yields afforded by the anaerobic process. On the other hand, the exothermic nature of the reaction not only allows the aerobic process to be run at relatively lower temperature, but also at higher 3,3-dimethylbutanol concentration, in excess of 50 mole %, without adverse equilibrium effects.

Advantageously, the oxidative reaction may be carried out in a tubular reaction system comprising the tubes of a shell and tube heat exchanger. Feed gas comprising 3,3-dimethylbutanol and oxygen is introduced into the tubes, which are packed with an appropriate catalyst for the reaction. A heating fluid such as molten salt is circulated through the shell side of the heat exchanger for removal of the heat of the reaction. Alternatively, the temperature of the reaction gases may be maintained in accordance with any of the various stratagems described above for anaerobic dehydrogenation. Thus, the reaction system is comparable to one of the alternative systems described above for anaerobic dehydrogenation, but the molten salt bath or fluidized sand bath serves as a cooling rather than heating medium. 3,3-Dimethylbutanal is recovered from the reaction gas by condensation or absorption as described above. Optionally, the reaction gas may be compressed prior to condensation or absorption. Separation of the desired 3,3-dimethylbutanal product is obtained by distillation of condensate or stripping from rich absorbent solution, as further described hereinabove.

In still further alternative embodiments of the overall process of the invention, 3,3-dimethylbutanol is produced initially by either reduction of 3,3-dimethylbutanoic acid according to the procedure described in *J. Org. Chem.*, Vol. 46, 1981, pp. 2579–2581 for the preparation of ethanol and phenylethanol, by hydrolysis of a 1-halo-3,3-dimethylbutane as described in *J. Am. Chem. Soc.*, Vol. 73, p. 555, or by conversion of the epoxide to the alcohol per the method described in Neftelehimiyn, 19, pp. 762–766 (1979). In the reduction of 3,3-dimethylbutanoic acid, an alkali metal borohydride serves as a preferred reducing agent. Alternatively, 3,3-dimethylbutanoic acid may be reduced to 3,3-dimethylbutanol by catalytic hydrogenation.

3,3-Dimethylbutanoic acid may be prepared in accordance with the method described in *Synthesis*, 1985, pp. 493 to 495 wherein vinylidene chloride is reacted with t-butanol in sulfuric acid, followed by hydrolysis. Alcoholysis produces an ester of the alcohol and 3,3-dimethylbutanoic acid, which may be reduced to 3,3-dimethylbutanol. The fatty alcohol may be produced from the ester by hydrogenation under high pressure and temperature. See "Oils and Fats Manual," Lavoisier Publishing, 1996, pp. 1083 to 1084. Hydrogenation of the acid is an attractive route to 3,3-dimethylbutanol because it is typically highly efficient and does not necessarily require a solvent. Non-catalytic reducing agents for 3,3-dimethylbutanoic acid include Li Al hydride and Na borohydride.

Hydrolysis of 1-halo-3,3-dimethylbutane may be carried out in the presence of base at a temperature greater than about 200° C., preferably between about 200° to about 250° C. A moderately strong base such as an alkali metal carbonate is effective for the reaction, but tends to generate very high pressure due to the release of carbon dioxide. Preferably, therefore, a Group II metal oxide such as zinc oxide may be used to promote the hydrolysis. Alternatively, an alkali metal salt of an organic acid may be used, e.g., K acetate, thereby producing an ester of 3,3-dimethylbutanol and the acid, which may be hydrolyzed to 3,3-dimethylbutanol in the presence of a strong base such as NaOH or KOH.

According to a further alternative, 1,2-epoxy-3,3-dimethylbutane may be formed by epoxidation of 3,3-dimethylbutene, with an alkali metal hypohalite, such as Na hypochlorite or dimethyldioxirane. Hydrogenation of the epoxide in the presence of a platinum metal or transition metal catalyst, e.g., Pt, Pd or Ni, yields a mixture of 3,3-dimethylbutanol and 3,3-dimethyl-2-butanol, under optimal conditions in an 8:2 ratio. In conducting the hydrogenation, a solution of 1,2-epoxy-3,3-dimethyltbutane is charged to an autoclave in a solvent such as an alkane such as hexane or heptane, a lower alcohol such as methanol or ethanol, an ester such as methyl or ethyl acetate or an ether such as tetrahydrofuran. A catalyst such as Raney Ni, in a proportion of about 0.5 g to about 1 g/mL 3,3-dimethylbutene oxide, or Pd/C, in a proportion of about 0.001 to about 0.1 g Pd/mL 3,3-dimethylbutene oxide, is slurried in the charge solution. Reaction is carried out under vigorous agitation at a temperature of between about 50° and about 200° C., preferably between about 90° and about 160° C., and a hydrogen pressure of between about 50 and about 3000 psig, preferably between about 100 and about 1000 psig.

In a further method, an organometallic reagent such as a t-butyl Grignard reagent or t-butyl lithium is reacted with ethylene epoxide at low temperature to yield 3,3-dimethylbutanol. Preferably, the reaction is conducted in a solvent for the reactants such as diethyl ether, pentane, heptane, t-butyl methyl ether, toluene or tetrahydrofuran. Because organometallic reagents are sensitive to moisture and oxygen, the reaction is carried out under an inert atmosphere, e.g., helium, argon or nitrogen. The reaction should be carried out at low temperature, e.g., in the range of between about −100° and about −50° C. After an appropriate reaction period, e.g., 30 minutes to 3 hours, the reaction solution is allowed to warm to room temperature and quenched with a mineral acid such as sulfuric acid. The aqueous and organic phases are then separated, and the aqueous layer extracted with solvent for recovery of residual alcohol product. The combined organic layers may then be washed with water and dried with a desiccant such as $MgSO_4$. The solvent is removed and the residue distilled to yield the 3,3-dimethylbutanol product.

While all of the above described methods for the preparation of 3,3-dimethylbutanol may be used in the processes of the invention for preparation of 3,3-dimethylbutanal and Neotame, 3,3-dimethylbutanol is preferably prepared by an alkylation/esterification reaction of ethylene, isobutylene and a mineral acid, as described in detail above.

As noted, 3,3-dimethylbutanal is useful as an intermediate in the preparation of neotame. As described in U.S. Pat. No. 5,728,862, expressly incorporated herein by reference, N-[N-(3,3-dimethylbutyl)-L-α-aspartyl]-L-phenylalanine 1-methyl ester may be prepared by treating a mixture of aspartame and 3,3-dimethylbutanal in an organic solvent with hydrogen in the presence of a hydrogenation catalyst at a temperature and pressure effective to form the desired product. Alternatively, 3,3-dimethylbutanal may be added to a mixture of aspartame and sodium cyanoborohydride as described in U.S. Pat. No. 5,480,668, also expressly incorporated herein by reference.

Figure 7:
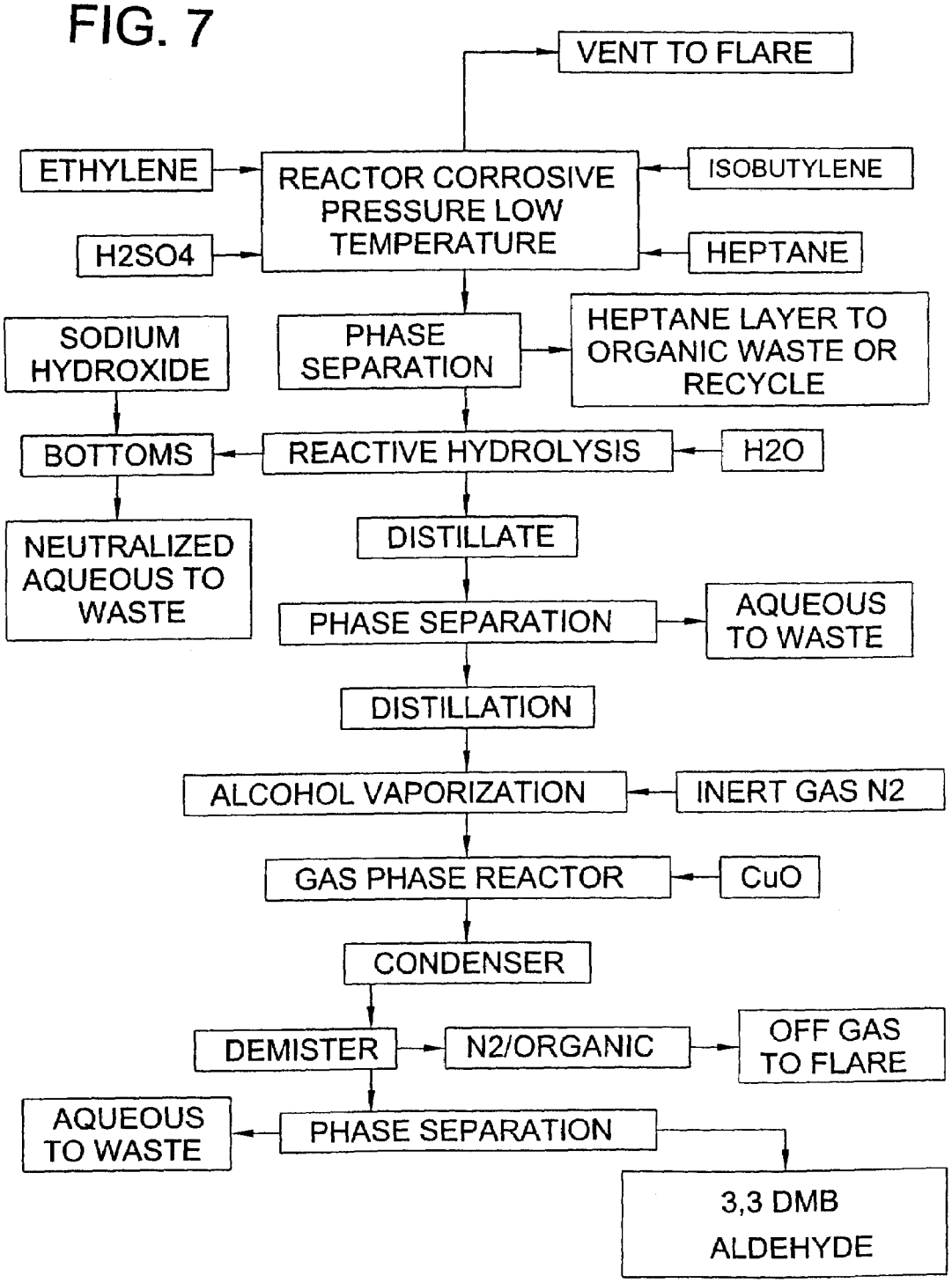
FIG. 7 is a block flow diagram of the overall process of the invention for the preparation of 3,3-dimethylbutanal.
Figure 8:
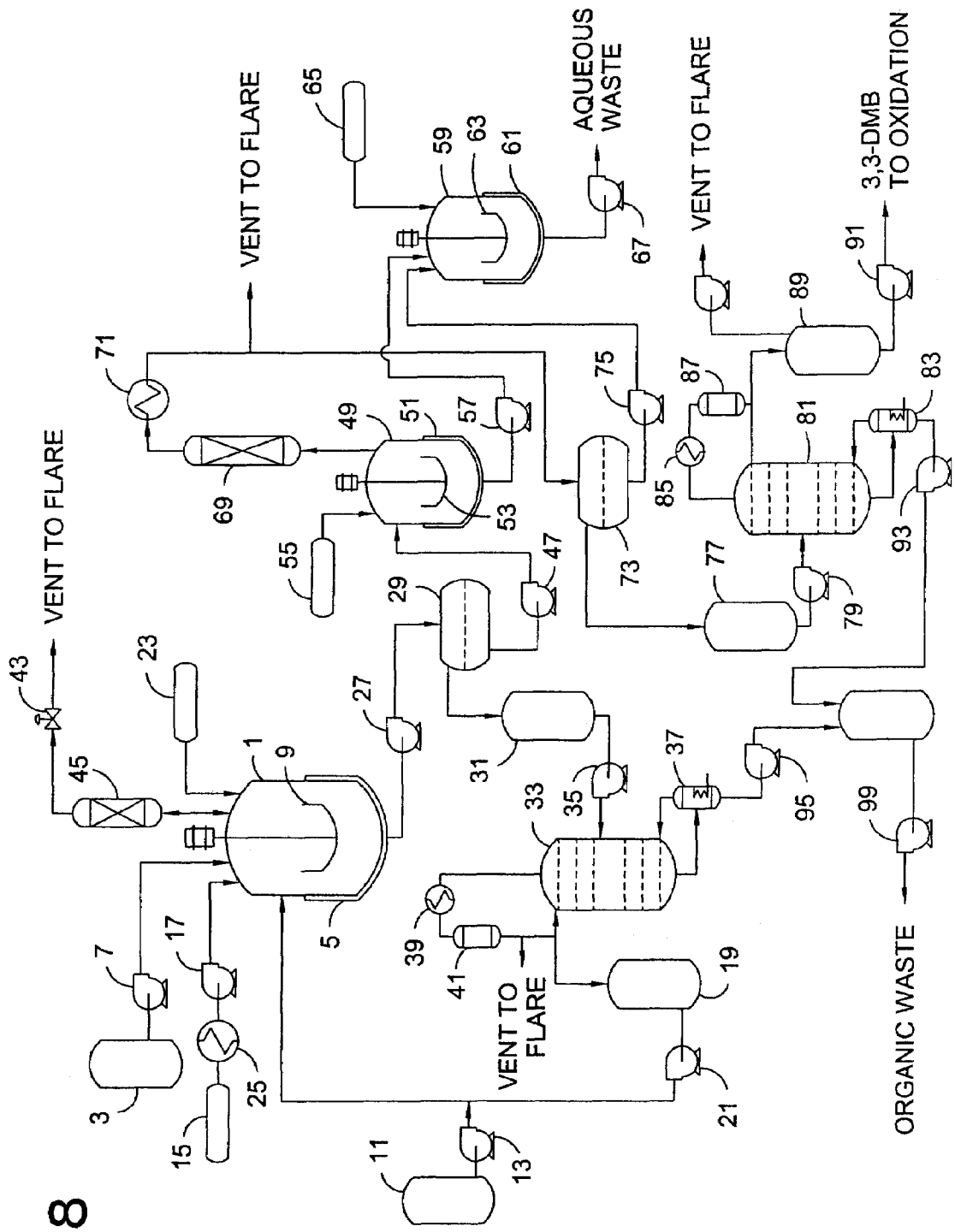
FIG. 8 is a process equipment diagram and flow sheet for an embodiment of the overall process of the invention for the continuous preparation 3,3-dimethylbutanol.

Particular embodiments of the overall process for producing 3,3-dimethylbutanal are illustrated in FIGS. 7 and 8. Referring to the block diagram of FIG. 7 and, more particularly, to the equipment items referenced on the flowsheet of FIG. 8, sulfuric acid is transferred from a supply tank 3 by a transfer pump 7 to an alkylation/esterification reactor 1. Reactor 1 is provided with a cooling jacket 5 and an agitator 9. Isobutylene is transferred from a supply tank 15 through a condenser 25 which is chilled by heat transfer to a refrigerated brine solution, and by an isobutylene transfer pump 17 to reactor 1. Heptane is supplied to reactor 1 from a recovered heptane tank 19 via a heptane transfer pump 21. Additional makeup heptane, as needed, is supplied to the reactor from a heptane storage tank 11 via a heptane transfer pump 13. Ethylene from a source 23 is introduced into the head space of reactor 1 at a pressure effective for the reaction, as described hereinabove. Optionally, ethylene can be sparged below the surface of the mixture of condensed phases, i.e., acid and heptane.

In reactor 1, sulfuric acid, ethylene and isobutylene are reacted under intense agitation to form a reaction mixture comprising a pregnant liquor comprising 3,3-dimethylbutyl hydrogen sulfate, di(3,3-dimethylbutyl) sulfate, and 3,3-dimethylbutyl ethyl sulfate in sulfuric acid, and an organic phase comprising heptane and alkylation by-products. The reactor may be operated in either batch or continuous mode. The flowsheet of FIG. 8 is adapted for operation as a batch or semi-continuous reactor in which the heptane is initially charged to the reactor with all or a portion of the sulfuric acid. Ethylene pressure is controlled at a constant value by a pressure regulator 43 in a vent line from reactor 1, and isobutylene liquid is metered into the reactor, along with the remainder of the sulfuric acid if the all the acid has not been initially charged to the reactor. Alternatively, reactor 1 may be operated as a continuous stirred tank reactor into which sulfuric acid and a heptane solution of isobutylene are continuously or intermittently introduced under a constant pressure of ethylene, and from which the alkylation/esterification reaction mixture continuously or intermittently withdrawn. A gas separator 45 can be used to minimize liquid entrainment. If desired, the vented gas can be collected, compressed and recycled. Ethylene pressure may be controlled, e.g., by use of a variable speed compressor or by a pressure regulator between source 23 and reactor 1.

Degassed alkylation/esterification reaction mixture withdrawn from reactor 1 is transferred via a pump 27 to a liquid/liquid separator 29. The upper organic phase is removed from separator 29, flows into a feed tank 31 and is thence transferred to a heptane recovery distillation column 33 via a column feed pump 35. The heptane recovery system is designed such that the distillation operation can be operated in batch or continuous mode. FIG. 8 illustrates a column with three rectification trays and three stripping trays. Heat is supplied via a reboiler 37, and overheads are condensed in a condenser 39, flowing to a condensate drum 41 and a reflux splitter (not shown). The column is operated at a reflux convenient to the separation and the remainder of the overhead condensate flows to a recovered heptane receiver 19. Recovered heptane is recycled via a heptane recycle pump 21 to reactor 1.

Pregnant liquor drawn from the bottom of separator 29 is transferred via a pump 47 to a hydrolysis reactor 49 which is provided with a heating jacket 51 and an agitator 53. Deionized water is introduced into reactor 49 from a water head tank 55. Water reacts with the sulfate esters of 3,3-dimethylbutanol to produce 3,3-dimethylbutanol which is distilled out of the hydrolysis reaction mixture by heat supplied from jacket 51. Spent acid is withdrawn from the bottom of reactor 49 and transferred via a spent acid pump 57 to a neutralization reactor 59 which is also provided with a jacket 61 and an agitator 63. Caustic soda is added from a head tank 65 to neutralization reactor 59 to neutralize the spent acid. The resultant neutral salt solution is sent to aqueous waste by waste pump 67. The salt solution can be further diluted with water, if desired.

Overhead vapor from the reactive distillation reactor is passed through a packed fractionation column 69 operating on internal reflux only. Vapor exiting the top of column 69 is condensed in an alcohol condenser 71, and the condensate flows to a receiver/separator 73. The aqueous phase which contains less than 1% by weight 3,3-dimethylbutanol is drawn off the bottom of separator 73, and is transferred via a pump 75 to neutralization reactor 59 for ultimate disposal. The upper phase, typically comprising about 80 to 90% by weight 3,3-dimethylbutanol and 4 to 8% by weight water, flows by gravity from separator 73 to a distillation feed tank 77, and thence via a column feed pump 79 to a distillation column 81 for isolation of 3,3-dimethylbutanol, obtained as a distillate from the column. As shown, column 81 comprises three rectification trays and three stripping trays. The distillation system further comprises a reboiler 83, an overheads condenser 85, a condensate drum 87 and a reflux splitter (not shown). The column is operated at a reflux convenient to the separation and the remainder of the overhead condensate flows to a 3,3-dimethylbutanol product receiver 89, whence it may be transferred by pump 91 to an oxidation or dehydrogenation reactor for conversion of 3,3-dimethylbutanol to 3,3-dimethylbutanal.

Bottoms from columns 81 and 33 are transferred via bottoms pumps 93 and 95 respectively to an organic waste tank 97. A pump 99 sends the collected bottoms to organic waste disposal and/or treatment.

As illustrated schematically in FIG. 7, the alcohol intermediate is vaporized in a nitrogen carrier gas and passed over a fixed dehydrogenation catalyst bed comprising a metallic Cu catalyst. Dehydrogenation reaction product gas is cooled to condense 3,3-dimethylbutanal product. The vapor phase exiting the condenser passes through a mist eliminator to collect entrained condensate which drains into a mist liquid receiver/separator. The aqueous phase from the separator is discharged to aqueous waste treatment and disposal. The organic phase comprises the 3,3-dimethylbutanal product. If a high level of alcohol is present in the organic phase, it may be recycled to the alcohol vaporization step upstream of the fixed bed dehydrogenation reactor. The gas phase passing through the mist eliminator is discharged to the atmosphere through a flare. The organic phase may be recycled as discussed above, or used in the synthesis of neotame, optionally after purification as a preliminary step in the neotame process.

Figure 9:
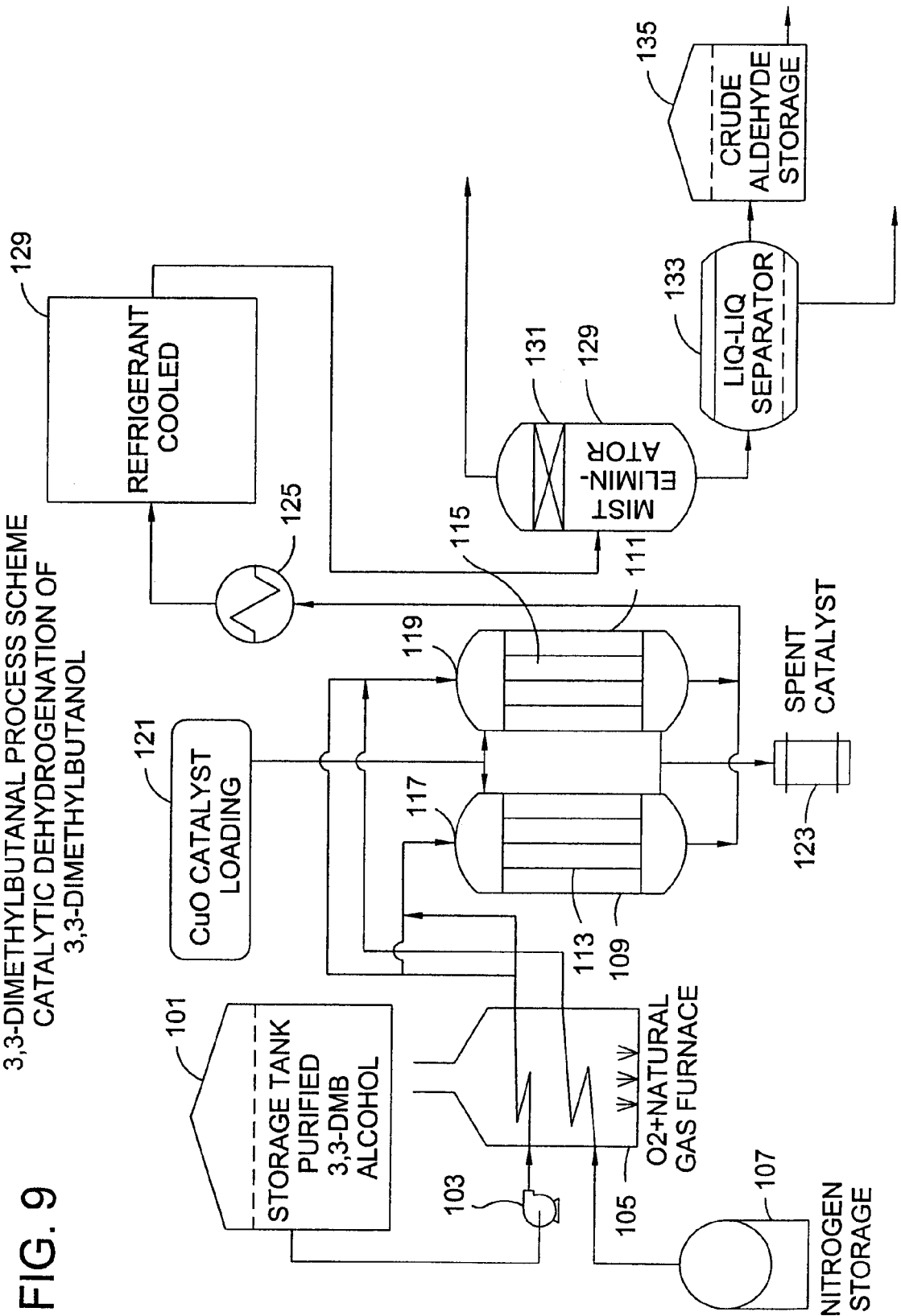
FIG. 9 is a process equipment diagram and flow sheet for an embodiment of the catalytic dehydrogenation of 3,3-dimethylbutanol to 3,3-dimethylbutanal.

FIG. 9 illustrates further detail of a preferred process of the invention for the continuous conversion of 3,3-dimethylbutanol to 3,3-dimethylbutanal. Liquid 3,3-dimethylbutanol containing 0.1% to about 7.0% by weight water is transferred continuously from an alcohol storage tank 101 by a pump 103 to a gas fired furnace 105 where it is vaporized. An inert diluent gas, preferably nitrogen, is transferred under autogenous pressure from a liquid nitrogen storage bottle 107 through furnace 105 where it is heated to a temperature between about 250° and about 400° C. Nitrogen and 3,3-dimethylbutanol vapor are mixed in-line to provide a dehydrogenation feed gas containing between about 0.1 mole % and about 10 mole % 3,3-dimethylbutanol. The feed gas is introduced continuously at a temperature between about 250° and about 400° C. and a total pressure of between atmospheric and about 30 psig into one of a pair of parallel tubular reactors 109 and 111 for dehydrogenation of 3,3-dimethylbutanol to 3,3-dimethylbutanal. Feed is switched between the two reactors so that only one is ordinarily in operation at any particular time, but at least one is in operation essentially at all times. Each of reactors 109 and 111 comprises a fixed catalyst bed, respectively designated 113 and 115. Each reactor is in the form of a shell and tube heat exchanger. Each tube is packed with catalyst and the catalyst in each tube thus comprises a component catalyst bed, the combination of the component catalyst beds constituting the fixed catalyst bed of the reactor. Gas is distributed among the tubes and flows through each tube over the component bed contained therein for dehydrogenation of 3,3-dimethylbutanol to 3,3-dimethylbutanal. The tubes are maintained at the desired reaction temperature by transfer of heat from a heat transfer medium, typically molten salt, that is circulated through the shell side of the exchanger.

The catalyst in tubes comprises a metallic copper catalyst supported on an inert support such as silica, alumina or mixtures thereof. The catalyst bodies of which catalyst beds 113 and 115 are comprised have an average principal dimension between about 0.5 and about 10 mm, preferably about 2 to about 5 mm, and a B.E.T. surface area between about 20 and about 100 m$^3$/g. During operation of reactor 109, the feed gas containing between about 5% and about 20% by volume 3,3-dimethylbutanol is introduced continuously into the reactor at a temperature between about 250° and about 375° C. and a total pressure of between about 10 and about 100 psig (69 to about 690 kPa) through an inlet 117 which is in fluid flow communication with 3,3-dimethylbutanol storage and nitrogen storage via the transfer lines passing through furnace 105. When the activity of the catalyst in bed 111 of reactor 109 has declined below a desired value, the feed gas is switched to inlet 119 of reactor 111 and reaction continued by passage of reacting gases over catalyst bed 115 while the activity of catalyst bed 113 is being restored by regeneration or replacement of the catalyst contained therein. Regeneration may be accomplished by circulation of heated air through the catalyst bed via a catalyst regeneration system of conventional configuration (not shown in the drawing). Operation of reactor 111 is carried out under essentially the same conditions as described for reactor 109. Thus, the two catalyst beds are alternated so that at any time one reactor is in reaction mode and the other in reactivation mode, and the dehydrogenation process may be conducted over an extended period of operation essentially without interruption. Catalyst is supplied from a source 121 and spent catalyst is discharged to a spent catalyst drum 123.

Conversion of 3,3-dimethylbutanol to 3,3-dimethylbutanal in reactor 107 or 109 is between about 50% and about 100%.

Reaction product gas is cooled in a water-cooled condenser 125 that is in fluid flow communication with the exit of reactor 109 or 111, and further cooled in a refrigerant cooled condenser 127 in communication with the exit of condenser 125. Mixed gas and liquid exiting condenser 127 is passed to a gas/liquid separator 129. The gas phase exiting the top of the separator passes through a mist eliminator 131 and thence to an off gas flare. Liquid exiting the bottom of separator 129 flows to a liquid/liquid separator 133, where the liquid separates into a lower aqueous phase containing not more than about 1% 3,3-dimethylbutanal and not more than about 6% 3,3-dimethylbutanol, and an upper organic phase comprising at least about 85%, preferably between about 89% and about 99%, by weight 3,3-dimethylbutanal, and not more than about 50%, preferably between about less than 1% and about 20%, by weight 3,3-dimethylbutanol. The 3,3-dimethylbutanal layer is transferred to a crude aldehyde storage tank 135 for use in a reductive alkylation reaction for the manufacture of Neotame. The aqueous layer is transferred to aqueous waste treatment and disposal.

If desired, the crude aldehyde layer obtained from separator 133 may be further processed in a conventional manner known to the art, e.g., by distillation, extraction, or crystallization, to obtain a 3,3-dimethylbutanal product of any desired quality or purity.

Figure 10:
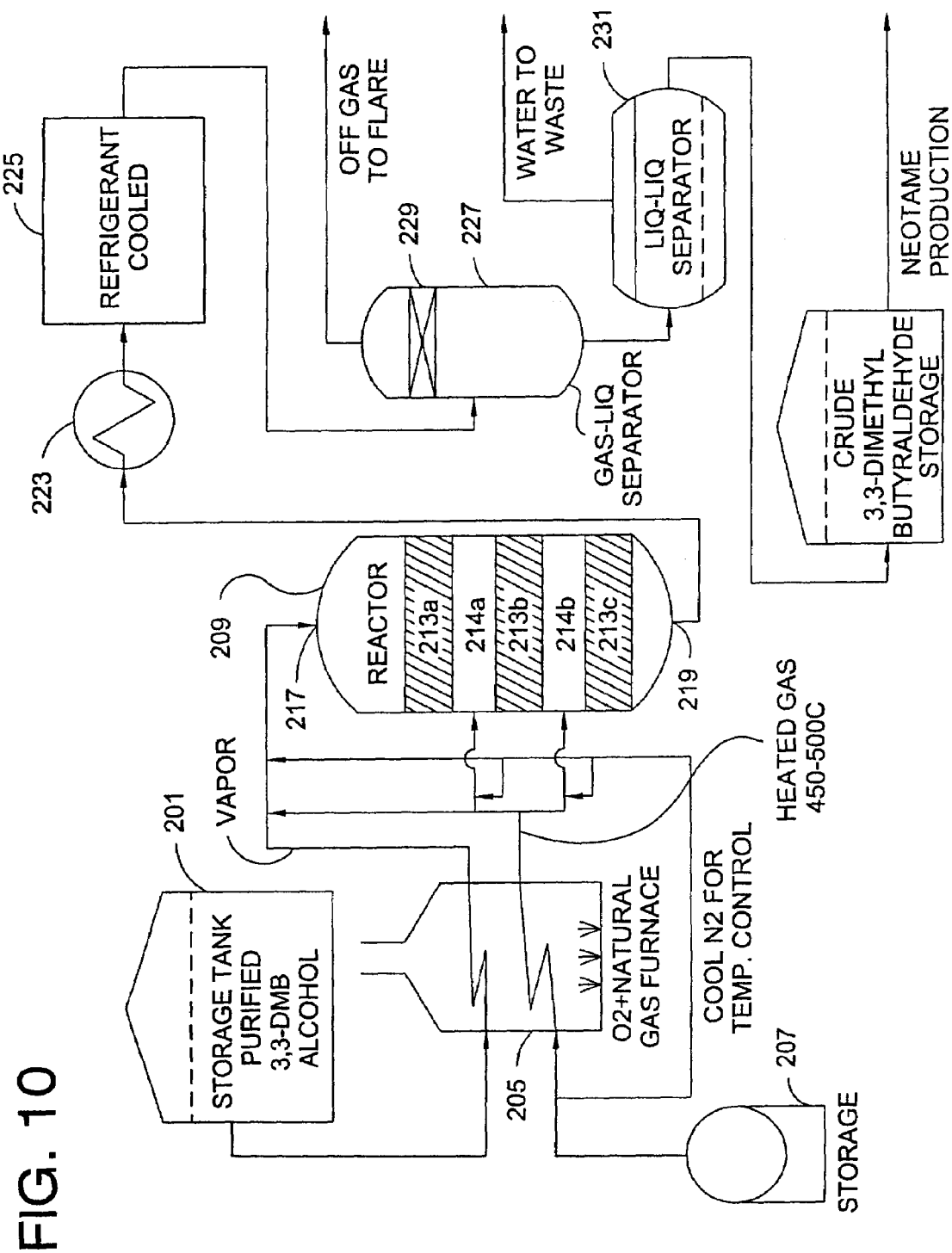
FIG. 10 is a process equipment diagram and flow sheet for an alternative embodiment of the catalytic dehydrogenation process.

An alternative embodiment of the process for dehydrogenation of 3,3-dimethylbutanol is illustrated in FIG. 10. Supply of alcohol from storage tank 201, supply of nitrogen from bottle 207, preheating of alcohol and nitrogen in furnace 205 and mixing of alcohol and nitrogen to provide a reactor feed mixture are carried out in a manner identical to that of the corresponding operations of the process of FIG. 9 as described hereinabove. The feed gas is introduced into dehydrogenation reactor 209 containing a fixed bed 213 comprising a catalyst of the type used in reactors 109 and 111 of FIG. 9. Fixed bed 213 is divided into three stages 213a, 213b, and 213c. Reaction gas flows downwardly through these stages from reactor inlet 217 to reactor outlet 219, effecting a significant initial conversion of 3,3-dimethylbutanol to 3,3-dimethylbutanal. Due to the endothermic nature of the reaction, the reaction gas temperature declines in its passage through each of stages 213a, 213b, and 213c. In order to restore the gas temperature entering each stage to a temperature within the desired range, heated inert gas is introduced into the reaction gas stream in a chamber 214a between catalyst stages 213a and 213b, and a chamber 214b between catalyst stages 213b and 213c. This is accomplished by dividing the nitrogen stream exiting furnace 205 into three streams, the first of which is mixed with 3,3-dimethylbutanol vapor upstream of inlet 217, the second of which is introduced into the chamber 214a, and third of which is introduced into chamber 214b. Chambers 214a and 214b may be void, or comprise inert packing.

To provide control of gas temperature entering each of the catalyst stages, cool nitrogen gas by-passed around furnace 205 may be injected into the dehydrogenation feed stream entering the reactor, or into the inert heating gas introduced between stages, in each instance at a rate regulated to control temperature in response to measurement made by sensors (not shown) at each of these points.

The remainder of the operation of the process of FIG. 10 is essentially identical to the operation of the corresponding portions of the process of FIG. 9.

In a further alternative embodiment, a single tube tubular reactor may be banded with electrical heaters to establish and maintain desired temperatures in a plurality of catalyst subregions longitudinally sequenced within the catalyst bed. In such a system, the catalyst bed may be diluted with inert packing to facilitate control of the reaction, control of temperature within each of the sequential subregion, and tailoring the reaction temperature to the composition of the reaction mixture as it flows from subregion to subregion. According to a still further alternative, a tubular reactor may be divided into a plurality of segments in series, with a sand bath positioned between each successive pair of segments for reheating the reacting gases exiting the upstream segment to a temperature appropriate for introduction into the downstream segment.

Beyond its utility in the preparation of [N-(3,3-dimethylbutyl)-L-α-aspartyl]-L-phenylalanine, 1-methyl ester, 3,3-dimethylbutanal is useful as an intermediate in the preparation of other sweetener products such as [N-(3,3-dimethylbutyl)-L-α-aspartyl-α-methyl-L-tyrosine 1-methyl ester (EP 0 866 073), aspartyl dipeptide amide derivatives (EP 0 818 463) and the aspartyl tripeptide derivatives (JP09278792), N-alkylaspartyl dipeptides (JP09227589), and other stable aspartylamide sweeteners (EP 0 784 050). It has further utility in the preparation of a wide variety of pharmaceutical products including, e.g., various substituted 2-pyranones useful as HIV protease inhibitors (U.S. Pat. No. 5,808,062), substituted peptides useful as calcium channel blockers (WO98/10838), urea derivatives useful as raf kinase inhibitors WO98/52559), aryl ureas useful as p38 kinase inhibitors (WO98/52558), and aminediol-containing peptide analogs as retroviral protease inhibitors (Frost et al., *Tetrahedron Letters*, 37(51), pp. 9139–9142), erythromycin derivatives (EP 0 614 905).

The following examples illustrate the invention.

EXAMPLE 1

Sulfuric acid (10 g; 98 mmol; 96% by weight) and heptane (10.2 mL) were charged to a glass liner. The glass liner was placed into a jacketed autoclave and the head attached. After the system was flushed with nitrogen, the charge mixture was cooled to −14° C. under agitation at 400 rpm. At this temperature, ethylene was introduced into the head space of the autoclave at a pressure of 120 psig, and this pressure was maintained throughout the course of the ensuing reaction. Once ethylene pressure had been applied, addition of isobutylene was commenced at a metered rate of 1 mL/hr (0.59 g/hr) while the reaction mixture was maintained at −14° to −16° C. by removal of heat to cooling fluid (ethylene glycol) in the jacket. Addition of isobutylene was terminated after four hours, during which the total amount of isobutylene added was 2.36 g (42 mmol). The autoclave was then vented to remove ethylene from the head space, with 0.31 g ethylene remaining in heptane solution after venting (solubility of ethylene in heptane at −14° C. and 40 psig is about 1.1 mol.=/L).

After ethylene was vented, the glass liner was removed from the autoclave. The condensed phase reaction mixture comprised two liquid layers. The upper layer (7.6 g) was a water white liquid while the bottom layer (12.7 g) was a viscous yellow oil. The two layers were separated, after which water (6 g total) was added dropwise with stirring to the separated bottom layer, resulting an exotherm to about 85° C., reflecting hydrolysis of 3,3-dimethylbutyl hydrogen sulfate, di(3,3-dimethylbutyl) sulfate, and any 3,3-dimethylbutyl ethyl sulfate to 3,3-dimethylbutanol, and a further phase separation. The top layer obtained in this further separation was a dark red oil (5.1 g) and the bottom layer was a light yellow solution (12.68 g). The top layer was analyzed by GC and found to contain a total of 1.31 g (m.w.=102; 12.8 mmol) crude 3,3-dimethylbutanol (30.4% based on isobutylene added and 13% based on sulfuric acid). Purification of the alcohol could be achieved by NaOH neutralization of the top layer obtained in the hydrolysis reaction followed by distillation at 85 to 90 mm Hg and about 92° C.

Based on the results of this example, it appeared reasonable to obtain 3,3-dimethylbutanol yields of 30–50% based on isobutylene, 12.5 to 21% (higher if higher conversions are achieved) based on sulfuric acid, and an ethylene yield equal to that achieved on isobutylene. A 90% recycle of heptane is possible. Sulfuric acid cannot be recycled unless subjected to spent acid recovery and concentration.

EXAMPLE 2

Each of a series of alkylation/esterification and hydrolysis reactions was carried out substantially in the manner described in Example 1. Sulfuric acid (96% by weight) and heptane were added to a glass liner. The system was flushed with nitrogen and the charge mixture cooled to −15° to −20° C. under agitation at a stir rate of 800 rpm. After the mixture was cooled, ethylene pressure was applied and maintained at a constant level. Uptake of ethylene during the subsequent reaction was monitored. After ethylene pressure had been applied, a metered addition of isobutylene was initiated. After isobutylene addition was complete, the autoclave was vented for removal of ethylene.

The glass liner was thereafter removed from the autoclave. After each reaction, the content of the glass liner was observed to contain two layers, a water white top layer and a viscous yellow oil on the bottom. The top layer was removed, after which the bottom layer was introduced into a distillation pot along with 2× its volume of water. Under nitrogen, the distillation pot was heated to 125° C. and overhead condensate fractions were collected at 90° and 100° C. In each instance, two layers were observed in the collection flask. The top layer was analyzed by G.C. to determine the amount of recovered 3,3-dimethylbutanol. The reaction conditions, gross yield of 3,3-dimethylbutanol, and yields on raw materials for the several reactions of this Example are set forth in Table 1.

As used in this table and elsewhere in these examples, "3-3 DMB" shall mean "3,3-dimethylbutyl," "3,3-dimethylbutyr-," or "3,3-dimethylbutyric," depending on context. Where "DMB ester(s)" appears, the reference is to esters of sulfuric acid, either di(3,3-dimethylbutyl) sulfate, 3,3-dimethylbutyl hydrogen sulfate, 3,3-dimethylbutyl ethyl sulfate or 3,3-dimethylbutyl t-butyl sulfate, or some mixture of two or more of these.

TABLE 1

| Sulfuric Acid | Heptane (mL) | Ethylene (psig) | Isobutylene (mL/min) | Rxn time | mmol 3,3-DMB alcohol | % vs. Isobutylene | % vs. Ethylene (rxn) | % vs. ethylene total | % vs. $H_2SO_4$ |
| --- | --- | --- | --- | --- | --- | --- | --- | --- | --- |
| 10 | 10 | 120 | 0.017 | 4 | 21 | 48.9 | 30.0 | 16.0 | 20.6 |
| 10 | 20 | 100 | 0.017 | 4 | 23 | 53.5 | 34.6 | 18.8 | 22.5 |
| 10 | 20 | 120 | 0.034 | 2 | 25 | 58.2 | 33.3 | 17.2 | 24.5 |
| 10 | 10 | 120 | 0.051 | 1.5 | 21 | 43.4 | 51.2 | 20.4 | 20.6 |
| 10 | 20 | 80 | 0.034 | 2 | 24 | 55.8 | 50.3 | 24.4 | 23.5 |
| 10 | 10 | 120 | 0.034 | 3 | 34 | 52.7 | 47.5 | 25.1 | 33.3 |
| 10 | 10 | 80 | 0.034 | 3 | 27 | 41.9 | 39.4 | 26.6 | 26.5 |
| 20 | 10 | 80 | 0.034 | 4 | 37 | 43.0 | 29.3 | 23.8 | 18.1 |
| 10 | 10 | 120 | 0.034 | 4 | 40 | 46.5 | 37.1 | 19.2 | 39.2 |
| 20 | 10 | 120 | 0.051 | 3 | 32 | 33.1 | 35.9 | 25.7 | 15.7 |
| 10 | 10 | 120 | 0.034 | 2 | 23.5 | 54.7 | 46.0 | 20.2 | 23.0 |
| 20 | 20 | 120 | 0.068 | 3 | 81 | 62.8 | 45.2 | 35.0 | 39.7 |
| 10 | 10 | 100 | 0.034 | 3 | 29.5 | 45.8 | 39.7 | 22.3 | 28.9 |
| 10 | 10 | 140 | 0.034 | 3 | 30.5 | 47.3 | 40.3 | 18.0 | 29.9 |

Note that ethylene usage includes ethylene consumed in the reaction, ethylene contained in the head space, and ethylene absorbed into the heptane phase. Set forth in FIG. 1 is a plot of gross 3,3-dimethylbutanol yield, as well as yields on isobutylene, ethylene, and sulfuric acid, as a function of addition time for an initial charge of 10 g sulfuric acid and 10 mL heptane, an ethylene pressure of 120 psig, and an isobutylene addition rate of 0.034 mL/min. Note that yields on ethylene and isobutylene reach a maximum and then decrease, indicating a loss in selectivity as higher amounts of total olefin are added relative to the sulfuric acid charge, i.e., as the sulfuric acid becomes relatively dilute due to consumption of $HSO_4^-$ during the course of the reaction.

Figure 2:
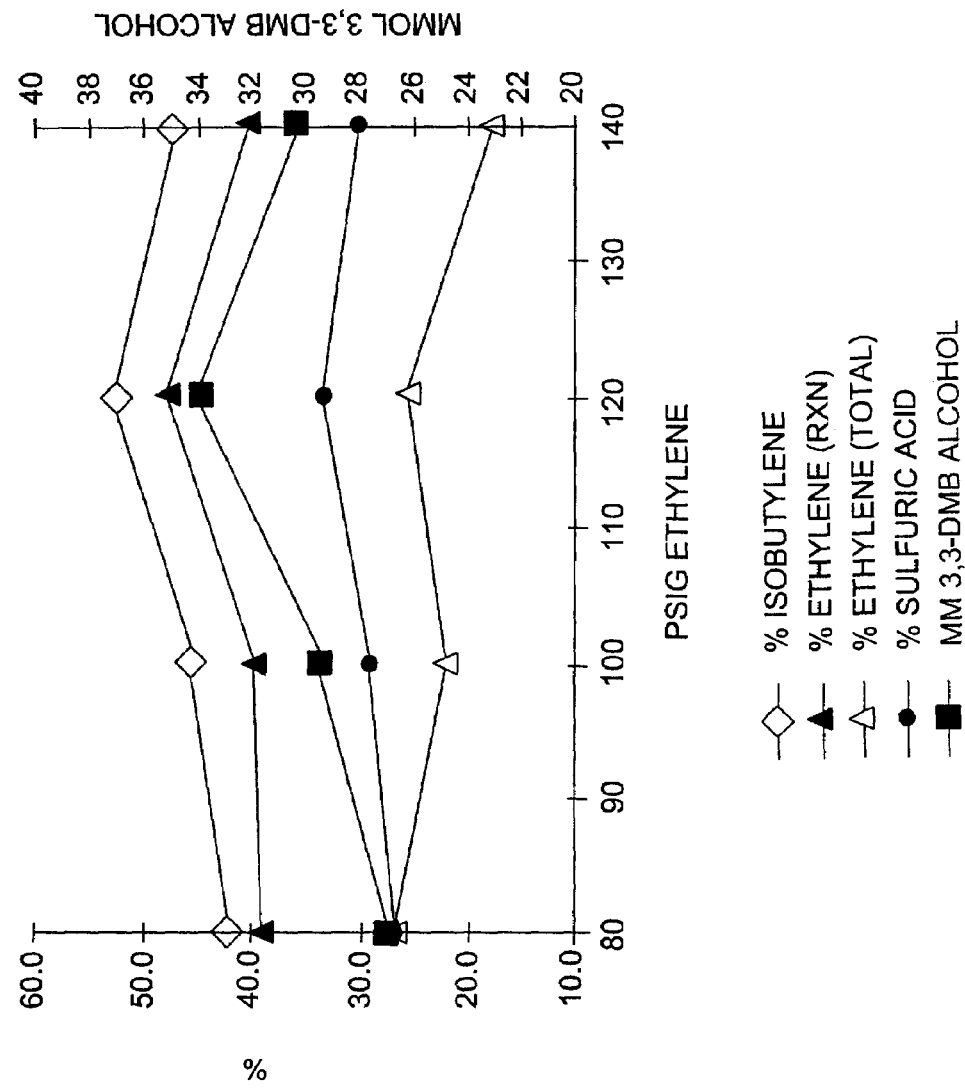
FIG. 2 plots 3,3-dimethylbutanol yield based on isobutylene, ethylene (reacted), ethylene (feed), and sulfuric acid as a function of ethylene pressure during the alkylation/esterification reaction for the combined alkylation/esterification and hydrolysis reactions of Example 2 under the otherwise fixed conditions designated on the plot.
Figure 3:
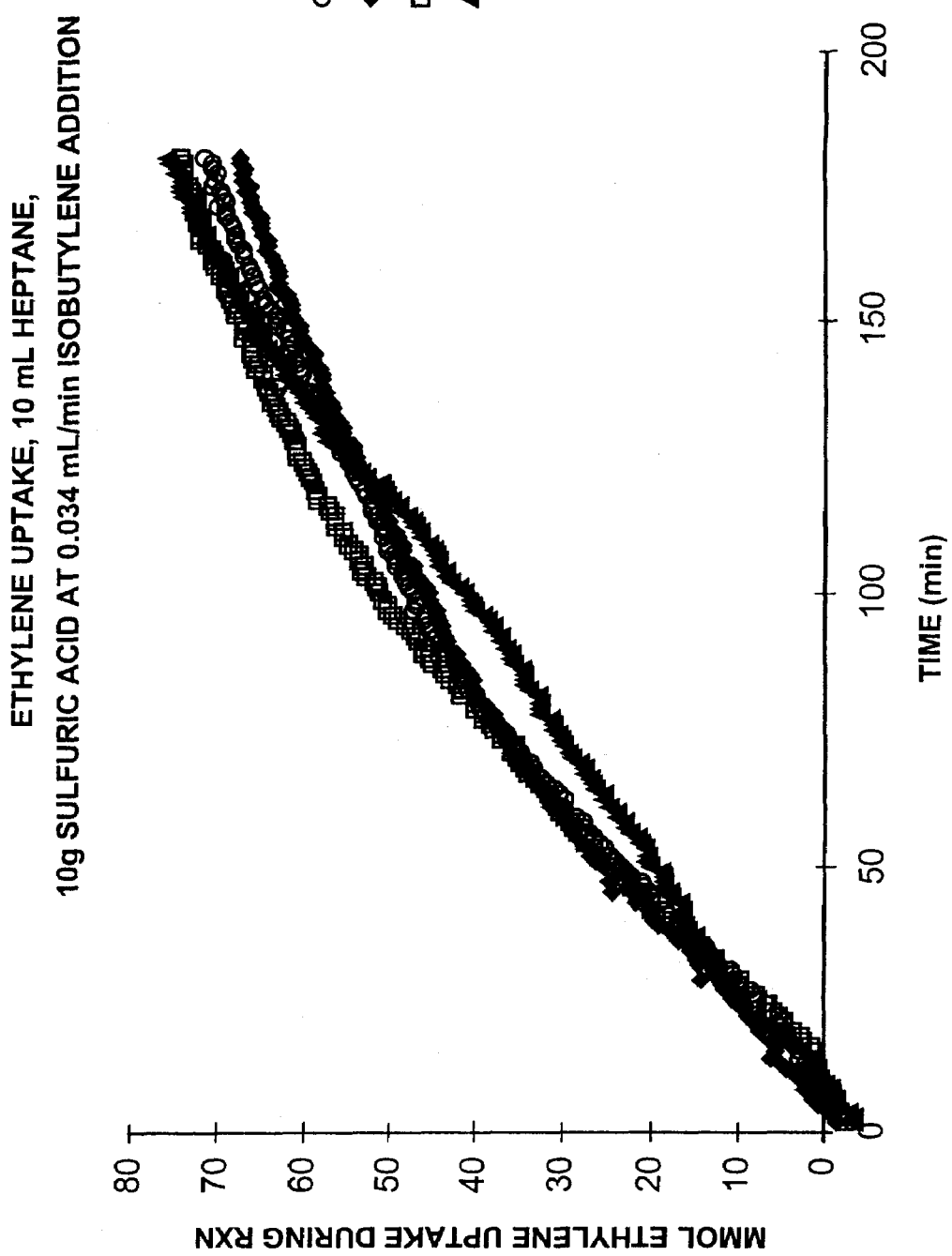
FIG. 3 sets forth plots of cumulative ethylene uptake as a function of time for varying ethylene pressures during the alkylation/esterification reaction for the combined alkylation/esterification and hydrolysis reactions of Example 2 as conducted under otherwise fixed conditions as designated on the diagram.

Set forth in FIG. 2 is a plot of 3,3-dimethylbutanol produced as a function of ethylene pressure under the conditions otherwise the same as those of FIG. 1, and yields obtained on isobutylene, ethylene (reacted), ethylene (total), and sulfuric acid. A plot of ethylene uptake vs. time at various levels of ethylene pressure is set forth FIG. 3. Optimal results for the runs of this example were obtained with a sulfuric acid charge of 10 g, a heptane charge of 10 mL, an ethylene pressure of 120 psig, and an isobutylene feed rate of 0.068 mL/hr.

EXAMPLE 3

Sulfuric acid (20 g; 196 mmol; 96% by weight) and heptane (20 mL; 13.45 g) were charged to a glass liner for a 100 cc Parr autoclave. The glass liner was placed into the autoclave and the head attached. The autoclave was jacketed and provided with an overhead magnetically driven stirrer, a thermocouple, a gas inlet for nitrogen and an inlet for isobutylene. Cooling was provided by circulation of an ethylene glycol/water solution through the jacket from an insulated bath. After the system was flushed with nitrogen, the charge mixture was cooled to −15° C. under agitation at 800 rpm. At this temperature, ethylene was introduced from a reservoir into the head space of the autoclave at a pressure of 120 psig, and this pressure was maintained throughout the course of the reaction. Twenty five minutes after ethylene pressure was applied, addition of isobutylene was commenced at a metered rate of 8.16 mL/hr (4.81 g/hr) while the reaction mixture was maintained at −15° C. by removal of heat to cooling water in the jacket. After 50 minutes, the addition of isobutylene was terminated, at which point the cumulative amount of isobutylene added was 4 g (72 mmol); and 15 minutes after termination of isobutylene addition, the autoclave was vented. Uptake of ethylene was measured by the drop in pressure in the reservoir (of known volume). Under the conditions of this example, the initial uptake of ethylene was 2.46 g (88 mmol; 0.123 g/mL) heptane; and uptake of ethylene during the reaction was determined to be 2.13 g (76 mmol), so that total ethylene consumed and vented was 4.59 g (160 mmol).

After ethylene was vented, the glass liner was removed from the autoclave. It was observed that the reaction mixture comprised two liquid layers. The top layer was removed as a light yellow liquid (13.61 g), leaving a viscous yellow bottom layer. A GC analysis of the top layer gave about 1.7% by weight impurities (0.23 g) total. Proton NMR analysis of the bottom layer in DMSO-$d_6$ indicated roughly the following calculated quantities:

R—CH$_2$—SO$_3$—X (X=H or R' where R$^1$ is ethyl or 3,3'-dimethylbutyl and R is methyl or t-butyl-CH$_2$): 66 mmol (of which roughly 80% was 3,3-dimethylbutyl-OSO$_3$X and the remainder Et-OSO$_3$X)

ethers (R—CH$_2$—O—CH$_2$—R): 3 mmol; R and R$^{11}$ are independently methyl or t-butylCH$_2$ heptane: 0.2 to 0.3 g Calculated isobutylene usage was 3.3 g (59 mmol) (assumes all ether as bis(3,3-dimethylbutyl) ether). Calculated ethylene usage was 2.02 g. (72 mmol).

EXAMPLE 4

Sulfuric acid (5 g; 66% by weight; 49 mmol) and heptane (6.73 g; 67 mmol) were charged to a glass liner for an autoclave of the type generally described in Example 3. The autoclave was further provided with an inlet for sulfuric acid. The glass liner was placed in the autoclave and the head attached. After the system was flushed with nitrogen, the charge mixture was agitated at a stir rate of 800 rpm and cooled to −15 degrees C. At this temperature, ethylene was added at an overhead pressure of 120 psig and this pressure was maintained throughout the course of the subsequent alkylation/esterification reaction. Fifteen minutes after ethylene pressure was applied from a reservoir, a metered addition of isobutylene was initiated at a rate of 3.06 mL/hr (density of isobutylene=0.59; 1.81 g/hr; 31 mmol/hr) and a metered addition of sulfuric acid (96% by weight) was initiated at a rate of 3.32 g/hr (32.5 mmol/hr) while the reaction temperature was maintained at −15 degrees C. After 4.5 hr of simultaneous addition, the introduction of both the isobutylene and sulfuric was terminated. Total sulfuric acid addition was 19.95 g (196 mmol); total isobutylene addition was 13.77 mL (145 mmol). Upon termination of acid and isobutylene addition, the head pressure of ethylene was vented. Uptake of ethylene was measured by the drop in pressure of the ethylene reservoir (of known volume). Under the conditions of this example, the initial uptake of ethylene was 66 mmol (1.85 g) and uptake during the reaction was 1.26 mmol (3.53 g), for a total uptake of 192 mmol (5.38 g).

The glass liner was removed from the reactor. It contained two liquid layers. The top layer was removed as a light yellow liquid (8.87 g; 2.14 g weight gain based on the heptane charge) while the bottom layer was a viscous yellow oil (27.86 g; 7.91 g weight gain based on acid charge).

Proton NMR analysis of the bottom layer in DMSO-$d_6$ indicated 2 by integration roughly 80 mmol eq. of alkylsulfate groups of which the majority appeared to be 3,3-dimethylbutyl sulfate groups. Yield on isobutylene (145 mmol charge) was 55%; yield on ethylene (192 mmol consumption) was 42% and yield on sulfuric acid (195 mmol charge) was 41%.

EXAMPLE 5

Additional alkylation/esterification reaction runs were made substantially in the manner described in Example 4 but with variation in the combination of initial heptane charge, total sulfuric acid charge, isobutylene addition rate, ethylene pressure and total reaction time. Total 3,3-dimethylbutanol yield and percentage yield on sulfuric acid, ethylene, and isobutylene are set forth in Table 2.

TABLE 2

Additional Examples Using Method B for Alkylsulfate Synthesis

| Rxn# | Heptane (mL) | H$_2$SO$_4$ (g) | C$_2$H$_4$ psig | C$_4$H$_8$ mL/min | total rxn time(hr) | 3,3-DMB esters meq | % H$_2$SO$_4$ | % C$_2$H$_4$ | % C$_4$H$_8$ |
|---|---|---|---|---|---|---|---|---|---|
| 21 | 20 | 20.53 | 120 | 0.068 | 3 | 80 | 40 | 36 | 62.5 |
| 22 | 10 | 21.56 | 120 | 0.068 | 3 | 97 | 46 | 53 | 76 |
| 23 | 20 | 12.65 | 120 | 0.034 | 2.5 | 41 | 27 | 23 | 64 |
| 24 | 10 | 19.95 | 120 | 0.051 | 4.5 | 80 | 41 | 42 | 55 |
| 25 | 0 | 21.37 | 120 | 0.051 | 4.5 | 58 | 28 | 41 | 40 |
| 26 | 0 | 17.08 | 140 | 0.041 | 4.5 | 52 | 31 | 37 | 44 |
| 27 | 0 | 24.82 | 140 | 0.031 | 4.5 | 62 | 26 | 41 | 43 |

EXAMPLE 6

Further alkylation/esterification reaction runs were conducted substantially in the manner described in Example 4 except that: in two runs the sulfuric acid and isobutylene additions were each completed after three hours; in the third run, sulfuric acid addition and isobutylene addition were carried out over five hours; in two runs, the reaction temperature was −14° C.; and in another run the reaction temperature was −11° C. The results of the runs of this example are set forth in Table 3.

TABLE 3

Additional Examples Using Method B for Alkylsulfate Synthesis (3 hr addition of isobutylene and sulfuric at ca. −14° C. with 10 mL Heptane and 120 psig ethylene)

| Run # | meq. 3,3-DMB esters | % Isobutylene | % Ethylene | % $H_2SO_4$ |
|---|---|---|---|---|
| 30 | 80 | 62 | 45 | 40.5 |
| 31 | 89 | 59 | 45 | 45 |
| 32 | 110 | 62 | 48 | 40.5 |

Rxn 30 at ca. −11° C. Rxn 217 with slightly increased isobutylene addition rate.
Run 32 addition of isobutylene and sulfuric for 5 hr (same metering rate)

EXAMPLE 7

Sulfuric acid (5 g; 66% by weight; 49 mmol) and heptane (6.65 g; 66.5 mmol) were charged to a glass liner for an autoclave of the type used in Example 4. The glass liner was placed in the autoclave and the head attached. After the system was flushed with nitrogen, the charge mixture was agitated at a stir rate of 800 rpm and cooled to −15 degrees C. At this temperature, an overhead pressure of 120 psig ethylene was established and maintained throughout the course of the reaction by delivery of ethylene from a reservoir. Five minutes after ethylene pressure was initially applied, metered addition of isobutylene was commenced at a rate of 3.36 mL/hr (1.98 g/hr) and metered addition of sulfuric acid simultaneously initiated at a rate of 4.95 g/hr (49 mmol/hr). During addition of acid and isobutylene the temperature was maintained at −15 degrees C. by circulation of ethylene/glycol water solution through the autoclave jacket. After three hours of simultaneous addition of sulfuric acid and isobutylene, sulfuric acid addition was terminated (total sulfuric acid addition=19.85 g; 194 mmol). Isobutylene addition was continued for an additional three hours at a rate which was continuously decreased in a linear fashion from 3.36 mL/hr when sulfuric acid addition was terminated to 0.84 mL/hr just before termination of isobutylene addition. Total addition of isobutylene was 16.39 mL (173 mmol). Upon termination of isobutylene addition, ethylene head pressure was vented. Under the conditions of this example, initial ethylene uptake was 65 mmol (1.82 g), and uptake during the course of the reaction was 178 mmol (4.98 g), so that total ethylene consumption was 243 mmol (6.80 g).

The glass liner was removed from the reactor and found to contain two liquid layers. The top layer was decanted as a light yellow liquid (7.74 g; 1.19 g weight gain based on heptane charge). The bottom layer was a viscous yellow oil (30.70 g; 10.85 g weight gain based on sulfuric acid charge).

Proton NMR analysis of the bottom layer in DMSO-$d_6$ using toluene as a standard (0.1064 g acid layer; 0.1054 g toluene in mL solvent) indicated by integration that the yield was 76 mmol monoalkyl sulfate, 21 mmol dialkyl sulfate, and 7 mmol alcohol. An aliquot of the acid layer was titrated to determine residual acidity. A sample of the acid layer (111 g) was weighed into a 125 mL Erlenmeyer flask. To this sample was added 0.100N NaOH (25.0 mL) and methyl red as an indicator. The sample was back titrated against a 0.100N aq. HCl (15.9 mL) giving 8.2 mmol [$H^+$]/g acid layer.

A second aliquot of the acid layer was analyzed by ion chromatography which indicated a 3,3-dimethylbutyl sulfate to ethyl sulfate ratio of 1.0:0.099 (91% 3,3-dimethylbutyl groups). Using this area ratio to factor the quantity of 3,3-dimethylbutyl groups in the sulfate ester formation determined via NMR analysis, 114 mmol 3,3-dimethylbutyl equivalents were calculated. The quantity of remaining unreacted sulfuric acid was determined to be 36.8% on a weight basis (11.3 g; 115 mmol; 41% $H_2SO_4$ reacted). Based on the above analysis the yield on isobutylene (173 mmol) was 66%; yield on ethylene (243 mmol) was 47%; and yield on sulfuric acid (194 mmol) was 59%.

EXAMPLE 8

Additional alkylation/esterification reaction runs were conducted substantially in the manner described in Example 7, but with variations in the total sulfuric acid charge, rate of sulfuric acid addition, schedule of isobutylene addition rates, and total isobutylene charge. The results of the runs of this Example are set forth in Table 4.

TABLE 4

| Reaction # | 40 | 41 | 42 | 43 |
|---|---|---|---|---|
| Total H2SO4 (mmol) | 199 | 196 | 197 | 194 |
| Rate $H_2SO_4$ (mmol/hr) | 50–3 hr | 75–2 hr | 50–3 hr | 48–3 hr |
| Initial Rate Isobutylene (mmol/hr) | 35.4–3 hr | 35.4–3 hr | 35.4–3 hr | 35.4–3 hr |
| Final rate (mmol/hr) | 17.7–3.5 hr | 17.7–2 hr | ramp to 0–2 hr | ramp to 9–3 hr |
| Total Isobutylene (mmol) | 168 | 145 | 144 | 173 |
| Total ethylene (mmol) | 226 | 213 | 235 | 242 |
| mmol di-alkylsufate (NMR) | 16 | 11.5 | 19.5 | 21 |
| mmol mono-alkylsulfate (NMR) | 68 | 66 | 71 | 76 |
| mmol free alcohol | 9 | 6 | 3 | 7 |
| ratio 3,3DMB: ethyl (I.C.) | 1:0.074 | 1:0.283 | 1:0.214 | 1:0.099 |
| total 3,3-DMB esters meq. | 101 | 74 | 93 | 114 |
| & yield on $H_2SO_4$ | 51 | 38 | 47 | 59 |
| % yield on ethylene | 47 | 35 | 40 | 47 |
| % yield on isobutylene | 60 | 51 | 65 | 66 |
| [H+]/g (titration) | — | 9.7 | 9.05 | 8.2 |

EXAMPLE 9

Sulfuric acid (20 g; 66% by weight; 196 mmol) and heptane (20 mL; 13.45 g) were charged to a glass liner for an autoclave of the type used in Example 4. The glass liner was placed in the autoclave and the head attached. After the system was flushed with nitrogen, the charge mixture was agitated at a stir rate of 800 rpm and cooled to −15 degrees C. At this temperature, an overhead pressure of 120 psig ethylene was established and maintained throughout the course of the reaction by delivery of ethylene from a reservoir. Twenty five minutes after ethylene pressure was initially applied, metered addition of isobutylene was commenced at a rate of 8.16 mL/hr (4.81 g/hr). During addition of isobutylene the temperature was maintained at −15 degrees C. by circulation of ethylene/glycol water solution through the autoclave jacket. The addition of isobutylene was terminated after 50 minutes (total isobutylene added 4 g; 72 mmol). The ethylene head pressure was vented 15 minutes after termination of isobutylene addition. Under the conditions of this example, initial ethylene uptake was 88 mmol (2.46 g; 0.123 g/mL heptane), uptake during the course of the reaction was 76 mmol (2.13 g), so that total ethylene consumption was 160 mmol (4.59 g).

The glass liner was removed from the autoclave and observed to contain two liquid layers. The top layer was removed as a light yellow liquid (13.16 g; GC analysis gave about 1.7% by weight impurities; 0.23 g total), while the bottom layer was a viscous yellow oil (25.24 g). Proton NMR analysis of the bottom layer in DMSO-$d_6$ indicated roughly the following calculated quantities: 66 mmol R—CH$_2$O—SO$_3$—X groups (X=H or R') of which 80% (roughly) are 3,3-dimethylbutyl-OSO$_3$—X and the remainder Et-OSO$_3$—X and 3 mmol alcohols (R—CH$_2$OH).

Water (25.1 g) was added to the bottom layer, and the reaction mixture was distilled under nitrogen (no column). A light fraction was collected at 70°–90° C. (0.3 g; which by area % contained 0.25 g heptane and 0.04 g 3,3-dimethylbutanol) and a second fraction at 90° to 98° C. Condensation of the second fraction produced a two phase condensate comprising an organic top layer (5.1 g) and an aqueous bottom layer (6.1 g). The top layer of the second fraction condensate contained bis-(3,3-dimethylbutyl)ether (0.352 g), ethanol (0.2 g) and heptane (0.1 g). The aqueous layer contained ethanol (0.25 g) and a small amount of 3,3-dimethylbutyl alcohol. Water (14 g) was then added to the distillation pot and distillation resumed. A third fraction was collected at 980 ° to 100° C. which contained two layers. The top organic layer (0.7 g) was analyzed and determined to contain 3,3-dimethylbutanol (0.36 g), and the remainder, by area, higher boiling impurities. The bottom aqueous layer (13.34 g) contained only a trace of alcohols. A summary of the compositions of the fractions obtained in the reactive distillation, and the temperatures at which they were obtained, is set forth in Table 5.

Total weight of the charge to the reactive distillation was 63.34 g (25.24 g alkylation/esterification reaction product and 39.1 g water). Of this 63.74 g were accounted for in the fractions obtained.

The heptane layer obtained in the reaction of Example 3 was subjected to a simple takeover distillation at bath temperature of 125° C. Collection was continued until the pot temperature reached 100° C., at which point 10.9 g distillate had been recovered from an initial charge to the pot of 12.47 g. GC analysis of the distillate indicated 0.15% by weight impurities and the remainder heptane (10.73 g). Heptane balance was as follows:

Heptane in=13.45 g
Heptane from distillation of alk./ester. acid layer=0.35 g
Heptane in org. layer of alk./ester=13.61−0.23=13.38 g
Accountability prior to distillation=102%
Distillation gave 10.73 g heptane=80% recovery overall Yields of 3,3-dimethylbutanol obtained from the distillation, and yields on raw materials initially charged are set forth in Table 6.

TABLE 6

|  | grams 3,3-DMB alcohol | mmol 3,3-DMB alcohol | % yield on isobutylene | % yield on total ethylene | % yield on rxn ethylene | % yield on sulfuric acid |
|---|---|---|---|---|---|---|
| total fractions | 4.82 | 47 | 65% | 30% | 62% | 24% |
| fraction 2 | 4.42 | 43 | 60% | 27% | 57% | 22% |

Fraction #2 material (4.97 g) from the crude takeover distillation was refined by distillation at 80 torr and a pot temperature of 125° C. Conditions of the distillation and compositions of the fractions obtained are set forth in Table 7.

TABLE 7

|  | pot | fraction #1 | fraction #2 | total |
|---|---|---|---|---|
| Temperature | 125° C. | <82° C. | 82–84° C. |  |
| 3,3-DMB alcohol | 0.13 g | 0.33 g | 3.2 g | 3.66 g |
| 3,3-DMB ether | — | — | 0.15 g | 0.15 g |
| Ethanol |  | 0.14 | — | 0.14 g |
| heptane |  | 0.07 g | — | 0.07 g |
| total | 0.26 g | 0.9 g (includes water) | 3.36 g | 4.52 g | weight into refining = 4.97 g
weight out = 4.52
accountability = 91%
3,3-DMB alcohol % check in fraction #2 by area = 95%, by weight = 96% (hexanol internal standard)

TABLE 5

|  | Distillation Pot | Fraction #1 | Fraction #2 | Fraction #3 | Total |
|---|---|---|---|---|---|
| Temperature | 125° C. | 70°–90° C. | 90°–98° C. | 98°–100° C. | — |
| 3,3-DMB alcohol | — | 0.04 g | 4.42 g | 0.36 g | 4.82 g |
| Heptane | — | 0.25 g | 0.1 g | — | 0.35 g |
| 3,3-DMB ether | — | — | 0.32 g | — | 0.32 g |
| Ethanol | — | trace | 0.2 g | — | 0.2 g |
| Aqueous | 38.2 g | — | 6.1 g* | 13.34 g | 57.64 g |
| Total wt (org/aq.) | trace oil/38.2 g | 0.3 g | 5.1/ 6.1 g | 0.7/ 13.34 g | 6.1/ 57.64 g |

*in the 6.1 g aqueous layer was 0.25 g ethanol

EXAMPLE 10

A simulated 3,3-dimethylbutyl sulfate hydrolysis reaction mixture was prepared by mixing heptane (5 g), 3,3-dimethylbutanol (5 g), water (10 g), ethanol (5 g), and sulfuric acid (100% basis; 5 g). The charge was stirred to provide a uniform mixture, and the mixture thereafter allowed to separate. Two layers were obtained, the top layer weighing 11.93 g and the bottom layer 18.3 g. Analysis of the top layer indicated that it contained 3,3-dimethylbutanol (4.42 g), ethanol (1.65 g), heptane (5.15 g) and water/sulfuric acid (0.7 g by difference). The top layer was distilled to provide three fractions. Condensing the first fraction yielded two liquid layers (5.9 g total) together containing 4.1 g heptane, with only a trace of either 3,3-dimethylbutanol or ethanol. The second fraction (0.9 g) contained all components, while the third fraction (2.3 g) contained 3,3-dimethylbutanol and a small amount of an unknown side product. The residue in the pot (2.8 g) contained a small amount of 3,3-dimethylbutanol and a major fraction of by-product, surmised to comprise bis(3,3-dimethylbutyl) ether.

It was observed that the residual acid in the organic layer obtained from the initial separation was detrimental to the distillation thereof. A second mixture was made as described above; but, prior to distillation, 0.1 N KOH was added to the mixture to neutralize residual acid (3.5 mmol KOH was required as determined by methyl red indicator). Distillation was carried out at about 100 torr, yielding two major fractions. The first fraction contained heptane (4.4 g) and a trace of 3,3-dimethylbutanol. The second fraction contained 3,3-dimethylbutanol; while the pot fraction contained 0.5 g alcohol with only a trace of decomposition products.

EXAMPLE 11

A 300 mL ACE pressure rated glass reactor (flask 1) was equipped with a Teflon coated magnetic stir bar and a thermocouple connected to a temperature controller. Sulfuric acid (98% by weight; 22.8 mL; 41.9 g; 0.428 mmol) and heptane (30 mL) were added to flask 1. The flask was cooled to −15° C. with a cooling bath and pressurized to 100 psi with ethylene. Heptane (20 mL) and isobutylene (12 g) were added to a separate ACE 75 mL pressure rated flask (flask 2). Flask 2 was pressurized to 120 psi. The isobutylene/heptane mixture in flask 2 was added to flask 1 with vigorous agitation over a period of three hours (a rate of 0.2 mL per minute). Flask 1 was maintained at 110 psi ethylene and −15° C. throughout the reaction. After addition of isobutylene/heptane solution was complete, agitation of the reaction mixture in flask 1 was continued for another 20 minutes before the flask was depressurized and warmed to 0° C. Water (100 mL) was added slowly to the mixture in flask 1 at 0° C., resulting in the formation of two layers: a heptane layer and a aqueous sulfate layer. The heptane layer was discarded and the aqueous sulfate layer was transferred into a distilling set up which consisted of a distilling column, a Dean Stark receiver and a condenser. The 3,3-dimethylbutanol product was distilled from the flask as a water azeotrope while the water layer in the Dean Stark receiver was returned continuously to the distilling flask. A yield of 3,3-dimethylbutanol was 48.9% (based on isobutylene).

EXAMPLE 12

Alkylation and esterification reactions were carried out in the manner described in Example 11 except that decane was substituted for heptane as the solvent, and the initial charge of decane to flask 1 was 50 mL. Reaction conditions and work up were otherwise identical to those described in Example 11. The yield of 3,3-dimethylbutanol product by distillation of the pregnant liquor obtained from flask 1 was 74.7% (based on isobutylene).

EXAMPLE 13

Figure 4:
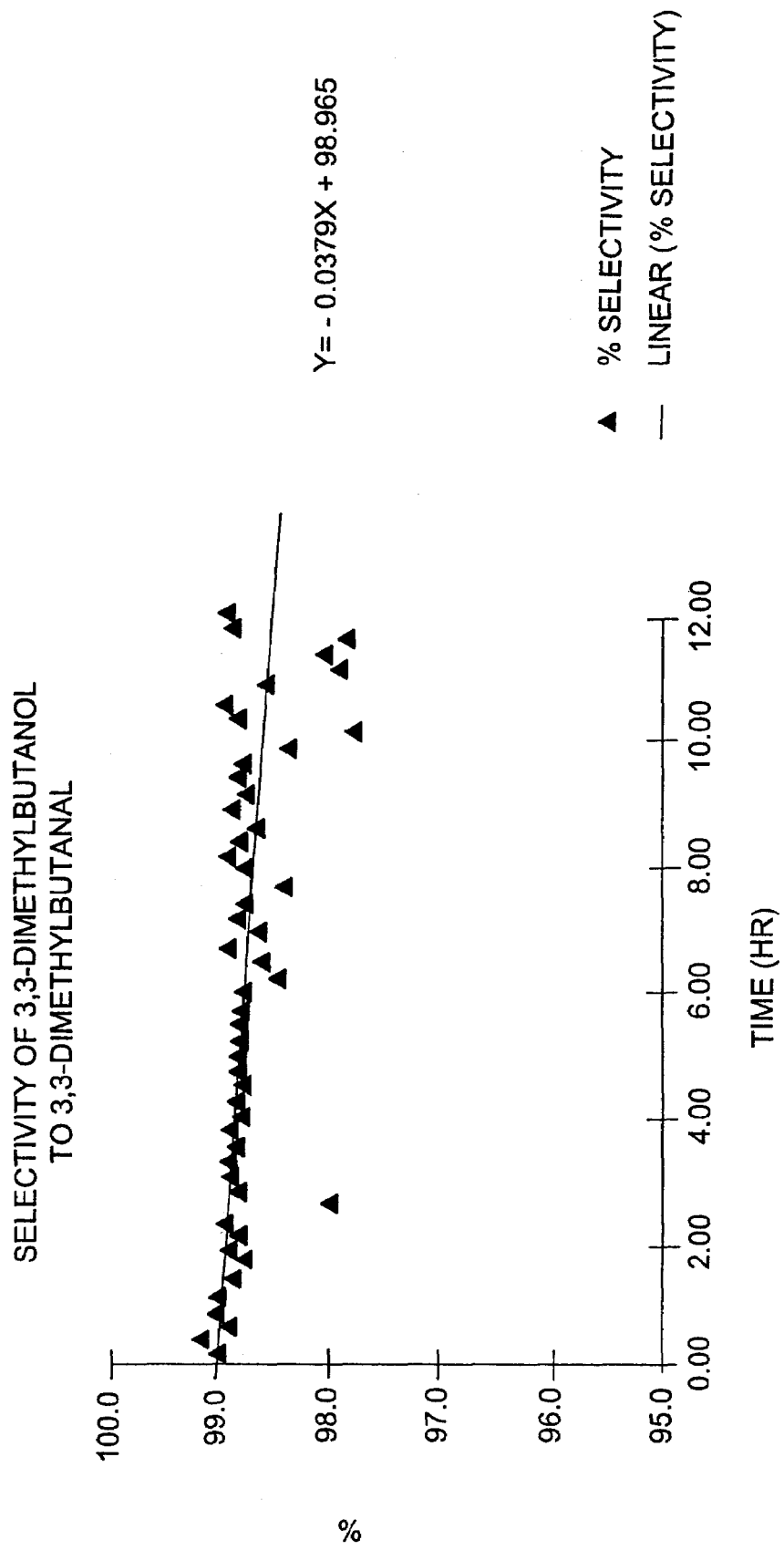
FIG. 4 is a plot of selectivity as a function of time during the fixed bed catalytic dehydrogenation of 3,3-dimethylbutanol to 3,3-dimethylbutanal described in Example 6.

3,3-Dimethylbutanol (10% by volume) was vaporized into a helium carrier and passed over a fixed bed comprising CuO (2 g supported on silica/aluminum containing alkaline earth oxide). Flow rate of the gas stream was 200 sccm at a bed temperature of 260° C. Initially, a stoichiometric oxidation reaction was obtained in which 3,3-dimethylbutanol was converted to 3,3-dimethylbutanal. As stoichiometric oxidation proceeded, the CuO in the bed was progressively reduced to $Cu^0$, after which conversion of 3,3-dimethylbutanol to 3,3-dimethylbutanal continued by non-oxidative catalytic dehydrogenation. Conversion of 3,3-dimethylbutanol to 3,3-dimethylbutanal was initially about 55%, declining over twelve hours to approximately 45%, with a corresponding decline in productivity from about 1.5 g aldehyde/g catalyst-hr to about 1.25 g aldehyde/g catalyst-hr. However, a high selectivity to 3,3-dimethylbutanal was maintained throughout the run. A plot of selectivity vs. time is set forth in FIG. 4

Product of the reaction was passed through an ice trap for aldehyde and alcohol recovery. The clear white water mixture obtained was purified by distillation (49.9 g recovered material; 76% yield based on feed to the fixed bed reactor). Composition of the accumulated condensate as indicated by GC was 43.5% 3,3-dimethylbutanal (217 g; 66% based on GC rector data), and 56.5% 3,3-dimethylbutanol (28.2 g; 89% based on GC reactor data). Distillation was carried out at 85 to 90 mm Hg using a Snyder column with three levels (bulbs). Analysis of the resulting fractions is set forth in Table 8.

TABLE 8

| Fraction (temp) | #1 (45° C.) | #2 (46–84° C.) | #3 (85–86° C.) | pot | total | % of recovery |
|---|---|---|---|---|---|---|
| grams | 18 | 2.3 | 22.6 | 3 | 45.9 g | 92% (of initial) |
| 3,3-DMB % aldehyde | 99 | 81 | 0 | 0 | — | |
| 3,3-DMB % alcohol | 1 | 19 | 100 | 86 | — | |
| 3,3-DMB % acid | 0 | 0 | 0 | 6 | — | |

TABLE 8-continued

| Fraction (temp) | #1 (45° C.) | #2 (46–84° C.) | #3 (85–86° C.) | pot | total | % of recovery |
|---|---|---|---|---|---|---|
| % unknowns | 0 | 0 | 0 | 8 | — | |
| g 3,3-DMB aldehyde | 17.8 | 1.9 | 0 | 0 | 19.7 g | 42.9% |
| g 3,3-DMB alcohol | 0.2 | 0.4 | 22.6 | 2.6 | 25.8 g | 56.2% |
| g 3,3-DMB acid | 0 | 0 | 0 | 0.2 | 0.2 g | 0.4% |
| g unknowns | 0 | 0 | 0 | 0.2 | 0.2 g | 0.5% |

Very little change in composition was observed during the distillation as indicated by the recovered amounts of each component. Separation of aldehyde from alcohol was very good (82% of the aldehyde in the crude feed to the distillation was recovered in 99% purity).

Although the conversion of alcohol to aldehyde is reversible, the equilibrium is favorable. At the nominal temperatures at which this reaction was run over a supported Cu catalyst, i.e., in the range of 2500 to 300° C., very high conversion to aldehyde is favored. For example, with 5 mole % alcohol in the feed stream, the equilibrium conversion to aldehyde was 96% at 300° C. For the computed heat of reaction of 17 Kcal/mole, the equilibrium constant doubles for each 20° C. temperature increases. Even at 260° C., the equilibrium conversion is over 80% with a 10 mole % alcohol feed.

The adiabatic temperature decrease on converting 90+% alcohol feed (5 mole % alcohol) is about 100° C. Productivity of the reaction is very high. A conversion of greater than 90% was achieved at a gas residence time of less than 1 second.

EXAMPLE 14

A stream of 3,3-dimethylbutanol produced in Example 1 was converted to 3,3-dimethylbutanal by stoichiometric oxidation with CuO, followed by anaerobic catalytic dehydrogenation over the $Cu^0$ catalyst produced in situ in the stoichiometric oxidation reaction. A tubular reactor was constructed comprising a ½" diameter inner tube adapted to contain a fixed catalyst bed, and an outer tube concentric with the inner tube, defining an annular space within which feed gas could flow before entry into the inner tube. One end of the outer tube was in communication with an inlet on the inner tube. The other end of the outer tube was connected to a supply of feed gas for the reaction. Heating means surrounding the outer tube were provided for preheating the gas entering the reactor system.

The inner tube of the reactor was charged with Cu oxide on a particulate inert support (4 g; 70% CuO) and having a particle size of between about 0.6 mm and about 1.7 mm. A constant flow of helium was established through the annular space and inner tube at a temperature of 250° C. and a pressure of 10 psig. Wet 3,3-dimethylbutanol (94–95% 3,3-dimethylbutanol; 5–6% water) was vaporized into the helium stream at 185° C. to produce a feed gas for the reactor comprised of 5% by volume 3,3-dimethylbutanol and 95% by volume helium. Conversion of 3,3-dimethylbutanol to 3,3-dimethylbutanal proceeded, initially by stoichiometric oxidation. After about 1 to 2 hours, the reaction changed from exothermic to endothermic, as indicated by a decline of about 5° C. in the temperature of the catalyst bed. Appearance of the endotherm indicated that the CuO was becoming exhausted. Conversion of 3,3-dimethylbutanol to 3,3-dimethylbutanal continued, however, by anaerobic catalytic dehydrogenation over $Cu^0$. By application of heat to the feed gas, the temperature of the reaction was raised to a final temperature of 325° C., at which the reaction was allowed to run continuously for 48 hours, showing very little loss in activity or selectivity. The reaction product was collected in a Fisher bottle cooled to −7° C.

A summary of the results of 48 hours continuous reaction is set forth in Table 9.

TABLE 9

| | | | |
|---|---|---|---|
| % 3,3-DMB alcohol purity | 95% | | |
| temperature | 325° C. | g olefin | 0.53 |
| grams cat | 4 | % Select Olefin | 0.45 |
| 3,3-DMB alcohol feed | 0.054 | g 3,3-DMB ether | 0.42 |
| time | 47.13 | % Select Ether | 0.36 |
| total 3,3-DMB alcohol feed | 122.42 | g 3,3-DMB ester | 0.98 |
| total 3,3-DMB aldehyde | 113.61 | % Select ester | 0.85 |
| % total | 92.80 | g acid | 0.46 |
| Conversion to | | % Select acid | 0.40 |
| 3,3-DMB aldehyde | | | |
| g ald/g cat/hr | 0.60 | | |
| g 3,3-DMB alcohol | 6.07 | mass total | 122.08 |
| % total Conversion | 95.04 | | |
| % Selectivity to | 97.64 | | |
| 3,3-DMB aldehyde | | | |

Figure 5:
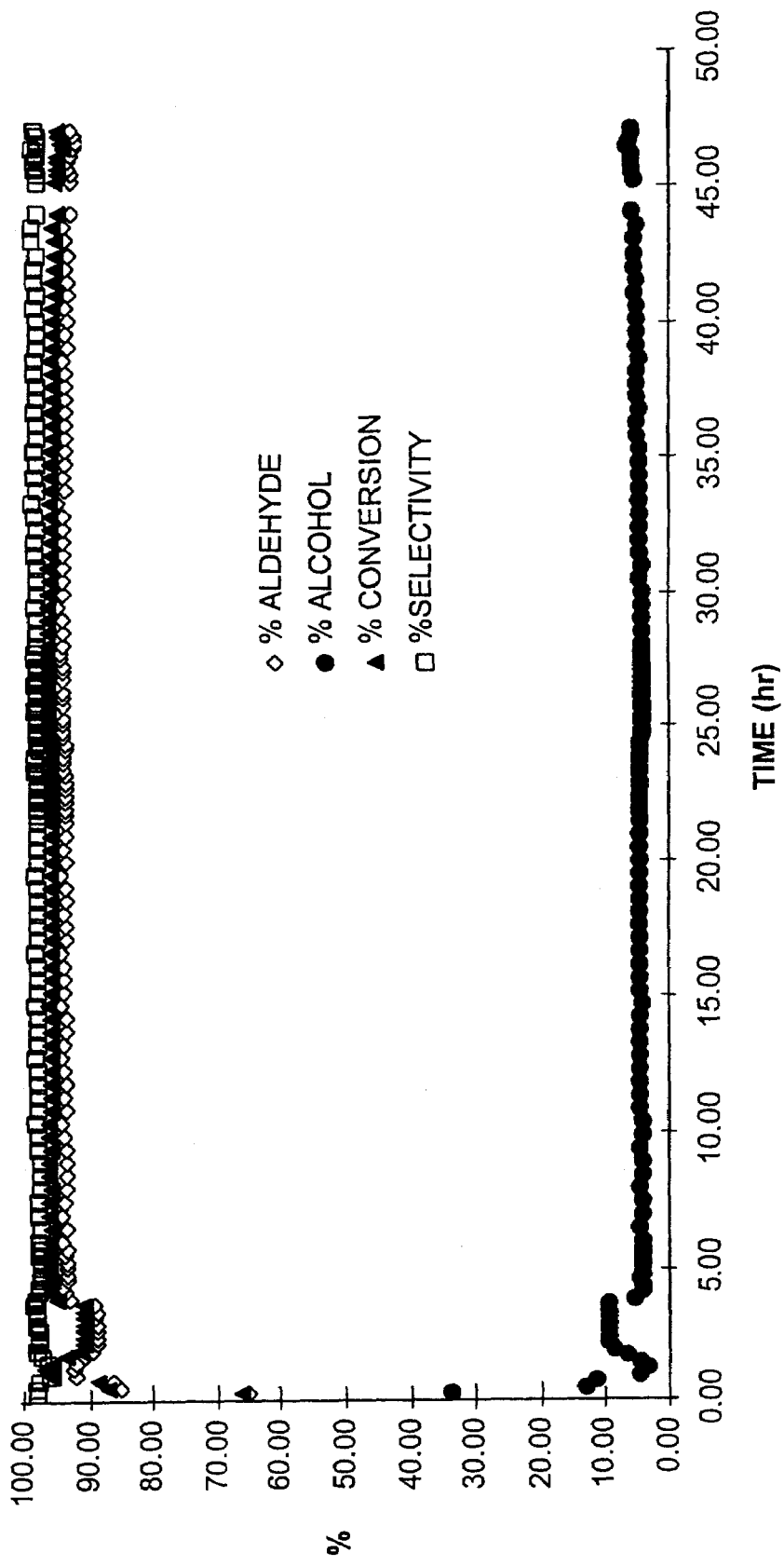
FIG. 5 plots 3,3-dimethylbutanal content, 3,3-dimethylbutanol content, conversion and selectivity in the catalytic dehydrogenation of 3,3-dimethylbutanol to 3,3-dimethylbutanal as a function of time during the 48 hour dehydrogenation run of Example 7.
Figure 6:
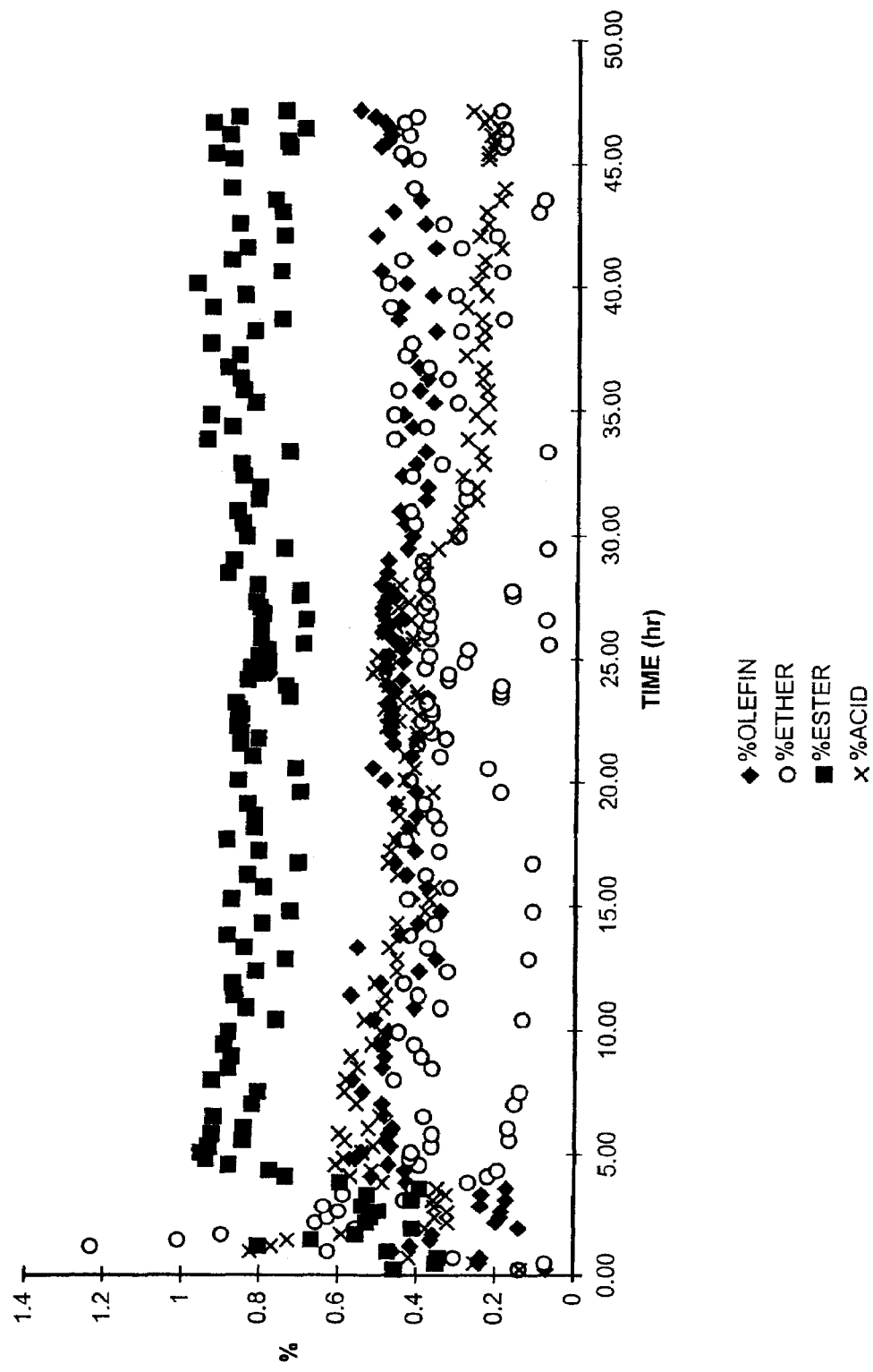
FIG. 6 plots the impurity content in the dehydrogenation reaction gas as a function of time during the 48 hour dehydrogenation run of Example 7.

Selectivity and conversions obtained in the 48 hour reaction run are shown in FIG. 5, with impurity content of the reaction product plotted in FIG. 6.

EXAMPLE 15

Dehydrogenation of 3,3-dimethylbutanol was conducted substantially in the manner described in Example 14. Operation was continued over a period of 142.5 hours. 3,3-Dimethylbutanol was fed to the reactor at a rate of 2.73 g/hr (26.8 mmol/hr; 10 sccm). The catalyst consisted of 4 g (about 2.5 cc) of a copper catalyst designated Cu0330-XLT. Total flow through the bed was 200 sccm using helium as the diluent. Contact time over the catalyst bed was 1.33 seconds. Product gases were analyzed by on line gas chromatographs. Results of run of this example are set forth in Table 10.

TABLE 10

Results from 142.5 hr Continuous
Dehydrogenation of 3,3-dimethylbutanol Using Cu-0330 XLT Catalyst

|  | Mmol (G.C.) | grams (G.C.) | wt % (G.C.) | recovered wt % | recovered grams | recovered mmol | % isolated based on fed alcohol |
|---|---|---|---|---|---|---|---|
| Fed 3,3-DMB Alcohol | 3823 | 389.9 | 100 | | | | |
| 3,3-Dimethylbutanal | 3543 | 354.3 | 91.9 | 85.3 | 273 | 2730 | 71.4 |
| Bis(3,3-DMB) ether | 8.5 | 1.6 | 0.4 | | | | |
| 3,3-DME-3,3-dimethylbutyrate | 17.6 | 3.5 | 0.9 | | | | |
| 3,3-Dimethylbutyric acid | 14.3 | 1.7 | 0.4 | 3.23 | 10.3 | 89 | 2.33 |
| 2,3-dimethyl-2-butene and 3,3-dimethyl-1-butene | 10 | 0.8 | 0.2 | | | | |
| unreacted 3,3-DMB alcohol | 230 | 23.5 | 6.1 | 8.26 | 26.4 | 259 | 6.8 |

The quantities of products produced were calculated from the collective sum of all the traces of the on-line gas chromatographs, based on percentage of product vs. 3,3-DMB alcohol fed. The recovered amount of aldehyde was 320.3 g (7.2 g. calculated hydrogen release); 84% recovery. The high relative amount of 3,3-DMB acid recovered may have been partially due to preferential condensation and partially due to air oxidation of aldehyde in storage and transportation.

EXAMPLE 16

Using a process substantially as described in Example 14, several catalysts were evaluated for their effectiveness in the dehydrogenation of 3,3-dimethylbutanol to 3,3-dimethylbutanal. Compositions of the catalysts are set forth in Table 11, and other characteristics of the catalysts are set forth in Table 12.

TABLE 11

Composition (XRF) of Commercial Catalysts for Dehydrogenation

| Catalyst | Cu-0330XLT (Engelhard) | X-415Tu (Calsicat) | C3150TR (Degussa) | Cu-0865XLE (Engelhard) |
|---|---|---|---|---|
| % Cu | 37.4 | 47.8 | 36.2 | 43.5 |
| % Si | 0 | 3.1 | 24.2 | 10.4 |
| % Al | 14.9 | 11.3 | 0.1 | 0.7 |
| % Na | 1.2 | 3.4 | 1.4 | 1.9 |
| % Ca | 0 | 2.1 | 0 | 11.7 |
| % Mn | 0 | 0.4 | 0 | 0 |

TABLE 12

Dehydrogenation Catalyst Physical Characteristics

| Catalyst | Cu-0330XLT (Engelhard) | X-415Tu (Calsicat) | C3150TR (Degussa) | Cu-0865XLE (Engelhard) |
|---|---|---|---|---|
| Surface area (m$^2$/g) | 30 | 100 | 50 | 45 |
| Pore Volume (ml/g) | 0.16 | 0.3 | 0.83 | 0.45 |
| Density (g/mL) | 1.63 | 1.2 | 0.54 | 0.74 |
| Crush Strength (lb/mm) | 11.31 | 20 | — | 2.94 |

In these tests, Engelhard catalyst 0330-XLT displayed a catalyst life in excess of 100 hours while maintaining a >90% conversion of alcohol and >95% selectivity to aldehyde (selectivity approached 98% while conversion dropped below 90% after 128 hours). The decline in conversion became apparent at the 80 hour mark of a 142.5 hour test reaction; but there was no loss of selectivity. Degussa catalyst C3150TR and Englehard Cu-0865XLE also provided generally favorable selectivity and reasonable conversions.

EXAMPLE 17

Sodium borohydride (1.61 g) was added dropwise with to a solution of 3,3-dimethylbutyric acid (1.86 g) in DMSO (30 mL) under vigorous agitation at room temperature. Subsequently, a solution of methanesulfonic acid (3.6 mL) in DMSO (10 mL) was added to the mixture. The resulting reaction mixture was stirred for another hour, after which it was quenched with a 10% by weight aqueous sodium hydroxide solution. Yield of 3,3-dimethylbutanol was 50%. The reaction mixture was worked up by repeated extraction with ether, washing the ether extract with water, drying the washed extract by contact with a desiccant, and distilling the dried extract to remove the ether. The resulting 3,3-dimethylbutanol product is a colorless liquid and appears to be pure based on NMR.

EXAMPLE 18

1-Chloro-3,3-dimethylbutane (15 g), zinc oxide (6 g) and water (60 g) were charged to a 150 mL Parr reactor. The reactor was sealed and the charge mixture was heated and stirred at 220° C. for 5 hours. Reactor pressure was about 800 psi. Yield of 3,3-dimethylbutanol was 70%.

EXAMPLE 19

A reactor was charged with potassium acetate (196 g), 1-chloro-3,3-dimethylbutane (241 g) and polyethylene glycol (300 MW; 600 mL). The mixture was heated to reflux and maintained under reflux conditions for 17 hours, then cooled to 100° C. A solution of KOH (197 g) in water (150 mL) was added to the reaction mixture, and the resulting hydrolysis charge mixture was heated to reflux for 2 hours. Distillation and work-up provided 3,3-dimethylbutanol in 81% yield (165 g).

EXAMPLE 20

Lithium aluminum hydride (4.93 g; 0.13 mmol) was added to a solution of ethyl ester of 3,3-dimethylbutyric acid (1.44 g; 0.01 mmol) in dry tetrahydrofuran (20 mL) and the resulting mixture was heated to reflux for 6 hours, then cooled to room temperature. After the reaction mixture was cooled, it was treated carefully with water (20 mL) and then extracted with diethyl ether (3 times with 30 mL aliquots). Combined ether layers were washed with water and a saturated sodium chloride solution then dried over sodium sulfate. Evaporation of the solvent gave essentially pure 3,3-dimethylbutanol in an isolated yield of 77%.

EXAMPLE 21

A potassium acetate solution was prepared by reaction of KOH and acetic acid in polyethylene glycol (MW=300). After removal of water formed in the neutralization, 1-chloro-3,3-dimethylbutane was added and the resulting mixture refluxed for 17 hours with a gradual increase in temperature from 118° to 132° C. at the end of the reaction. Potassium hydroxide dissolved in water was then added to the reaction mixture which was refluxed for two hours. The 3,3-dimethylbutanol was recovered from the reaction mixture by steam distillation. Yield was 81%.

EXAMPLE 22

Various solvents were tested in preparation of the acetate ester of 3,3-dimethylbutanol by acetoxylation of 1-chloro-3,3-dimethylbutane with K acetate. Solvents tested were toluene, dimethylformamide, acetic acid, methanol, propylene glycol, and 1-methyl-pyrrolidinone (NMP). The most favorable results were obtained with NMP. 1-Chloro-3,3-dimethylbutane (1.5 g; 12.4 mmol) potassium acetate (13.7 mmol; 10% excess) and NMP (5 mL) were placed in a three neck round bottom flask equipped with reflux condenser, thermometer, and Teflon coated stirring bar. The suspension was heated to 120° C. and stirred at that temperature for 22 hours under an inert atmosphere. The reaction mixture was cooled to ambient temperature, the white precipitate obtained from the reaction was removed by filtration, and the liquid phase analyzed by GC-MS, which established the formation of the acetate ester of 3,3-dimethylbutanol.

EXAMPLE 23

3,3-Dimethylbutyl acetate (2 g; 13.8 mmol), KOH (0.875 g; 15.3 mmol), and methanol (10 mL) were introduced into a two neck round bottom flask provided with a reflux condenser, thermometer, and stirring bar. The resulting solution was stirred for two hours at room temperature, during which time the acetate was quantitatively converted to 3,3-dimethylbutanol. Only traces of acetate were detected in the GC trace. Similar results were obtained using 1-methyl-pyrrolidinone (10 mL) and water (1 mL) as the solvent medium. Distillation of the alcohol caused potassium acetate to be reformed in the distillation residue. The residue may be recycled for further synthesis of the acetate ester of 3,3-dimethylbutanol per the protocol described in Example 22.

EXAMPLE 24

Ethylene oxide (3 mL; 60 mmol; 2 equival.) was condensed at $-5°$ C. and diluted with dry ether (20 mL). A solution of t-butyl lithium (1.7 M in pentane; 17 mL; 30 mmol; diluted with 40 mL ethyl ether) was prepared and added dropwise to the ethylene oxide solution at $-78°$ C. The reaction mixture was stirred at $-78°$ C. for another hour after which it was allowed to warm up to room temperature and quenched with dilute sulfuric acid. The ether layer was decanted and the aqueous layer was extracted with ether. The combined ether layers were washed with water and dried with $MgSO_4$. Solvent removal followed by distillation provided a 48% yield (1.48 g) 3,3-dimethylbutanol.

EXAMPLE 25

A series of runs was conducted in which 3,3-Dimethylbutene oxide (DMEB) was dissolved in a solvent and charged to an autoclave, a catalyst was slurried in the solution in the autoclave, and hydrogen pressure was applied to effect catalytic hydrogenation of the 3,3-dimethylbutene oxide to 3,3-dimethylbutanol. Various combinations of solvent, catalyst, temperature, hydrogen pressure, reaction time and stir rate were used in the runs of this example. Results of these runs are set forth in Table 13.

TABLE 13

Data on the hydrogenation of 3,3-dimethylbutene Oxide to 3,3-dimethylbutan-1-ol-1

| # | Solvent | DMEB ml | Catalyst | Weight g | Temp °C. | Press psi | Start Rate RPM | Reaction Time | Conversion | Sel** % |
|---|---------|---------|----------|----------|----------|-----------|----------------|---------------|------------|---------|
| | | | | Solvent Effect | | | | | | |
| 7 | | | | | | | | | | |
| 8 | EtOH | 2 | RaNi | 1.3 | 100 | 200 | 1400 | 5 | 59.4 | 73.6 |
| 9 | EtOH | 2 | RaNi | 1.3 | 100 | 1000 | 1400 | 19 | 100 | 63.6 |
| 10 | THF | 2 | RaNi | 1.3 | 100 | 300 | 1400 | 17 | 100 | 60.7 |
| 11 | THF | 2 | RaNi | 1.3 | 100 | 1000 | 1400 | 6 | 94.9 | 46.3 |
| 12 | MeOH | 2 | RaNi | 1.3 | 100 | 200 | 1400 | 5 | 35 | 73.0 |
| 13 | MeOH | 2 | RaNi | 1.3 | 100 | 1000 | 1400 | 5 | 81.8 | 56.4 |
| 14 | MeOH | 2 | RaNi | 1.3 | 100 | 1000 | 1400 | 4.5 | 76.3 | 76.0 |
| 15 | MeOAc | 2 | RaNi | 1.3 | 100 | 1000 | 1400 | 6 | 96.9 | 69.8 |
| 16 | Hexane | 2 | RaNi | 2.6 | 100 | 300 | 1400 | 4 | 51.7 | 69.4 |
| 17 | Hexane | 2 | RaNi | 1.3 | 100 | 1000 | 1400 | 17 | 100 | 69.5 |
| 18 | Hexane/EtOAc | 2 | RaNi | 2.6 | 100 | 200 | 1400 | 5 | 82.9 | 74.3 |
| | | | | Effect of prolonged Contact w. Catalyst | | | | | | |
| 19 | Hexane | 2 | RaNi | 1.3 | 100 | 1000 | 1400 | 64 | 100 | 69.5 |
| 20 | Hexane | 2 | RaNi | 2.6 | 100 | 1000 | 1400 | 5 | 100 | 70.7 |

TABLE 13-continued

Data on the hydrogenation of 3,3-dimethylbutene
Oxide to 3,3-dimethylbutan-1-ol-1

| # | Solvent | DMEB ml | Catalyst | Weight g | Temp °C. | Press psi | Start Rate RPM | Reaction Time | Conversion | Sel** % |
|---|---------|---------|----------|----------|----------|-----------|----------------|---------------|------------|---------|
| Temperature Effect | | | | | | | | | | |
| 21 | Hexane | 2 | RaNi | 2.6 | 90 | 1000 | 1400 | 6 | 22.2 | 63.9 |
| 22 | Hexane | 2 | RaNi | 2.6 | 100 | 1000 | 1400 | 5 | 100 | 70.0 |
| 23 | Hexane | 2 | RaNi | 2.6 | 120 | 1000 | 1400 | 5 | 65.2 | 68.9 |
| 24 | Hexane | 2 | RaNi | 2.6 | 140 | 1000 | 1400 | 5 | 100 | 75.7 |
| 25 | Hexane | 2 | RaNi | 2.6 | 150 | 1000 | 1400 | 5 | 100 | 76.6 |
| 26 | Hexane | 2 | RaNi | 2.6 | 160 | 1000 | 1400 | 5 | 100 | 75.6 |
| Stirring Effect | | | | | | | | | | |
| 27 | Hexane | 4 | RaNi | 2.6 | 140 | 100 | 400 | 19 | 100 | 42.9* |
| 28 | Hexane | 2 | Ra—Ni | 2.6 | 140 | 200 | 400 | 5 | 97.6 | 53.1 |
| 29 | Hexane | 2 | RaNi | 2.6 | 140 | 200 | 1600 | 5 | 100 | 78.1 |
| 30 | Hexane | 4 | Ra—Ni | 2.6 | 160 | 200 | 600 | 5 | 89.1 | 57.6 |
| 31 | Hexane | 4 | Ra—Ni | 2.6 | 160 | 200 | 1600 | 5 | 98.4 | 70.0 |
| 32 | Hexane | 4 | Ra—Ni | 2.6 | 140 | 400 | 1000 | 5 | 100 | 74.9 |
| 33 | Hexane | 4 | Ra—Ni | 2.6 | 140 | 400 | 2000 | 5 | 100 | 77.6 |
| 34 | Hexane | 4 | Ra—Ni | 2.6 | 140 | 400 | 3000 | 5 | 100 | 75.8 |
| Pressure Effect | | | | | | | | | | |
| 35 | Hexane | 2 | RaNi | 2.6 | 140 | 200 | 1600 | 5 | 100 | 78.1 |
| 36 | Hexane | 4 | Ra—Ni | 2.6 | 140 | 200 | 1400 | 5 | 100 | 55.9 |
| 37 | Hexane | 4 | Ra—Ni | 2.6 | 140 | 300 | 1400 | 17 | 100 | 69.0 |
| 38 | Hexane | 4 | Ra—Ni | 2.6 | 140 | 400 | 1400 | 17 | 100 | 75.7 |
| 39 | Hexane | 4 | Ra—Ni | 2.6 | 140 | 600 | 1400 | 5 | 100 | 75.3 |
| 40 | Hexane | 4 | RaNi | 2.6 | 140 | 1000 | 1500 | 5 | 100 | 66.6 |
| Catalyst Effect | | | | | | | | | | |
| 41 | Hexane | 4 | 5601* | 2.6 | 140 | 200 | 1600 | 5 | 100 | 66.8 |
| 42 | Hexane | 4 | 4200* | 2.6 | 140 | 200 | 1600 | 5 | 100 | 66.2 |
| 43 | Hexane | 4 | 2800* | 2.6 | 140 | 200 | 1600 | 5 | 100 | 74.1 |
| 44 | Hexane | 4 | 5% Pd/C | 0.25 | 140 | 200 | 1600 | 18 | 100 | 43.8 |
| 45 | Hexane | 4 | 5% Pt/C | 0.25 | 140 | 200 | 1600 | | 3,3-dimethyl-butane | |

*In Runs 41–43 the Ra—Ni samples were supplied by WR Grace, Raney Division
**Selectivity to 3,3-dimethylbutane-1-ol

EXAMPLE 26

Aluminum chloride catalyst (2.5 g) and pentane (5 mL) were charged to a 100 mL three neck round bottom flask equipped with a Trubore Stirrer (ACE Glass), gas dispersion tube and thermometer. The mixture was cooled to −40° C. using a dry ice-acetone bath. To the well stirred catalyst suspension, 2-chloro-2-methylpropene (25 g) was added dropwise while the temperature was maintained at −40° C. The ethylene was run through the liquid phase at a rate of 70 mL/min, as controlled by a flowmeter and two bubblers, one at the inlet and the second at the outlet of the flask. The temperature was kept between −18° and −22° C. The reaction was completed in three hours when the ethylene absorption slowed significantly (as determined by the flow rates in the front and back bubblers). The liquid product was decanted from the catalyst and transferred into a separatory funnel, washed with distilled water (5 mL) and dried over $CaCl_2$ (1 g) for two hours. The yield of 1-chloro-3,3-dimethylbutane based on GC analysis was 49%. The two other major components were the $C_8$ chloride (25%) with RT 3.88 minutes and another unidentified product with RT at 2.88 minutes, likely an isomeric $C_6$ chloride.

EXAMPLE 27

In a series of alkylation/esterification reactions, sulfate esters of 3,3-dimethylbutanol were produced by reaction of isobutylene, ethylene and sulfuric acid. Sulfuric acid and heptane were charged to a 300 mL ACE glass reaction flask which was provided with a Teflon coated stir bar, and lines for ethylene and isobutylene delivery. The charge was cooled to −15° C. and placed under constant ethylene pressure. The isobutylene charge for each run was initially transferred to a graduated flask separate from the reaction flask, and then delivered to the reaction flask at a substantially constant rate over a period of hours as the reaction proceeded. During reaction, the temperature was maintained at −15° C. using a dry ice-acetone cooling bath. Charge amounts, charge ratios, periods over which isobutylene addition was accomplished, and reaction conditions are set forth Table 14.

The 3,3-dimethylbutyl sulfate esters produced in the reaction were hydrolyzed to 3,3-dimethylbutanol. After completion of the reaction in runs NS 109 and NS 112, the acid layer was neutralized with NaOH to pH=3, the organic layer was extracted twice with ether, and the remaining aqueous layer refluxed overnight. In runs NS113 and NS115, after isobutylene addition was completed, ethylene pressure was released and water was added in small portions while the reaction mass was maintained at −15° C. by cooling in the dry-ice acetone bath. In each hydrolysis run, the alkylation/esterification reaction mixture was transferred into a two neck round bottom flask and refluxed overnight under argon. The yields entered in Table 14 are based on GC-MS analysis using dodecane as the internal standard. No attempt was made to isolate the alcohol by distillation to determine practical yield of the reaction.

Exemplary of the runs of this example is run NS114 in which sulfuric acid (26.3 g; 0.27 mol) and hexane (90 mL) were charged to the 300 mL reaction flask. Isobutylene (11 g; 0.196 mol) was initially transferred to the separate graduated flask which served as a reservoir for delivery of isobutylene during the reaction. The reaction flask was purged twice with ethylene and held open under ethylene line pressure of 100 psig. The reactor was immersed in the dry ice-acetone bath which had been precooled to −15 degrees C. The temperature of the reactor was monitored by a K type thermocouple inserted into a Teflon coated thermowell. The isobutylene reservoir was kept under nitrogen pressure of 130 psig. Isobutylene addition was initiated at a rate of 0.05 mL/minute while the contents of the reaction flask were stirred at the maximum rate possible. The temperature was maintained at −15 degrees C. throughout the run by addition of dry ice to the cooling bath. Addition of the full isobutylene charge required 5.75 hours. The reaction mixture was stirred for an additional 30 minutes, after which the ethylene pressure was released and water (100 mL) was added dropwise while the temperature was maintained at −15 degrees C. Thereafter, the reaction mixture was transferred to the two neck round bottom hydrolysis flask and refluxed overnight under argon at 85 degrees C. The organic layer was then separated, the acidic layer was extracted twice with 30 mL aliquots of ether, and the combined organic phases were washed once with 10% $Na_2CO_3$ solution followed by 10% NaCl solution. After the washed organic layer had been dried over $MgSO_4$ for three hours, dodecane (5 mL; 4.14 g) was added as an internal standard and the mixture was analyzed by GC-MS. The amount of 3,3-dimethylbutanol thus determined was 10.8 g which, based on a theoretical of 19.99 g, represented a 54% yield.

EXAMPLE 28

Further alkylation/esterification and hydrolysis reaction runs were conducted substantially in the manner described in Example 27 except that the total isobutylene charge, total sulfuric acid charge, ethylene pressure, and time of isobutylene addition in the alkylation/esterification step, and the conditions of the hydrolysis step, were as set forth in Table 15. In all runs, after the addition of isobutylene, the ethylene pressure was released and water was added in small portions at −15 degrees C. The reaction mixture was transferred to a two neck round bottom flask and refluxed overnight under argon at the temperature indicated in Table 15. Yields were determined by GC-MS analysis, using dodecane as the internal standard. Further kinetic studies at 90 degrees C. revealed that alcohol formation was practically completed in 3 hours, and that further heat treatment overnight only increased the $C_{12}$ ether formation up to about 20 area % based on CC analysis.

A further run of this example (run 159) was carried out at the same reactant ratios as run 158. After isobutylene addition, the mixture was heated to ambient, and the heptane layer was then separated and analyzed by GC-MS. The amount of $C_6$ alcohol as determined using dodecane as the standard was 900 mg (4.5% from the theoretical yield). The acidic layer was transferred into a distillation setup, water (50 mL) was added, and the water-azeotrope was continuously distilled at 102–103 degrees C. The water layer was recycled three times and a total of 12.5 g organic product was collected. The GC analysis of the crude product showed $C_6$-alcohol (64.4 area %) $C_{12}$-ether (24%), higher boiling unidentified product (4.8%) and ballast heptane. The combined calculated yield from both layers was 46% crude alcohol.

TABLE 14

| | Run # | | | | | |
|---|---|---|---|---|---|---|
| | 141 | 142 | 143 | 144 | 145 | 146 |
| Ethylene Pressure | 75 | 90 | 90 | 90 | 100 | 100 |
| Temperature | −15 | −15 | −15 | −15 | −15 | −15 |
| Reactants | | | | | | |
| a. $H_2SO_4$, mol | 0.27 | 0.22 | 0.27 | 0.27 | 0.22 | 0.27 |
| b. $C_4$, mol | 0.196 | 0.196 | 0.196 | 0.196 | 0.196 | 0.196 |
| c. solvent, ml | 93 | 50 | 90 | 90 | 90 | 90 |
| Ratios: | | | | | | |
| a. solvent/$H_2SO_4$, mol/mol | 6.5 | 4.3 | 6.5 | 6.5 | 7.7 | 6.3 |
| b. $H_2SO_4/C_4$, mol/mol | 1.38 | 1.12 | 1.38 | 1.38 | 1.12 | 1.38 |
| c. solvent/$C_4$ | 4.9 | 2.7 | 4.9 | 4.9 | 4.9 | 4.9 |
| Time of addition $C_4$ | 5 | 3.5 | 5 | 7 | 7 | 5.45 |
| Hydrolysis of the sulfate | Neutralized NaOH, reflux 3 hrs at pH = 3.5 | Neutralized NaOH, reflux 3 hrs at pH = 3.5 | Neutralized NaOH, reflux 0.5 hrs at pH = 3.5 | 50 ml $H_2O$ 80° C., overnight | 30 ml $H_2O$ 80° C., overnight | 100 ml $H_2O$ 80° C., overnight |
| Yield, % | 18.8 | 10.3 | 25 | 37.2 | 28.3 | 54 |

TABLE 15

| | Run # | | | | | | | | |
|---|---|---|---|---|---|---|---|---|---|
| | 150 | 151 | 152 | 153 | 154 | 155 | 156 | 157 | 158 |
| Ethylene Pressure | 100 | 100 | 100 | 100 | 100 | 100 | 115 | 115 | 115 |
| Temperature | −15 | −15 | −15 | −15 | −15 | −15 | −15 | −15 | −15 |
| Reactants | | | | | | | | | |
| a. $H_2SO_4$, mol | 0.27 | 0.27 | 0.27 | 0.27 | 0.27 | 0.27 | 0.27 | 0.176 | 0.176 |
| b. $C_4$, mol | 0.196 | 0.196 | 0.196 | 0.196 | 0.196 | 0.196 | 0.196 | 0.13 | 0.13 |
| C. solvent, ml | 90 | 90 | 90 | 90 | 90 | 90 | 90 | 59 | 59 |
| Ratios: | | | | | | | | | |
| a. solvent/$H_2SO_4$, ml/ml | 6.3 | 6.3 | 6.3 | 6.3 | 6.3 | 6.3 | 6.3 | 6.3 | 6.3 |
| b. $H_2SO_4/C_4$, mol/mol | 1.37 | 1.37 | 1.37 | 1.37 | 1.37 | 1.37 | 1.37 | 1.37 | 1.37 |
| c. solvent/$C_4$ ml/ml | 4.9 | 4.9 | 4.9 | 4.9 | 4.9 | 4.9 | 4.9 | 4.9 | 4.9 |
| Time of addition $C_4$ | 7 | 5.5 | 6.3 | 6.3 | 6.0 | 6.0 | 5.25 | 3.75 | 3.75 |
| Hydrolysis of the sulfate | 100 ml $H_2O$ 68° C., overnight reflux | 50 ml $H_2O$ 0.07 mol NaOH 85° C., overnight reflux | 50 ml $H_2O$ 0.07 mol NaOH 85° C., overnight reflux | 50 ml $H_2O$ 0.1 mol NaCL 85° C., overnight reflux | 100 ml $H_2O$ 100° C., overnight reflux | 100 ml $H_2O$ 91° C., overnight reflux | 100 ml $H_2O$ 75° C., overnight reflux | 65 ml $H_2O$ 74° C., overnight reflux | 65 ml $H_2O$ 80° C., overnight reflux |
| Yield of 3,3-DMB alcohol | 35% | 49% | 42% | 45% | 55% | 55% | 20% | 19% | 36% |

EXAMPLE 29

Alkylation/esterification reaction studies were conducted in which heptane was used as a solvent and the ratio of heptane to sulfuric acid was gradually reduced from run to run. In the final run (164), no solvent was used. The reactions were conducted substantially as set forth in Example 28 at an ethylene pressure of 110 psig, a temperature −15 degrees C., an isobutylene addition time of 6 hours, and a molar ratio of isobutylene to sulfuric acid of 2. In all but the solvent-free run, a portion of the solvent (20 mL) was mixed with the isobutylene charge (20 mL) in the isobutylene delivery flask. The remainder of the solvent was charged directly to the reaction flask. Isobutylene addition time varied from 3 to 6 hours. After an additional twenty minutes of stirring, the ethylene pressure was released and water (100 mL) was added to the reaction in small portions, while the temperature was maintained at 0° C. The heptane layer was then separated and the acidic sulfate layer was transferred into a 500 mL two neck round bottom flask, equipped with suba seal septa in the side arm and a Vigreux column, Dean Stark receiver and reflux condenser at the center neck. The resultant hydrolysis feed mixture was distilled and the water condensate collected in the Dean Stark receiver and continuously returned to the distillation flask. The organic phase of the condensate was dried over $CaCl_2$ and analyzed by GC-MC. The chromatogram showed traces of heptane, t-butyl-3,3-dimethylbutyl ether, $C_6$ alcohol and higher esters (not identified). Yields of 3,3-dimethylbutanol were in the 59–63% range, but in the absence of solvent the yield was significantly reduced due to oligomerization. Process conditions and results of the runs of these Examples are set forth in Table 16.

TABLE 16

| | Run # | | | | | | |
|---|---|---|---|---|---|---|---|
| | 160 | 161 | 162 | 163 | 164 | 165 | 166 |
| Ethylene Pressure | 110 | 110 | 110 | 110 | 110 | 110 | 110 |
| Temperature | −15 | −15 | −15 | −15 | −15 | −15 | −15 |
| Reactants | | | | | | | |
| a. $H_2SO_4$, mol | 0.428 | 0.428 | 0.428 | 0.428 | 0.428 | 0.428 | 0.428 |
| b. $C_4$, mol | 0.214 | 0.214 | 0.214 | 0.214 | 0.214 | 0.214 | 0.214 |
| c. solvent, ml | Heptane, 200 | Heptane, 100 | Heptane, 50 | Heptane, 25 | Heptane, 0 | Heptane, 100 | Heptane, 100 |
| Ratios: | | | | | | | |
| a. solvent/$H_2SO_4$, ml/ml | 8.77 | 4.38 | 2.19 | 1.095 | 0 | 4.38 | 4.38 |
| b. $H_2SO_4/C_4$, mol/mol | 2 | 2 | 2 | 2 | 2 | 2 | 2 |
| c. solvent/$C_4$, ml/ml | 10 | 5 | 2.5 | 1.25 | 0 | 5 | 5 |
| Time of add $C_4$ (extra time) | 6 | 5.8 | 6 | 6 | 5.8 | 3 hrs. + 2 hrs. | 3 hrs + 0 |

TABLE 16-continued

| | Run # | | | | | | |
|---|---|---|---|---|---|---|---|
| | 160 | 161 | 162 | 163 | 164 | 165 | 166 |
| Hydrolysis of the sulfate | 100 ml H$_2$O at 0° C., reactive distillation | 100 ml H$_2$O at 0° C., reactive distillation | 100 ml H$_2$O at 0° C., reactive distillation | 100 ml H$_2$O at 0° C., reactive distillation | 100 ml H$_2$O at 0° C., reactive distillation | 100 ml H$_2$O at 0° C., reactive distillation | 100 ml H$_2$O at 0° C., reactive distillation |
| Weight distilled product, g | 15.4 | 15.3 | 15.6 | 17.3 | 10.3 | 15.2 | 15.0 |
| GC purity of the 3-3DMB alcohol | 84.0% | 86.6% | 86.2% | 79.1% | 37.9 | 86.6% | 89.7% |
| Isolated Yield of 3,3-DMP alcohol % | 59.0 | 60.1 | 62.6 | 62.6 | 17.8 | 60.1 | 61.5 |

The results of Table 16 showed that isobutylene addition time did not have a significant effect on yield.

EXAMPLE 30

Alkylation/esterification and hydrolysis reactions were carried out substantially in the manner described in Example 28. All alklylation/esterification reactions were conducted in a 300 mL round bottom flask equipped with a Teflon coated power magnetic stirrer, and the temperature was monitored by a thermocouple, inserted in a Teflon thermowell, connected to a temperature controller. The reaction flask was immersed in a acetone-dry ice cooling bath.

In a representative run, the 300 mL ACE round bottom reaction flask was initially charged with 98% sulfuric acid (22.8 mL; 41.9 g; 0.428 mol) and heptane (30 mL). The flask was cooled to −15° C. at which point the ethylene pressure was slowly raised to 110 psi and maintained at that setting during the entire run. A second 75 mL ACE flask was charged with heptane (20 mL) and isobutylene (20 mL; 12 g; 0.214 mol). The second flask was pressurized to 120 psi and the heptane/isobutylene mixture was added dropwise to the 300 mL reaction flask at a rate of 0.2 mL/min. During the addition, the temperature was kept at −15° C. It required three hours for the isobutylene solution to be added over the stirred sulfuric acid-heptane suspension. The stirring was continued for an additional twenty minutes. The ethylene pressure was gradually released, the temperature was raised to 0° C., and water (100 mL) was added at such rate the temperature did not exceed 0° C. The heptane layer was separated and the acidic sulfate layer was transferred into a 500 mL two neck round bottom flask, equipped with suba seal septa in the side arm and a Vigreux column, Dean Stark receiver and reflux condenser at the center neck. During distillation, the water condensate was collected in the Dean Stark receiver and continuously returned to the distillation flask. The organic condensate was collected and analyzed by GC-MC. Conditions of the reactions and results obtained are set forth in Table 17.

TABLE 17

| | Run # | | | | | | | | |
|---|---|---|---|---|---|---|---|---|---|
| | 170 | 171 | 172 | 173 | 174 | 175 | 176 | 177 | 178 |
| Ethylene Pressure | 110 | 110 | 110 | 110 | 110 | 110 | 110 | 110 | −110 |
| Temperature | −15 | −15 | −15 | −15 | −15 | −5 | −5 | −15 | −25 |
| Reactants | | | | | | | | | |
| a. H$_2$SO$_4$, mol | 0.428 | 0.428 | 0.428 | 0.321 | 0.428 | 0.535 | 0.428 | 0.428 | 0.428 |
| b. C$_4$, mol | 0.214 | 0.214 | 0.214 | 0.214 | 0.214 | 0.214 | 0.214 | 0.214 | 0.214 |
| c. solvent, ml | Heptane, 50 | Hexane, 50 | Pentane, 50 | Heptane, 50 | Heptane, 50 | Heptane, 50 | Heptane, 50 | Heptane, 50 | Heptane, 50 |
| Ratios: | | | | | | | | | |
| a. solvent/H$_2$SO$_4$, mol/mol | 2.19 | 2.19 | 2.19 | 2.92 | 2.19 | 1.75 | 2.19 | 2.19 | 2.19 |
| b. H$_2$SO$_4$/C$_4$, mol/mol | 2 | 2 | 2 | 1.5 | 2 | 2.5 | 2 | 2 | 2 |
| c. solvent/C$_4$ ml/ml | 2.5 | 2.5 | 2.5 | 2.5 | 2.5 | 2.5 | 2.5 | 2.5 | 2.5 |
| Time of addition C$_4$ hrs. | 3 | 3 | 3 | 3 | 3 | 3 | 3 | 3 | 3 |
| Hydrolysis of the sulfate | 100 ml H$_2$O at 0°, reactive distillation | 100 ml H$_2$O at 0°, reactive distillation | 100 ml H$_2$O at 0°, reactive distillation | 100 ml H$_2$O at 0°, reactive distillation | 100 ml H$_2$O at 0°, reactive distillation | 100 ml H$_2$O at 0°, reactive distillation | 100 ml H$_2$O at 0°, reactive distillation | 100 ml H$_2$O at 0°, reactive distillation | 100 ml H$_2$O at 0°, reactive distillation |
| Weight distilled | 16.2 | 14.0 | 16.0 | 12.5 | 16.2 | 16.8 | 15.0 | 15.6 | 15.0 |
| Isolated yield of % 3,3-DMB alcohol | 58.8 | 53.6 | 63.1 | 41.3 | 58.8 | 64.3 | 49.8 | 58.8 | 54.5 |
| Color crude 3,3-DMB alcohol | white | white | white | white | white | white | white | white | white |
| Remarks | * | ** | * | * | * | * | * | * | * |

*the alkylsulfate was diluted with water after the syntheses and kept at 5° C. overnight. Distilled on the next day
**the hexane contains around 30–35% methylcyclopentane TABLE 17-continued

| | Run # | | | |
|---|---|---|---|---|
| | 179 | 17A | 17B | 17C |
| Ethylene Pressure | 110 | 110 | 110 | 110 |
| Temperature, ° C. | −15 | −15 | −15 | −15 |
| Reactants | | | | |
| a. $H_2SO_4$, mol | 0.428 | 0.428 | 0.428 | 0.428 |
| b. $C_4$, mol | 0.214 | 0.214 | 0.214 | 0.214 |
| c. solvent, ml | Heptane, 50 | Heptane, 50 | Heptane, 50 | Heptane, 50 |
| Ratios: | | | | |
| a. solvent/$H_2SO_4$, ml/ml | 2.19 | 2.19 | 2.19 | 2.19 |
| b. $H_2SO_4$/$C_4$, mol/mol | 2 | 2 | 2 | 2 |
| c. solvent/$C_4$ ml/ml | 2.5 | 2.5 | 2.5 | 2.5 |
| Time of addition $C_4$ hrs | 3 | 3 | 3 | 3 |
| Hydrolysis of the sulfate | 10 ml $H_2O$ at 0° C. reactive distillation | 40 ml $H_2O$ at 0° C. reactive distillation | 100 ml $H_2O$ at 0° C. reactive distillation | 150 ml $H_2O$ at 0° C. reactive distillation |
| Weight distilled product, g | 6.0 | 19.0 | 18.4 | 13.4 |
| Isolated yield of 3,3-DMB alcohol | — | 47.3 | 53.7 | 48.3 |
| Color crude 3,3-DMB alcohol | Dark brown | Dark yellow | Light yellow | White |
| Remarks | * | * | * | ** |

*the alkylsulfate was kept in refrigerator at 5° C. overnight and the water added prior distillation
**the alkylsulfate was diluted with water after the synthesis and kept at 5° C. overnight. Distilled next day.

| | Run # | | | |
|---|---|---|---|---|
| | 17D | 17E | 17F | 17G |
| Ethylene Pressure | 110 | 110 | 110 | 110 |
| Temperature, ° C. | −15 | −15 | −15 | −15 |
| Reactants | | | | |
| a. $H_2SO_4$, mol | 0.428 | 0.428 | 0.428 | 0.428 |
| b. $C_4$, mol | 0.214 | 0.214 | 0.214 | 0.214 |
| c. solvent, ml | Heptane, 50 | Heptane, 50 | Heptane, 50 | Heptane, 50 |
| Added sulfate additive | None | Yes | None | Yes |
| Ratios: | | | | |
| a. solvent/$H_2SO_4$, ml/ml | 2.19 | 2.19 | 2.19 | 2.19 |
| b. $H_2SO_4$/$C_4$, mol/mol | 2 | 2 | 2 | 2 |
| c. solvent/$C_4$ ml/ml | 2.5 | 2.5 | 2.5 | 2.5 |
| Time of addition $C_4$ hrs | 3 | 3 | 3 | 3 |
| Hydrolysis of the sulfate | 100 ml $H_2O$ at 0° C. reactive distillation | 100 ml $H_2O$ at 0° C. reactive distillation | 100 ml $H_2O$ at 0° C. reactive distillation | 100 ml $H_2O$ at 0° C. reactive distillation |
| Weight distilled product, g | 18.4 | 21.05 | 16.1 | 21.3 |
| Isolated yield 3,3-DMB alcohol | 53.7 | 48.9 | 58.5 | 51.6 |
| Color crude 3,3-DMB alcohol | Dark yellow | Yellow | Pale yellow | White |
| Remarks | * | ** | ** | ** |

*the alkylsulfate was kept in refrigerator at 5° C. overnight and the water added prior distillation
*the alkylsulfate was diluted with water after the synthesis and kept at 5° C. overnight. Distilled next day.

| | Run # | | | | |
|---|---|---|---|---|---|
| | 17H | 17I | 17J | 17K | 17L |
| Ethylene Pressure | 110 | 110 | 110 | 110 | 110 |
| Temperature, ° C. | −15 | −15 | −15 | −15 | −15 |
| Reactants | | | | | |
| a. $H_2SO_4$, ml/g/mol | 22.8/41.9/0.428 | 22.8/41.9/0.428 | 22.8/41.9/0.428 | 22.8/41.9/0.428 | 22.8/41.9/0.428 |
| b. $C_4$, ml/g/mol | 20/12/0.214 | 20/12/0.214 | 20/12/0.214 | 20/12/0.214 | 20/12/0.214 |
| c. solvent, ml | Heptane, 50 | Heptane, 50 | Decane, 50 | Heptane, 50 | Heptane, 50 |
| Ratios: | | | | | |
| a. solvent/$H_2SO_4$, ml/ml | 2.19 | 2.19 | 2.19 | 2.19 | 2.19 |
| b. $H_2SO_4$/$C_4$, mol/mol | 2 | 2 | 2 | 2 | 2 |
| c. solvent/$C_4$ ml/ml | 2.5 | 2.5 | 2.5 | 2.5 | 2.5 |
| Time of addition $C_4$ hrs | 3 | 3 | 3 | 3 | 3 |
| Hydrolysis of the sulfate | 100 ml $H_2O$ at 0° C. reactive distillation | 6.9 g NaOH in 100 ml $H_2O$ at 0° C. distillation | 100 ml $H_2O$ at 0° C. reactive distillation | 100 ml $H_2O$ at 0° C. reactive distillation | 100 ml $H_2O$ at 0° C. reactive distillation |

TABLE 17-continued

| Weight distilled product, g | 16 | 16 | 37.6 (w/decane) | 16.0 | 12.1 |
|---|---|---|---|---|---|
| Isolated yield 3,3-DMB alcohol | 48.9 | 56.0 | 74.4 (alcohol only) | 55.2 | 52.4 |
| Color crude 3,3-DMB alcohol | Pale yellow | Yellow | White | | Pale |
| Remarks | Distillation under Argon** | NaOH added to the water** | Decane kept during distillation** | Liquid-liquid extraction** | Vacuum during distillation** |

*the alkylsulfate was kept in refrigerator at 5° C. overnight and the water added prior distillation
*the alkylsulfate was diluted with water after the synthesis and kept at 5° C. overnight. Distilled next day.

In the runs of this example it was observed that: the optimum volumetric ratio of solvent (heptane) to isobutylene was between about 1.25 and about 2.5, with about 0.75 to about 1.5 mL heptane/mL isobutylene in the initial charge to the reaction flask and 0.5 to 1.0 mL heptane per mL isobutylene being added with the isobutylene; pentane was the solvent generally providing the most favorable results in the alkylation/esterification reaction; sulfuric acid to isobutylene ratio was optimal in the neighborhood of 2.5; the optimal alkylation/esterification reaction temperature was in the range of about −15° C.; at the scale at which the reactions were conducted, the optimal isobutylene addition rate was 0.2 mL/min, and the optimal water charge to the hydrolysis reaction was about 100 mL; the optimal temperature for water addition was 0° C.; and addition of water immediately after alkylation/esterification helped to minimize color bodies in the organic phase of the distillate obtained from the reactive distillation.

In the reactive distillation, it was observed that a large portion of the alcohol accumulated in the distillation pot as a separate phase above and in contact with the acid phase, causing a decrease in selectivity and effectively lower yield. Of the stratagems used to resolve this problem, the most effective was the use of a decane as a solvent for both reaction steps. Liquid/liquid extraction was considered as an alternative for removing the alcohol immediately upon formation; but liquid/liquid extraction was not tested in the runs of this example.

EXAMPLE 31

To a 1 L reactor was charged 96% by weight sulfuric acid (98.94 g; 1 mol) and heptane (200 mL; 133.3 g, 1.33 mmol). After the system was flushed with nitrogen, and with an approximate stir rate of 1500 rpm the reaction mass was cooled to ca. −15° C. At this temperature an overhead pressure of 120 psig ethylene was added and maintained at 120 psig throughout the course of reaction. Five minutes after the ethylene pressure was applied a metered addition of isobutylene was initiated at the rate of 1 mL/min (density of isobutylene=−0.59, 0.59/g/min) while the reaction was maintained at −15° and a metered addition of sulfuric acid (96%) was initiated at a rate of 1.25 g/min. After three hours of simultaneous addition of isobutylene and sulfuric acid, the sulfuric acid addition was terminated (323.6 g total sulfuric acid to the reaction, 3.17 mol) and the isobutylene addition continued for an additional 1.5 hr with a continuous gradient beginning at 1 mL/min down to 0.5 mL/hr (2.61 mol total isobutylene added). The head pressure of ethylene was vented upon the termination of isobutylene addition (total uptake of ethylene was 2.82 mol under these conditions). The crude reaction mass was removed from the reactor and allowed to separate into two liquid layers. The top layer was removed as a light yellow liquid (295.9 g, 162.6 g weight gain) while the bottom layer was a viscous yellow oil (490.3 g, 166.7 g weight gain).

Analysis of the layers was carried out by $^1$H NMR in $CDCl_3$ via integration of alkylsulfate groups vs. a known amount of added toluene (internal NMR standard) to obtain a mol % 3,3-dimethylbutylsulfate groups. (46.7% yield vs. $H_2SO_4$; 52.5% yield vs. ethylene; 56.8% yield vs. isobutylene).

The acid layer (490.3 g) obtained from the above reaction was added to a 3 L flask and to this water (980.6 g) was added dropwise while the acid layer was cooled in an ice bath. The resulting hydrolysis reaction mixture was then heated to a pot temperature of 99–111° C. during which an azeotrope of water and 3,3-dimethylbutanol was recovered via distillation. Three sequential overhead fractions were collected and analyzed, with the results summarized in Table 18 below.

TABLE 18

Results from Reactive Distillation

| | Fraction #1 | Fraction #2 | Fraction #3 |
|---|---|---|---|
| Head Temperature ° C. | 73–83 | 83–86 | 86 |
| Pot Temperature ° C. | 99–108 | 107–111 | 111 |
| Weight (g, organic) | 20.51 | 79.65 | 35.9 |
| Weight 3,3-DMB alcohol (g) | 8 | 55.4 | 26.6 |

The total weight of recovered 3,3-dimethylbutanol was 90 g (1.12 mol) for an overall yield based on $H_2SO_4$ of 27.8%, based on ethlene of 31.3% and based on isobutylene of 33.8%.

EXAMPLE 32

To a 1 L reactor was charged 96% by weight sulfuric acid (98.04 g; 1 mol) and heptane (200 mL; 133.3 g; 1.33 mmol). After the system was flushed with nitrogen, and with an appropriate stir rate of 1500 rpm the reaction mass was cooled to ca. −15° C. At this temperature an overhead pressure of 120 psig ethylene was added and maintained at 120 psig throughout the first 3 hours of reaction. Five minutes after the ethylene pressure was applied a metered addition of isobutylene was initiated at the rate of 1 Ml/min (Density of isobutylene=0.59, 0.59 g/min) while the reaction was maintained at −15° C. and a metered addition of sulfuric acid (96%) was initiated at a rate of 1.56 g/min. After three hours of simultaneous addition of isobutylene and sulfuric acid, the sulfuric acid addition was terminated (380.24 g total sulfuric acid to the reaction 3.72 mol), the ethylene reservoir was closed to the reactor and the isobutylene addition continued for an additional 1.5 hr with a continuous gradient beginning at 1 mL/min down to 0.5 mL/hr (2.61 mol total isobutylene added). The head pressure of ethylene was vented upon the termination of isobutylene addition (total uptake of ethylene was 2.3 mol under these conditions). The reaction mass was removed from the reactor and allowed to separate into two liquid layers. The top layer was removed as a light yellow liquid (166 g, 32.7 g weight gain) while the bottom layer was a viscous yellow oil (524.25 g, 144 g weight gain).

Analysis of the layers was carried out by $^1$H NMR in $CDCl_3$ via integration of alkylsulfate groups vs. a known amount of added toluene (internal NMR standard) to obtain a mol % 3,3-dimethylbutylsulfate groups. (48.3% yield vs. $H_2SO_4$; 78.3% yield vs. ethylene; 69% yield vs. isobutylene).

The 524.25 g acid layer obtained from the above reaction was added to a 3 L flask and to this was added 1048.5 g water dropwise while the acid layer was cooled in an ice bath. The resulting hydrolysis reaction mixture was then heated to a pot temperature of 99–111° C. during which an azeotrope of water and 3,3-dimethylbutanol was recovered via distillation.

The total weight of recovered 3,3-dimethylbutanol was 114.6 g (1.12 mol) for an overall yield based on H2SO4 of 30.2%, based on ethylene of 48.8% and based on isobutylene of 43.1%.

EXAMPLE 33

To a 1 L reactor was charged 96% by weight sulfuric acid (135 g; 1.32 mol) and heptane (480 mL; 319 g). After the system was flushed with nitrogen, and with an approximate stir rate of 1500 rpm, the reaction mass was cooled to ca. −15° C. At this temperature an overhead pressure of 115 psig ethylene was added and maintained at 115 psig throughout the course of reaction. Five minutes after the ethylene pressure was applied a metered addition of isobutylene was initiated at the rate of 0.24 mL/min (density of isobutylene=0.59, 0.14 g/min) while the reaction was maintained at −15° C. After three and one half hours of addition of isobutylene (0.55 mol), the head pressure of ethylene was vented (total uptake of ethylene was 2.28 mol under these conditions). The contents of the reactor were removed from the reactor and allowed to separate into two liquid layers. The top layer was remo0ved as a light yellow liquid (338.8 g, 14.8 g weight gain) while the bottom layer was a viscous yellow oil (168.5 g, 33.5 g weight gain).

Analysis of the layers were carried out by $^1$H NMR in $CDCl_3$ via integration of alkylsulfate groups vs. a known amount of added toluene (internal NMR standard) to obtain a mol % 3,3-dimethylbutylsulfate groups. (24% yield vs. H2SO4; 13.9% yield vs. ethylene; 57.6% yield vs. isobutylene).

The acid layer (168.5 g) obtained from the above reaction was added to a 1 L flask and to this water (337 g) was added dropwise while the acid layer was cooled in an ice bath. The resulting hydrolysis charge mixture was then heated to a pot temperature of 99–111° C. during which an azeotrope of water and 3,3-dimethylbutanol was recovered via distillation.

The total weight of recovered 3,3-dimethylbutanol was 29.7 g (0.29 mol) for an overall yield based on $H_2SO_4$ of 22%, based on ethylene of 12.8% and based on isobutylene of 52.8%.

EXAMPLE 34

Three batches of crude alkylsulfate were produced via the procedures generally described in Example 33, under the particular conditions given below in Table 19, to provide the yields listed in Table 19.

TABLE 19

Batch Reactions Generating Aklylsulfate Mixtures for Hydrolysis Studies

|  | Batch #1 | Batch #2 | Batch #3 |
|---|---|---|---|
| H$_2$SO$_4$ (g) initial charge | 98.04 | 98.04 | 98.04 |
| H$_2$SO$_4$ addition rate (g/min) | 1.45 | 1.68 | 1.6 |
| Total H$_2$SO$_4$ Addition Time | 3 | 3 | 3 |
| H$_2$SO$_4$ total (g) | 359.3 | 399.8 | 386.8 |
| H$_2$SO$_4$ (mol) | 3.52 | 3.92 | 3.79 |
| Isobutylene (g) | 145.7 | 146.1 | 146.1 |
| Initial Rate Isobutylene mL/min | 1 | 1 | 1 |
| Isobutylene (mol) | 2.6 | 2.61 | 2.61 |
| Ethylene Pressure (psig) | 120 | 120 | 120 |
| Ethylene (g) | 40.6 | 50.4 | 50.7 |
| Ethylene (mol) | 1.45 | 1.8 | 1.81 |
| Heptane (g) | 133.3 | 133.3 | 133.3 |
| Total Isobutylene addition time (hr) | 4.5 | 4.5 | 4.5 |
| Heptane/H$_2$SO$_4$ (wt:wt) | 0.37 | 0.33 | 0.34 |
| Isobutylene/Sulfuric Addition Rate (mol) | 0.71 | 0.61 | 0.65 |
| Final Heptane wt (g) | 182.6 | 187.7 | 183.04 |
| Final Acid weight (g) | 484 | 540.2 | 521.4 |
| Wt gain in Heptane (g) | 49.3 | 54.5 | 49.7 |
| Wt gain in acid (g) | 124.7 | 140.4 | 134.6 |
| mol 3,3-DMB esters | 1.06 | 1.34 | 1.48 |
| % H$_2$SO$_4$ to 3,3-DMB esters | 30.1 | 34.2 | 39.1 |
| % ethylene to 3,3-DMB esters | 73.1 | 74.4 | 81.8 |
| % isobutylene to 3,3-DMB esters | 40.7 | 51.4 | 56.7 |

Each batch was divided into three equal parts, a control run was carried out with one part while variations in the hydrolysis conditions were made with the other two portions. Table 20 below summarizes the results of this study. As indicated, one run was made with twice the hydrolysis water addition of Example 33, another with 0.5 times the water addition, another under reflux conditions during the hydrolysis, another with addition of water to the pregnant liquor layer at reactive distillation temperature (99°–110° C.), and still another with addition of pregnant liquor to water at that temperature.

TABLE 20

Hydrolysis Studies to 3,3-Dimethylbutanol

| Reaction | Acid wt (g) | Water (g) | Organic layer (g) | 3,3-DMB (g) | % Organic as 3,3-DMB | % Relative to Control |
|---|---|---|---|---|---|---|
| Control #1 | 151.3 | 151.3 | 31.42 | 25.67 | 81.7 | 100 |
| 2X water | 151.3 | 352.6 | 28.31 | 21.23 | 75.0 | 82.7 |
| Reflux | 151.3 | 151.3 | 26.86 | 20.95 | 78.0 | 81.6 |
| Control #2 | 175.5 | 175.5 | 40.12 | 28.65 | 71.4 | 100 |
| 0.5 water | 175.5 | 87.75 | 42.2 | 32 | 75.8 | 111.7 |
| water to acid | 175.5 | 175.5 | ND | ND | ND | 0 |
| Control #3 | 170 | 170 | 36.66 | 36.66 | 79.8 | 100 |
| acid to water | 170 | 170 | 32.75 | 32.75 | 78.1 | 89.3 |

EXAMPLE 35

The conversion of ethylene, isobutylene and sulfuric acid to 3,3-dimethylbutylsulfate, as mentioned above, is complicated by two major competing reactions. The competitive reaction of sulfuric acid with ethylene resulting in the formation of ethylsulfate groups is one competitive pathway which would be expected to become more significant with an increase in ethylene pressure (concentration increase). Significantly, the other major side reaction, the oligomerization of isobutylene would be expected to increase with an increase in the relative amounts of isobutylene vs. ethylene. These competitive side reactions, because of their diametrically opposed relationship to the relative concentration of each olefin, necessitates an optimal range of conditions/concentrations for the desired formation of 3,3-dimethylbutylsulfate. Example 7, supra, describes conditions which generated 3,3-dimethylbuytlsulfate with high selectivity by the continuous introduction of sulfuric acid and isobutylene to a reaction zone containing heptane and ethylene. The first column of Table 21 below summarizes the results from this procedure. In continuing studies of this reaction, the scale was increased from a 100 cc reaction zone to a 1 liter reaction zone. Table 21 below further summarizes the results obtained by transferring the conditions described for the small scale reaction to the one liter scale.

TABLE 21

One Liter Reactor Studies for 3,3-Dimethylbutylsulfate

|  | 100 cc | 1 L | 1 L-ethylene hold | patent |
|---|---|---|---|---|
| $H_2SO_4$ (g) charge | 5 | 98.04 | 98.04 | 135 |
| $H_2SO_4$ addition rate (g/min) | 0.08 | 1.25 | 1.56 | 0 |
| Total $H_2SO_4$ Addition Time | 3 | 3 | 3 | 0 |
| $H_2SO_4$ total (g) | 19.8 | 323.6 | 380.24 | 135 |
| $H_2SO_4$ (mol) | 0.194 | 3.17 | 3.72 | 1.32 |
| Isobutylene (g) | 9.7 | 146 | 146 | 30.9 |
| Initial Rate Isobutylene mL/min | 0.056 | 1 | 1 | 0.24 |
| Isobutylene (mol) | 0.173 | 2.61 | 2.61 | 0.55 |
| Ethylene Pressure (psig) | 120 | 120 | 120 | 115 |
| Ethylene (g) | 6.78 | 78.96 | 64.4 | 63.84 |
| Ethylene (mol) | 0.242 | 2.82 | 2.3 | 2.28 |
| Heptane (g) | 6.65 | 133.3 | 133.3 | 319 |
| Total Isobutylene Addition time (hr) | 6 | 4.5 | 4.5 | 3.5 |
| Heptane/$H_2SO_4$ (wt:wt) | 0.35 | 0.41 | 0.35 | 2.36 |
| Isobutylene/Sulfuric Addition Rate (mol) | 0.72 | 0.83 | 0.66 | N/A |
| Final Heptane wt (g) | 7.74 | 295.9 | 166 | 333.79 |
| Final Acid weight (g) | 30.7 | 490.3 | 524.25 | 168.5 |
| Wt gain in Heptane (g) | 0.9 | 162.6 | 32.7 | 14.79 |
| Wt gain in acid (g) | 11.1 | 166.7 | 144.01 | 33.5 |
| mol 3,3-DMB esters | 0.114 | 1.48 | 1.8 | 0.318 |
| mol ethyl esters | 0.011 | ND | 0.2 | 0.056 |
| % $H_2SO_4$ to 3,3-DMB esters | 59 | 46.7 | 48.3 | 24.0 |
| % ethylene to 3,3-DMB esters | 47 | 52.5 | 78.3 | 13.9 |
| % isobutylene to 3,3-DMB esters | 66 | 56.8 | 69.0 | 57.6 |
| water added for distillation (g) | — | 980.6 | 1048.5 | 337 |
| 3,3 DMB recovered | — | 90 | 114.6 | 29.7 |
| mol 3,3-DMB recovered | — | 0.88 | 1.12 | 0.29 |
| % $H_2SO_4$ to 3,3-DMB | — | 27.8 | 30.2 | 22.0 |
| % ethylene to 3,3-DMB | — | 31.3 | 48.8 | 12.8 |
| % isobutylene to 3,3-DMB | — | 33.8 | 43.1 | 52.8 |

EXAMPLE 36

Typically, at the completion of isobutylene addition, the reaction is terminated by the release of any excess ethylene pressure in the reactor system (Reaction under a constant pressure of ethylene). To reduce the loss in yield associated with this ethylene purge from the sytem reaction conditions were explored which reduced the ethylene content in the reaction system prior to venting the system. A summary of the results obtained by closing the reactor system to a continuous feed of ethylene after 3 hours of total reaction time (the point at which the addition of sulfuric acid was complete) is given in Table 21 above.

It will be seen that the yield of product based on consumed ethylene dramatically increased as a result of less ethylene lost due to the purge at the completion of reaction.

As a result of the changes in process parameters described above, significant advantages in yield and in productivity (lbs. product vs. volume of reactants/solvent) were achieved.

EXAMPLE 37

Catalytic dehydrogenation runs were conducted comparing the effect of varying the loading of a catalyst material commercially available from Engelhard Corporation.

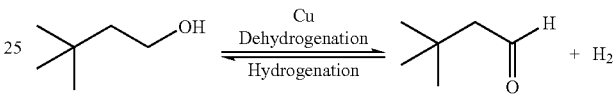

XRF analysis of the commercial catalyst as received from Englehard Corporation, Cu-0330 XLT, gave the following elemental composition:

| Element | % |
|---|---|
| Na | 1.2 |
| Al | 14.9 |
| Si | <0.1 |
| Ca | <0.1 |
| Mn | <0.1 |
| Cu | 37.4 |

Physical Property measurements as supplied by Engelhard are given in Table 22 below.

TABLE 22

Catalyst Properties

| Catalyst | Cu-0330XLT |
|---|---|
| Surface Area (m/g) | 30 |
| Pore volume (ml/g) | 0.16 |
| Density (g/mL) | 1.63 |
| Crush strength (lb/mm) | 11.3 |
| particle type | tablet |
| particle size (diameter in inches) | 0.125 |

B.E.T. surface area and pore volume analyses were performed, yielding the following data:

| BET Surface Area | 26.6 $m^2/g$ |
|---|---|
| Total Pore Volume | 0.118 $cm^3/g$ |

Runs were conducted to compare the effect of three different catalyst loadings (1 g, 2 g and 4 g) at a total flow of 200 sccm (3.33 cm s$^{-1}$) feed gas, comprised of 5% alcohol of 94% purity (remainder as water), helium as diluent, at ca. 320° C. bed temperature. In the reaction run conducted at a 1 g catalyst loading, conversion to aldehyde increased from about 58% to about 90% in the first hour after startup, then immediately commenced to decay, declining linearly until the run was terminated about 24 hours after startup. Conversion at 24 hours was about 75%.

In the reaction run at 4 g catalyst loading, conversion to aldehyde began at about 93%, dipped to about 90% in the first several hours, recovered to about 93% after 4 hours, and was maintained at 92–94% until about 90 hours, after which it gradually tapered off, to about 92% at 100 hours, 90% at 125 hours, and 88% at the end of the run (142.5 hours).

In the run using an intermediate catalyst loading (2 g), the conversion to aldehyde increased from about 63% to 90% in the first hour or two, held close to 90% until about 21 hours, then progressively declined to about 86% after about 37 hours, whereupon the run was terminated.

The implication of the above results is that onset of deactivation is not linearly related to increase in catalyst weight. At a constant flow the change in catalyst weight directly influences the contact time of gases on catalyst surface.

Contact Time=(Catalyst Volume)/(Total Flow of Gases)

| Grams of Catalyst | Catalyst Volume | Contact Time | Time to Deactivation (hr) |
|---|---|---|---|
| 1 | 0.613 cm$^3$ | 0.184 s | 0 |
| 2 | 1.223 cm$^3$ | 0.37 s | 21 |
| 4 | 2.45 cm$^3$ | 0.74 s | 90 |

Extrapolation of these data suggests that an 8 g catalyst bed operated under the feed composition, temperature, and flow conditions of this example would not begin to deactivate until after about 340 hr of operation.

It is natural to suspect that an increase in catalyst might cause a decrease in selectivity (higher number of active sites might correspond to a greater probability of secondary reactions). However, analysis of product gases established that, in the 4 g catalyst run, selectivity was maintained in excess 98% after the first three or four hours, and very gradually increased throughout the remainder of the run to a value slightly over 99% at the end (142.5 hours). At a catalyst loading of 1 g, selectivity progressively increased from about 97% at the beginning of the run to about 98.5% or 98.7% at the end (24 hours). At a a loading of 2 g, selectivity was worse than for either of the other runs, generally increasing from about 95.2 to 95.4% early in the run to about 97.6 to 97.8% at the end, with several excursions below 95%. Thus, in the range of catalyst loadings which provide optimal catalyst life, selectivity does not decrease with added catalyst; in fact, the selectivity is slightly higher in the case with the largest amount of catalyst tested (also, selectivity appears to slightly gain in favor of aldehyde formation with time on stream).

The added catalyst weight (volume) at a constant flow has a direct impact on productivity of catalyst.

Productivity=quantity of product produced per unit catalyst per unit time; P=mmol aldehyde/gram catalyst hour Operation at 200 sccm feed gas containing 5% by volume 3,3-dimethylbutanol and a catalyst loading of 4 g translates into a productivity of 6 mmol product per gram catalyst per hour (0.6 kg/kg hr). Once deactivation takes place (as evidenced by a decrease in aldehyde production and an increase in alcohol exiting the reactor), rate constants for the linear portion of the deactivation can be calculated (see Table 23, below).

The deactivation rate not only decrease in magnitude with an increase in catalyst, the reduction in rate is not a linear response with additional stability gained by addition of more catalyst.

TABLE 23

Deactivation vs. Catalyst Loading

| grams cat | slope | mmol alcohol/ g cat hr | Productivity/ deactivation |
|---|---|---|---|
| 1 | 0.7399 | 25.1 | 34.0 |
| 2 | 0.2381 | 12.6 | 52.8 |
| 4 | 0.1156 | 6.3 | 54.4 |

The effects of this non-linearity can be related to productivity and is shown in the last column in the table above (a linear response would give a constant Productivity/Deactivation).

The above analysis suggests that an increase in catalyst charge will extend the overall lifetime of catalyst by 1) increasing the time on stream prior to observable deactivation and 2) decreasing the rate of deactivation. Because the benefit gained from increased catalyst life surpasses the penalty associated with decrease in catalyst productivity, it may be desirable in commercial operation to use a catalyst loading significantly in excess of that necessary for satisfactory conversion at startup. For example, at an alcohol content in range of about 4–6% by volume in the feed gas to the reactor, it may be especially preferred to provide a catalyst charge sufficient so that the normal operating space velocity is less than about 2.0 sec$^{-1}$, more preferably between about 1.0 and about 1.5 sec$^{-1}$. A space velocity in the latter range extends the catalyst life while maintaining a reasonable productivity, e.g., in the range of between about 0.45 and about 0.75 kg 3,3-dimethylbutanal/gram catalyst-hour.

EXAMPLE 38

In a further series of anaerobic dehydrogenation runs, the feed gas flow rate was varied (150–300 sccm) at a constant flow of alcohol feed (variable %) and constant weight of catalyst (2 g of Cu-0330XLT). A plot showing the results for aldehyde formation is shown below. The variation in flow rate at a constant charge results in a variation in contact time. A constant flow of alcohol (10 sccm) results in a variable % alcohol in stream.

| Flow Rate | Contact Time | % Alcohol |
|---|---|---|
| 300 sccm | 0.123 s | 3.33 |
| 200 sccm | 0.184 s | 5 |
| 150 sccm | 0.245 | 6.67 |

With a constant flow of alcohol, although the total flow varies, productivity should not be affected as long as conversion is constant. Comparative data for these runs indicated little change in aldehyde production (nor, therefore, conversion of alcohol) resulted from variations in total gas flow rate at constant alcohol rate. However, selectivity was found to decline with increasing gas concentration to the extent that, after 20 hours on stream time, selectivity at 200 sccm and 5% gas strength had risen moderately to about 98%, while selectivity at 150 sccm and 6.67% gas strength had progressively declined to about 94.5%. Interestingly, selectivity at 300 sccm and 3.33% gas fell in between, i.e., just short of 97% at 19 hours. Selectivities may show further divergence at the longer reaction times.

Considering the dependence of catalyst life on catalyst loading relative to 3,3-dimethylbutanol feed rate, together with the independence of performance effects from total flow rate, a preferred mode of operation may be expressed in terms of the product of space velocity and the volume fraction of 3,3-dimethylbutanol in the feed gas, which should be in the range of 0.05 to about 0.08 (cc alcohol)(cc feed gas-sec)$^{-1}$.

EXAMPLE 39

Under commercial operating conditions a common diluent such as nitrogen would be preferred to helium (all of the above examples used helium to dilute the alcohol). Replacement of helium with nitrogen as the diluent was investigated using 1 g Cu-0330XLT with 5% alcohol at a total flow of 200 sccm and a ca. 310° C. bed temperature. No major effect on the conversion to aldehyde resulted from using $N_2$ in place of He as the diluent.

EXAMPLE 40

In the runs of this example, copper catalyst which had been deactivated in the course of dehydrogenation runs was subjected to oxidative regeneration conditions.

From TEM studies it appears that deactivation may be related to the sintering of copper particles. The sintering effect (agglomeration of particles) causes a reduction in copper surface area and therefore, which may result in a reduction in active sites. This agglomeration phenomena is not well understood. Tests were run to determine whether re-oxidation of the copper particles would re-disperse the copper and, therefore, increase its surface area.

Initial efforts focused on the introduction of oxygen (diluted to 10% in helium) at a reaction temperature equivalent to normal operation conditions (ca. 320° C.). A series of three dehydrogenation cycles were run, with two intermediate regeneration cycles.

Dehydrogenation reactions were conducted by introducing a feed gas containing 5% by volume 3,3-dimethylbutanol in helium at a rate of 200 sccm into a catalyst bed containing 1 g Cu0330XLT catalyst, operated at a temperature of 320° C.

The first oxidative "regeneration" of catalyst was actually found to have a negative impact on conversion of alcohol to aldehyde as well as a negative effect on stability (slope of conversion vs. time relationship). Conversion at the end of the first cycle was about 80% after 10 hours. Immediately after regeneration, conversion was quite low, recovering to a maximum of only about 70% before tapering off again. However, the second regeneration cycle proved effective to restore the conversion vs. time profile for the catalyst to approximately the same level of performance as displayed during the second cycle.

Examination of the temperature change associated with the introduction of oxygen into the "reduced" (used) catalyst bed revealed that an exothermic event took place (presumably the oxidation of reduced copper to copper oxides). Because of the possibility that the significant exotherm may have actually caused further sintering of the catalyst, further investigations were conducted under milder "regeneration" conditions. In the latter tests, a regeneration gas containing 10% oxygen (diluted with helium) was introduced at a bed temperature of 250°C between dehydrogenation cycles. An exothermic event again took place upon addition of oxygen which appeared to be complete within 30 minutes of treatment. However, unlike the regeneration with oxygen at 320°C, milder treatment at 250° C. restored a greater % of activity to the catalyst. The selectivity of the catalyst was only slightly affected by the treatment. Operating data from dehydrogenation runs following regeneration at 250° C. demonstrated that the first regeneration caused a rejuvenation of activity (ca. 55% based on the extent of deactivation as evidenced by % aldehyde produced). The second regenerative treatment caused a greater % of reactivation (although the net activity gradually decreased from cycle to cycle).

EXAMPLE 41

A series of dehydrogenation runs was conducted comparing the effect of catalyst loading (1 g, 2 g, and 4 g) at a total flow of 200 sccm (3.33 cm s$^{-1}$) feed gas, comprised of 5% alcohol of >99% purity, helium as diluent. At ca. 320°C bed temperature, it was found that selectivity in the dehydrogenation run with 4 g catalyst selectivity was sharply lower during the first 15 to 20 hours than in the runs using 1 g or 2 g catalyst. The 1 g and 2 g catalyst beds afforded selectivities of well over 90% substantially throughout the dehydrogenation run. During the run using the 4 g bed, selectivity dropped precipitously from an early level above 90% to a level below 70% at about 6 or 7 hours, then rose steadily to a level above 90% at 20 hours, maintaining that level in subsequent operation. Productivity in the production of aldehyde essentially followed the same pattern as selectivity.

Analysis of the by-products produced in the 4 g of catalyst reaction revealed that the increase in catalyst (increase in contact time) gave rise to a large early increase in both the olefin and ester forming reactions. The extent of formation of both of these by-products decreased in importance with time (thereby giving rise to an increase in aldehyde selectivity).

Attempts to increase the performance of Cu-0330CE under excess catalyst conditions (longer contact times) were made by 1) decreasing the bed temperature and by 2) variation of the "ramping" conditions used to bring the catalyst bed to reaction temperature (standard temperature profiles for all reactions, unless noted otherwise include an initial ramp period of 2 hr starting at 250□C). Different temperature profiles were used for three dehydrogentation reaction runs with 4 g of Cu-0330CE. In the first run, reflecting the conditions typically used in the examples above, the bed temperature was ramped from 250° C. to ca. 310□C in about 2 hours and maintained at ca. 310° C.; in the second run, the temperature was ramped from about 210° to about 280° C. in about 2 hours and held at 280° C.; in the third run the temperature was held at about 210° C. for about 4 hours, ramped to about 280° C. over a period of about 2 hours, then held at about 280° C.

Lowering the maximum reaction temperature from 310□C to 280□C (bed temperature) brought about a significant increase in selectivity to aldehyde and overall aldehyde productivity during the first ten hours of operation. Imposing a 4 hr. hold at 220°C provided minimal additional advantage in early selectivity, and resulted in a significant penalty in conversion.

Although lowering the reaction temperature to 280° C. was found effective to establish high selectivity at reasonable productivity early in the dehydrogenation run, lowering the reaction temperature adversely affects the reaction equilibrium, thereby unavoidably lowering the achievable conversion. In an industrial manufacturing facility operated at temperatures below 300° C., it may be necessary to remove unreacted 3,3-dimethylbutanol from the 3,3-dimethylbutanal product of the dehydrogenation, e.g., by distillation, and recycle the alcohol to the dehydrogenation reaction. In each case, the benefit in extended catalyst life achieved by operation at 280° or 290° C. would need to be weighed against the increase in capital and operating associated with incomplete conversion and recycle of 3,3-dimethylbutanol to the dehydrogenation reactor. Moreover, at operating temperatures significantly lower than 275° C., catalyst life may actually suffer.

EXAMPLE 42

Inasmuch as the solubility of water in 3,3-dimethylbutanol is about 6% by weight, the feed gas to an industrial reactor for preparation of 3,3-dimethylbutanal would typically contain about 6% water (13.6 mol %) on an alcohol basis. Dehydrogenation runs were conducted in the manner described in Example 41 (except that 4 g catalyst were used at 280°C bed temperature; Cu-0330CE catalyst) using a 94% 3,3-dimethylbutanol/6% water mixture. The only observable differences noted by this substitution is a shift in by-product production from olefin and ester to carboxylic acid.

EXAMPLE 43

Regeneration of Cu-0330CE was investigated by oxygen (10% in helium) at 250°C on a used 1 g sample. Three dehyrogenation cycles were run, each at 320° C., a feed gas rate of 200 sccm, and a 3,3-dimethylbutanol content in the feed gas of 5%. In the first run, conversion to 3,3-dimethylbutanal was essentially stable at around 88% throughout a 75 hour run. In the second run (after the first regeneration cycle), conversion to 3,3-dimethylbutanal decayed essentially linearly from about 87% to about 85% over the first 50 hours, then somewhat more sharply from 85% to about 82% over the next 15 hours. In the third run (after the second regeneration cycle), conversion decayed linearly from about 86% at the outset to about 84% after 20 hours.

Although oxygen treatment appears to only cause detrimental effects on the performance of the catalyst, conclusions are difficult to draw based on the longevity of this particular catalyst (after 75 hrs. of continuous operation, no significant loss in activity was observed). It is entirely possible that the oxygen treatment had little bearing on the outcome of the performance as evidenced by the pattern of by-product formation. Very little change in olefin production was seen from the end of cycle one to the beginning of cycle two. The pattern suggests the normal drop in olefin production with time. The ester formation did change with a greater production of this by-product with each succeeding cycle. The acid production, very negligible in all cases, did not appear to alter from its normal pattern with each successive cycle. The ether formation may slightly increased with each cycle; however, the changes were minimal and may follow a continuous progression.

EXAMPLE 44

ZnO (CaO added as stabilizer) was evaluated as a dehydrogenation catalyst under standard conditions of 5 wt % alcohol in a total flow of 200 sccm gases at various temperatures.

Conversions were not as good as those demonstrated for Cu catalysts. Yield of aldehyde stablized at about 33–35% at a temperature in the range of 370° C. Increasing the temperature to 400° C. resulted in an increase of aldehyde yield to about 45–46%, from which it deteriorated over the next two hours to about 40%. Selectivity to aldehyde was in the neighborhood of 80–85%.

EXAMPLE 45

The anaerobic catalytic dehydrogenation reaction described in detail above is commercially attractive only at high temperature due to thermodynamic constraints. The introduction of oxygen to the dehydrogenation renders the overall reaction exothermic and therefore thermodynamically more favorable. This should allow for operation at substantially lower temperatures (in cases where the dehydrogenation is operating under thermodynamic constraints and not kinetic constraints).

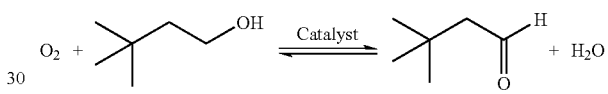

Oxidative dehydrogenation was investigated using ZnO catalyst described above. A feed gas containing 5% by volume 3,3-dimethylbutanol was introduced into a tubular reactor containing ZnO catalyst (4 g). Oxygen was initially introduced into the feed gas at concentration of about 1.5% by volume. Oxidative dehydrogenation was initiated under essentially adiabatic conditions with the temperature rising from about 260° to about 320° C. After about one hour and forty minutes of operation, the oxygen fraction was increased to about 2.5% by volume and reaction continued at 350° C. Aldehyde yield gradually increased from 0 to about 30% over the first hour and stabilized at that level as long as the oxygen concentration was maintained at 1.5%. When the oxygen concentration was stepped up to 2.5%, the aldehyde yield stepped up to about 40% and stayed at about that level through the remainder of the run, i.e., for a little less than two hours after the oxygen concentration was increased. Selectivities ranged from about 85–90% at 1.5% oxygen and in the neighborhood of 80% at 2.5% oxygen.

Although conversions and selectivities of oxidative dehydrogenation over ZnO were not as favorable as those for anaerobic dehydrogenation over a copper catalyst, the addition of oxygen at 2.5% provided slightly higher 3,3-dimethylbutanol yields at 350° C. than was achieved by anaerobic dehydrogenation over ZnO at 365° C.

The addition of oxygen (at least up to 2.5% oxygen in the reaction stream) has a positive effect on aldehyde generation (as evidenced by the gain in production from 1.5% to 2.5% oxygen) without any noticeable change in selectivity. A comparison (not exactly a direct comparison with a 15°C difference in temperature) between the reaction conducted under oxygen free conditions and the above oxygen experiment is shown below.

Again, a clear gain in conversion was observed. The by-products produced in this study are shown below.

The most dominant by-product is olefin formation which is dependent on the concentration of added oxygen.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. A process for the preparation of 3,3-dimethylbutanol comprising:
   heating a hydrolysis feed mixture comprising a 3,3-dimethylbutyl ester and a mineral acid in the presence of water, thereby hydrolyzing the ester and producing a hydrolysis reaction mixture comprising 3,3-dimethylbutanol; and
   distilling 3,3-dimethylbutanol formed in the hydrolysis from the hydrolysis reaction mixture.

2. A process for the preparation of 3,3-dimethylbutanol comprising:
   heating a hydrolysis feed mixture comprising a 3,3-dimethylbutyl ester and a mineral acid in the presence of water, thereby hydrolyzing the ester and producing a hydrolysis reaction mixture comprising 3,3-dimethylbutanol; and
   distilling 3,3-dimethylbutanol formed in the hydrolysis from the hydrolysis reaction mixture as the hydrolysis reaction proceeds.

3. A process as set forth in claim 2 wherein said hydrolysis feed mixture comprises between about 10% and about 75% by weight $H_2S_4$, between about 25% and about 95% water, and between about 1% and about 50% by weight 3,3-dimethylbutyl hydrogen sulfate.

4. A process as set forth in claim 3 wherein said hydrolysis feed mixture further comprises between about 0.5% and about 50% by weight di(3,3-dimethylbutyl) sulfate, both said 3,3-dimethylbutyl hydrogen sulfate and said di(3,3-dimethylbutyl) sulfate being hydrolyzed to 3,3-dimethylbutanol.

5. A process as set forth in claim 3 wherein said distillation is conducted at a head pressure of between about 0.1 atm and about 2 atm and a bottoms temperature of between about 35° and about 175° C.

6. A process as set forth in claim 5 wherein the distillation is conducted at atmospheric head pressure and an overhead condensate fraction rich in 3,3-dimethylbutanol is collected at a temperature of between about 90° and about 99° C.

7. A process as set forth in claim 6 wherein said overhead condensate comprises an azeotrope of 3,3-dimethylbutanol and water.

8. A process as set forth in claim 6 wherein said rich fraction contains at least about 50% by weight 3,3-dimethylbutanol.

9. A process as set forth in claim 8 wherein said rich fraction contains between about 75% and about 95% by weight 3,3-dimethylbutanol.

10. A process as set forth in claim 9 wherein said rich fraction condensate comprises an organic phase containing at least 75% by weight 3,3-dimethylbutanol and an aqueous phase comprising no more than about 2% by weight 3,3-dimethylbutanol.

11. A process as set forth in claim 10 wherein 3,3-dimethylbutanol obtained in said organic phase of said rich fraction is converted to 3,3-dimethylbutanal.

12. A process as set forth in claim 11 wherein 3,3-dimethylbutanol is converted to 3,3-dimethylbutanal by catalytic dehydrogenation.

13. A process as set forth in claim 12 wherein 3,3-dimethylbutanal produced in said catalytic dehydrogenation is reacted with L-α-aspartyl-L-phenylalanine 1-methyl ester in the presence of a reducing agent to produce N-[N-(3,3-dimethybutyl)-L-α-aspartyl]-L-phenylalanine 1-methyl ester.

14. A process as set forth in claim 12 wherein the t-butylacetic acid content of the 3,3-dimethylbutanol product is not greater than about 1% by weight.

15. A process as set forth in claim 2 wherein said 3,3-dimethylbutyl ester is prepared by reacting isobutylene, ethylene, and a mineral acid.

16. A process as set forth in claim 15 wherein isobutylene and ethylene are substantially simultaneously brought into contact with said mineral acid.

17. A process as set forth in claim 15 wherein said mineral acid is sulfuric acid.

18. A process as set forth in claim 15 wherein isobutylene, ethylene, and said mineral acid are reacted in the presence of an organic solvent in an alkylation/esterification reaction zone, thereby producing an alkylation/esterification reaction mixture comprising an organic phase and a pregnant liquor phase, said organic phase comprising said solvent, and said pregnant liquor phase containing said ester and said mineral acid.

19. A process as set forth in claim 18 wherein the volumetric ratio of organic solvent to mineral acid in said alkylation/esterification reaction zone during the alkylation/esterification reaction is less than 4 to 1.

20. A process as set forth in claim 19 wherein the volumetric ratio of organic solvent to mineral acid is less than about 3 to 1.

21. A process as set forth in claim 19 wherein the volumetric ratio of organic solvent to mineral acid is between about 0.1 to 1 and about 2.5 to 1.

22. A process for the preparation of 3,3-dimethylbutanol comprising:
   reacting isobutylene, ethylene, and a mineral acid in the presence of an organic solvent in an alkylation/esterification reaction zone, thereby producing an alkylation/esterification reaction mixture comprising an organic phase and a pregnant liquor phase, said organic phase comprising said solvent, and said pregnant liquor phase containing a 3,3-dimethylbutyl ester and said mineral acid;
   separating said pregnant liquor phase from said organic phase;
   heating a hydrolysis feed mixture comprising said pregnant liquor phase in the presence of water, thereby hydrolyzing the ester contained in said pregnant liquor phase and producing a hydrolysis reaction mixture comprising 3,3-dimethylbutanol; and
   distilling 3,3-dimethylbutanol formed in the hydrolysis from the hydrolysis reaction mixture as the hydrolysis reaction proceeds.

23. A process as set forth in claim 22 comprising diluting said pregnant liquor phase prior to hydrolysis of said ester.

* * * * *

UNITED STATES PATENT AND TRADEMARK OFFICE
CERTIFICATE OF CORRECTION

| | | |
|---|---|---|
| PATENT NO. | : 7,164,049 B2 | |
| APPLICATION NO. | : 10/400558 | |
| DATED | : January 16, 2007 | |
| INVENTOR(S) | : Ebner et al. | |

It is certified that error appears in the above-identified patent and that said Letters Patent is hereby corrected as shown below:

Column 67, claim 3, line 33: "$H_2S_4$" should read -- $H_2SO_4$ --.

Signed and Sealed this

Twenty-seventh Day of November, 2007

JON W. DUDAS
*Director of the United States Patent and Trademark Office*